United States Patent
Chiang et al.

(10) Patent No.: US 6,399,326 B1
(45) Date of Patent: *Jun. 4, 2002

(54) NUCLEIC ACIDS ENCODING NEURAL/PANCREATIC RECEPTOR TYROSINE PHOSPHATASE

(75) Inventors: Ming-Ko Chiang, Boston; John G. Flanagan, Newton, both of MA (US)

(73) Assignee: President and Fellows of Harvard College, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/884,569

(22) Filed: Jun. 27, 1997

Related U.S. Application Data

(60) Provisional application No. 60/021,040, filed on Jul. 2, 1996.

(51) Int. Cl.$^7$ .......................... C12P 21/06; C07H 21/04; C12N 5/00; C12N 15/74
(52) U.S. Cl. .................. 435/69.1; 536/23.5; 435/325; 435/471; 435/252.3; 435/320.1
(58) Field of Search .................. 435/69.1, 196, 435/325, 252.3, 254.11, 69.7, 471, 320.1; 536/23.5, 23.4

(56) References Cited

U.S. PATENT DOCUMENTS 5,989,551 A * 11/1999 Maclaren et al.

FOREIGN PATENT DOCUMENTS

| WO | WO 94/03610 | 2/1994 |
| WO | WO 94.24161 | 10/1994 |

OTHER PUBLICATIONS

Rudinger J. et al. Characteristics of the amino acids as components of a peptide hormone sequence. in Peptide Hormones. pp. 1–7. Edited by Parsons, JA; Mill Hill, London, 1976).*
Adams MD, et al. 3,400 expressed sequence tags identify diversity of transcripts from human brain. Nature Genet. vol. 4, pp. 256–267, 1993.*
Lu et al., Biochem. Biophys. Res. Commun., 204,930–936, Oct. 1994.*
Lewin, Science, 237, 1570, Sep. 1987.*
Reeck et al., Cell, 50,667, Aug. 1987.*
Passini et al., Proc. Natl. Acad. Sci., 92, 9412–9416, Sep. 1995.*
George et al., Macromolecular Sequencing and Synthesis, 127–149, 1988.*
Chiang, M. et al, "PTP–NP, A New Member of the Receptor Protein Tyrosine Phosphatase Family Implicated, in Development of Nervous System and Pancreatic Endocrine Cells," *Development 122*, pp. 2239–2250 (1996).
Kawasaki, E. et al, "Molecular Cloning and Characterization of the Human Transmembrane Protein Tyrosine Phosphatase Homologue, Phogrin, an Autoantigen of Type 1 Diabetes," *Biochemical and Biophysical Research Communications* 227, 440–447 (1996).
Lan, M. et al, "Molecular Cloning and Identification of a Receptor–Type Protein Tyrosine Phosphatase, IA–2, from Human Insulinoma," *DNA and Cell Biology,* vol. 13, No. 5 (1994).
Lu, J. et al, "Identification of a Second Transmembrane Protein Tyrosine Phosphatase, IA–2β, as an Autoantigen in Insulin–Dependent Diabetes Mellitus: Precursor of the 37–kDa Tryptic Fragment," *Prod. Natl. Acad. Sci. USA,* vol. 93, pp. 2307–2311, Mar. (1996).
Smith, P. et al, "ICAAR, a Novel Member of a New Family of Transmembrane Tyrosine Phosphatase–like Proteins," *Biochemical and Biophysical Research Communications* 229, 402–411 (1996).
Wasmeier, C. et al, "Molecular Cloning of Phogrin, a Protein–tyrosine Phosphatase Homologue Localized to Insulin Secretory Granule Membranes," *The Journal of Biological Chemistry,* vol. 271, No. 30, Jul. 26 pp. 18161–18170 (1996).
Fitzgerald et al., Genbank accession U73458, Nov. 16, 1996.

* cited by examiner

Primary Examiner—Gary L. Kunz
Assistant Examiner—Robert S. Landsman
(74) Attorney, Agent, or Firm—Foley, Hoag & Eliot; Isabelle M. Clauss

(57) ABSTRACT

We describe here a new class of protein tyrosine phosphatases (PTP), called "PTP-NP" (for neural and pancreatic) receptors. The sequence of an exemplary PTP-NP gene (SEQ ID No. 1) indicates it encodes a receptor type PTP (SEQ ID No. 2) with a single tyrosine phosphatase domain. Comparison of PTP-NP with the other known PTPs reveals a cysteine-conserved motif in the extracellular domain and, together with their homology in the phosphatase domain, this defines a new subclass of receptor type PTPs.

15 Claims, 12 Drawing Sheets

```
PTP-NP    NAPKNRSLAVLTYDHSRILLKSQNSHGSSDYINASPIMDY    795
mIA-2     NIKKNRHPDFLPYDHARIKLKVESSPSRSDYINASPIIEH    773
B0244.2   FASQNR..TILPEDDNIVDIDGKTAENEDFYLNASFIYDD    409

PTP-NP    DPRNPAYIATOGPLPATVADFWQMVWEGGCAVIVMLTPLS    835
mIA-2     DPRMPAYIATQGPLSHTIADFWQMVWESGCTVIVMLTPLV    813
B0244.2   DPRQAVYIAAQTPASSQLAAFWQTLWQHGVCLVVNLST..    447

PTP-NP    ENGVRQCHHYWPDEGSNLYHVYEVNLVSEHIWCQDFLVRS    875
mIA-2     EDGVKQCDRYWPDEGSSLYHVYEVNLVSEHIWCEDFLVRS    853
B0244.2   PEECKQEKNYWPDTGSEVHGAFETHLVSEHIWSDDYLVPS    487

PTP-NP    FYLKNLQTNETRTVTQFHFLSWYDQGVPSSTRSLLDFRRK    915
mIA-2     FYLKNLQTQETRTLTQFHFLSWPAEGTPASTRPLLDFRRK    893
B0244.2   FYLKNLQNSQTRTITQFHYLSWQKESTPTSAKSILEFRRK    527

PTP-NP    VNKCYRGRSCPIIVHCSDGAGRSGTYVLIDNVLNKMAKGA    955
mIA-2     VNKCYRGTSCPIIVHCSDGAGRTGTYILIDMVLNRMAKGV    933
B0244.2   VNKSYRGRSSAVLVHSWDGSGRTGVYCAVDVLCARLLRGI    567

PTP-NP    KEIDIAATLEHLRDQRPGHVQTKEQFEFALTAVAEEVMAI    995
mIA-2     KEIDIAATLEHVRDQRPGLVRSKDQFEFALTAVAEEVNAI    973
B0244.2   RQIDVVATVEHLRDQRDGMVATGDQFKLVYGCVAQEVNHL    607

PTP-NP    LKALPQ   1001
mIA-2     LKALPQ    979
B0244.2   LKSIAT    613
```

FIG. 2A

```
              *      *       *      *
PTP-NP    GCLEDGLCGSLETCVNDGVFGRC...QKVPVMDTYRYEV    73
mIA-2     GCLEDRRLCSHLEVCIQDGLFGQC...QAGVGQARPLLQV    78
B0244.2   CQNISENLQDNDESCYPDGVFGQCYSSESGSPEPTVLDNL    60

PTP-NP    PPGALLHLEVTLQKLSRTGFTWDDYTQRVIAQ         106
mIA-2     TSPVLQRLQGVLRQLMSQGLSWHDDLTQHVISQ         111
B0244.2   DDTQLELLKLELTRLAAKDKDWGDEETQCVLAY          93
            *   *    *   *
```

FIG. 2B

Figure 3A
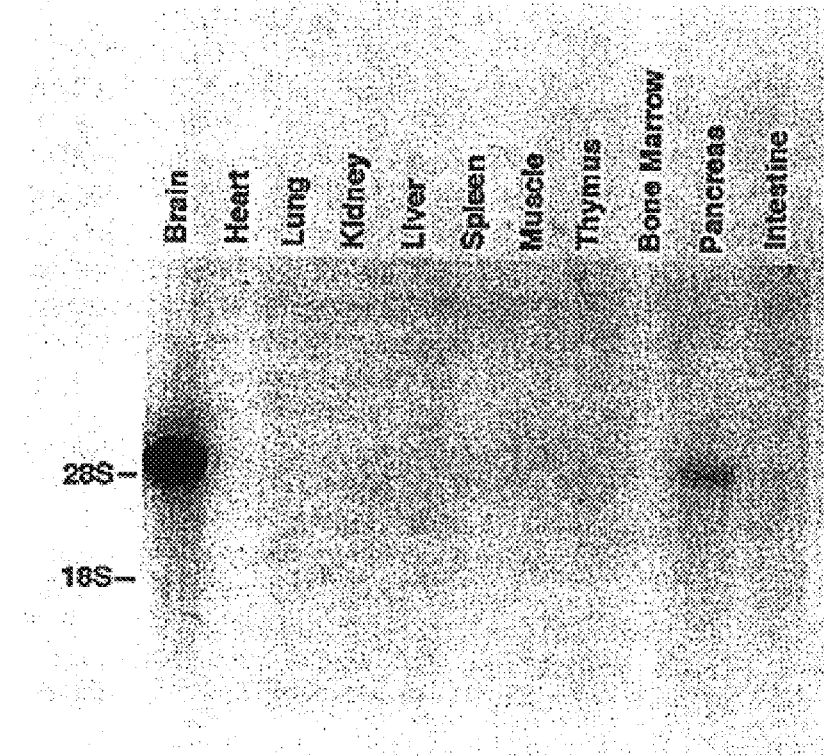
Figure 3B
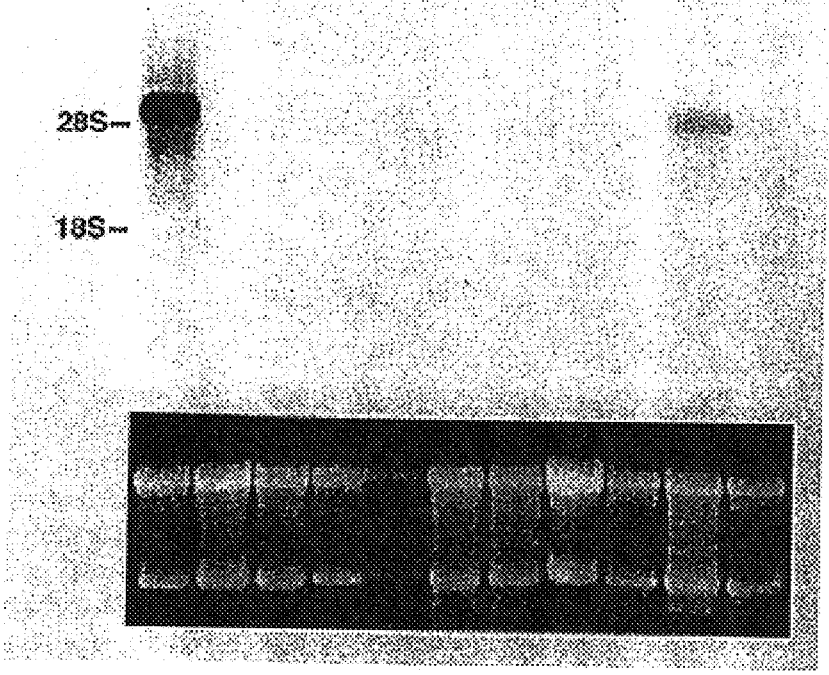
Figure 3C

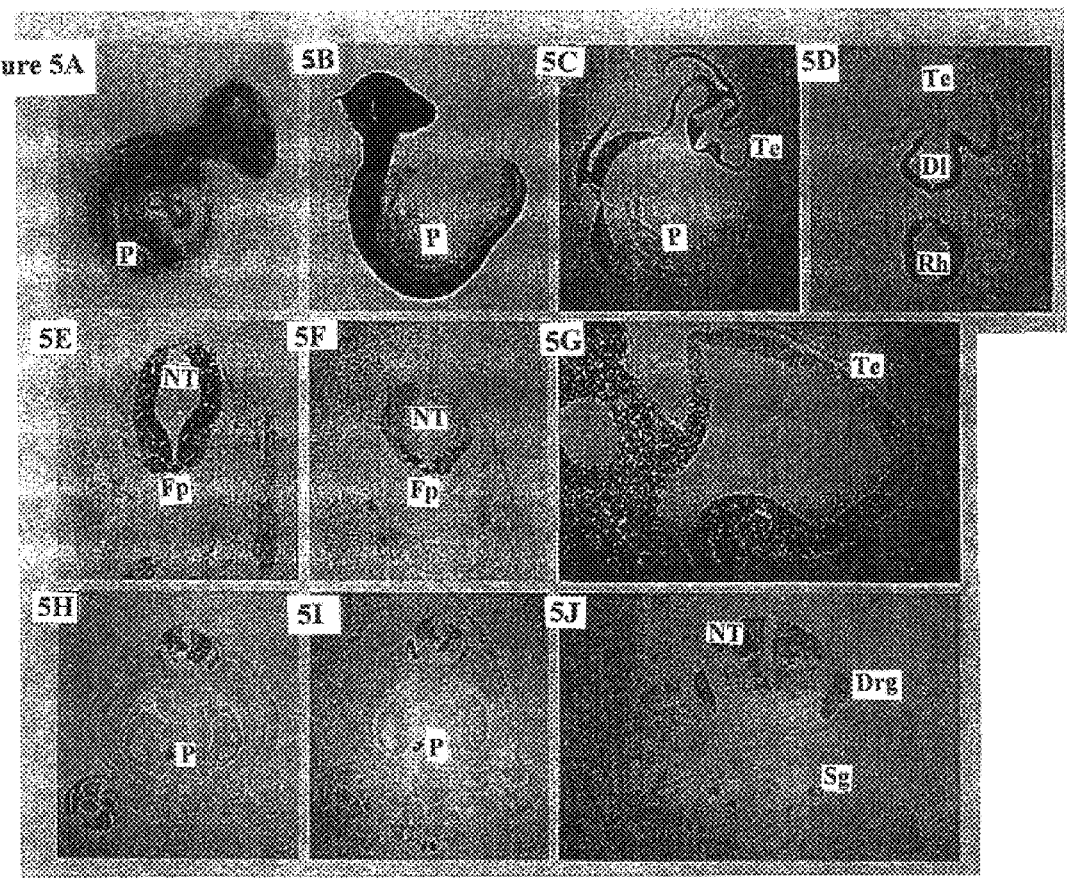

Figure 6A
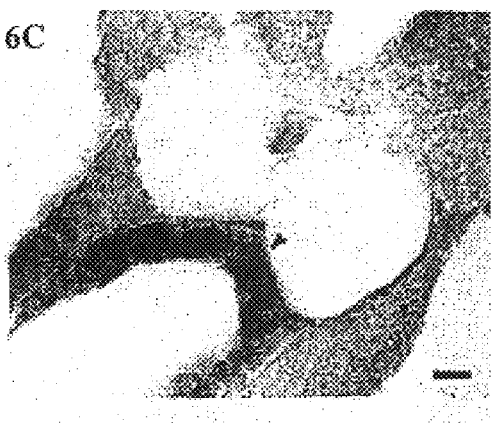
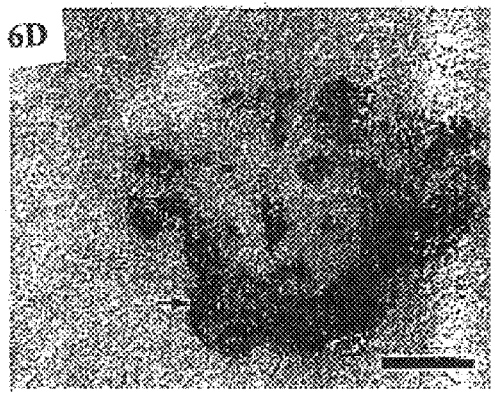
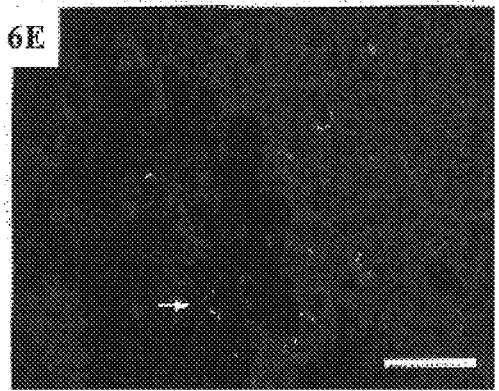
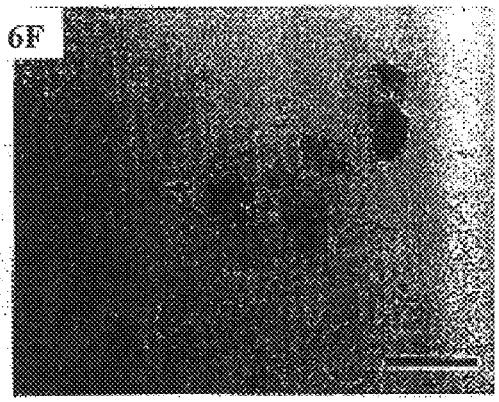
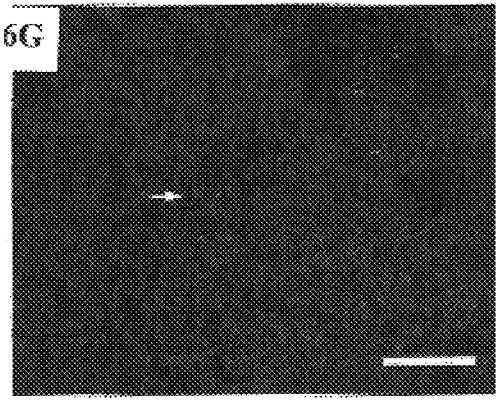

Figure 7A 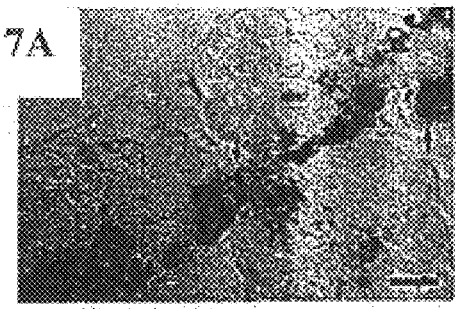 7B 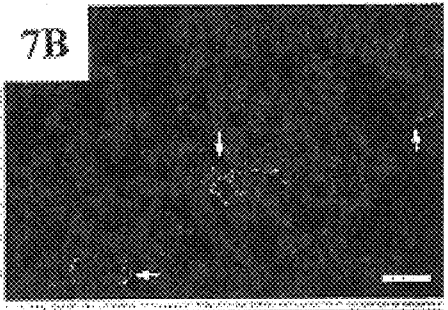
7C  7D 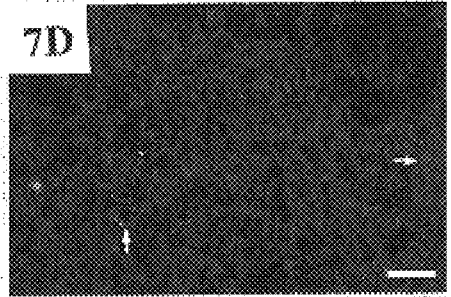
7E 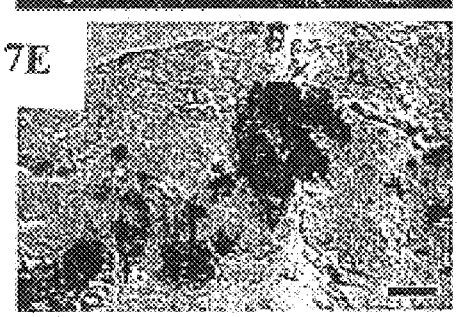 7F 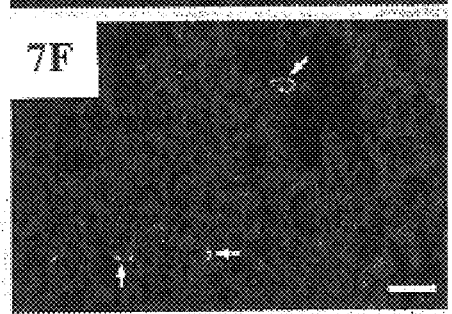
7G 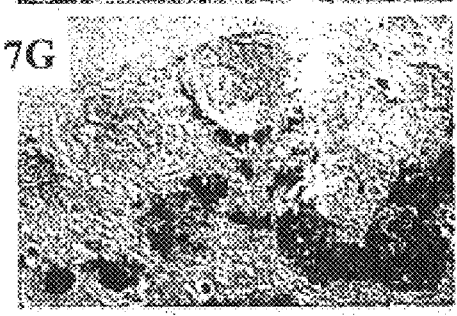 7H 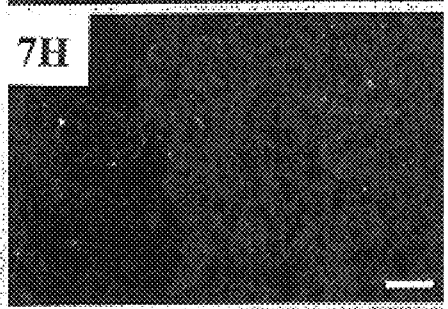
7I 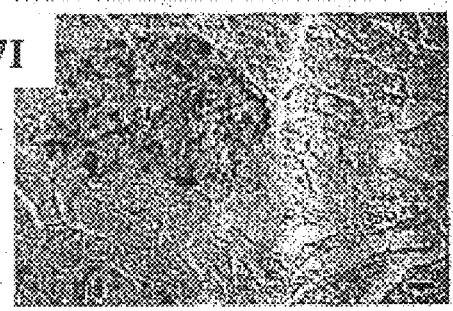 7J 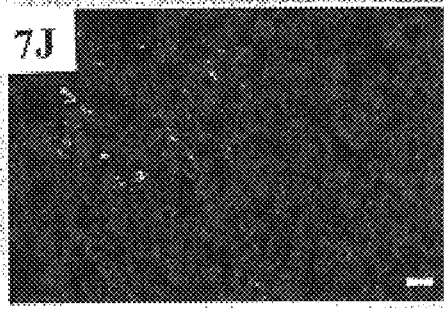

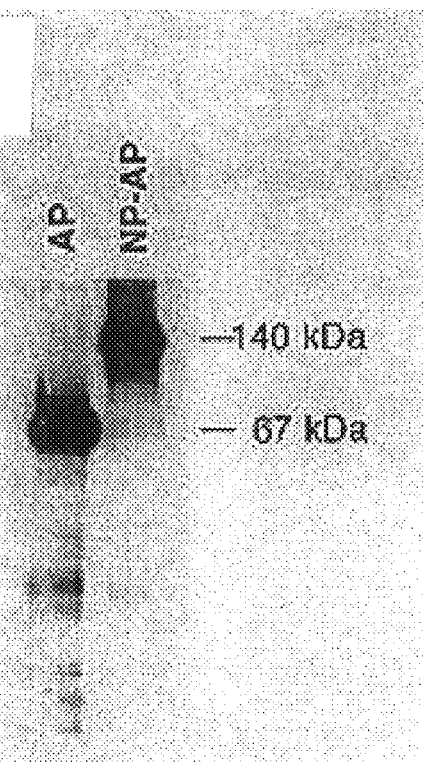
Figure 8A  8B

Figure 9A 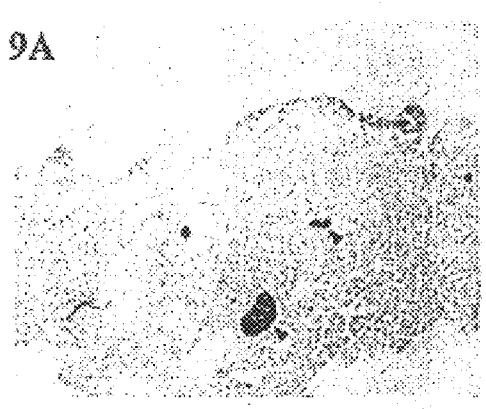 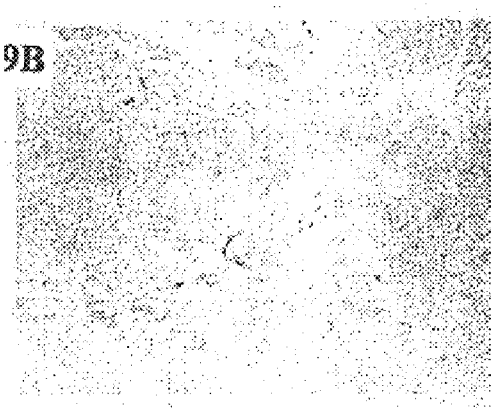 9B
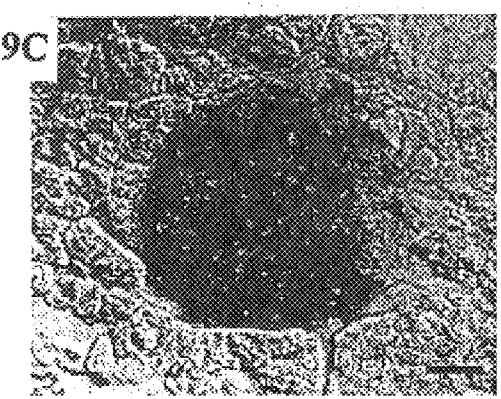 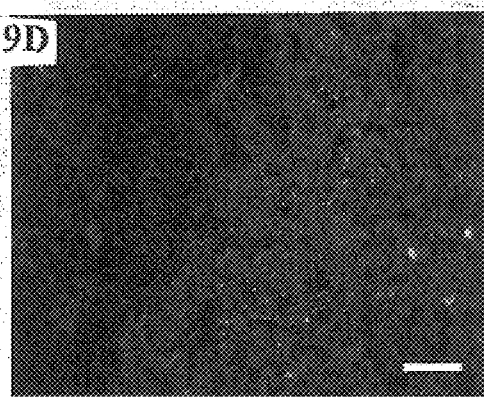
9C 9D
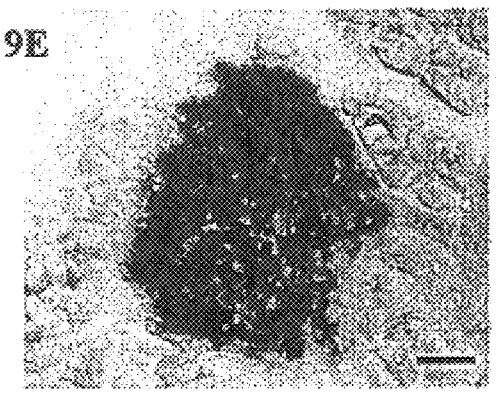 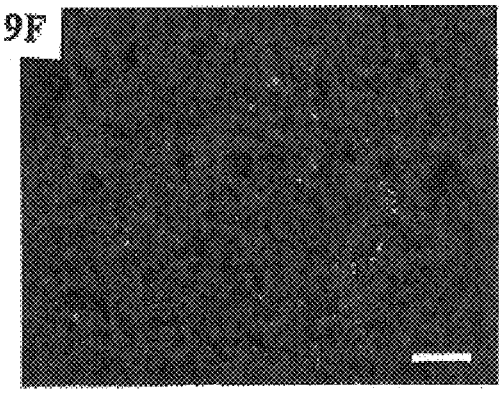
9E 9F
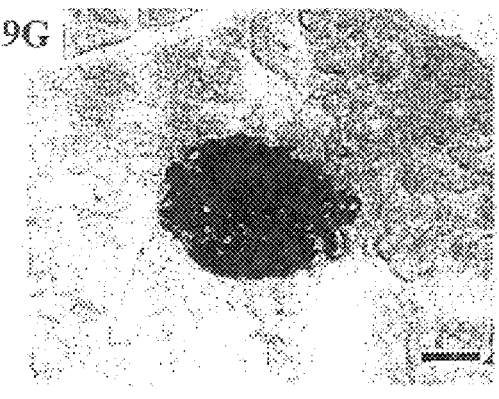 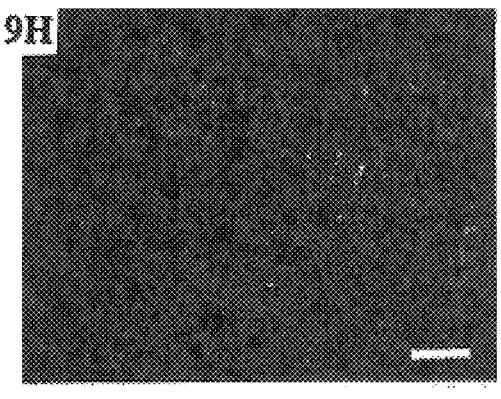
9G 9H

NUCLEIC ACIDS ENCODING NEURAL/PANCREATIC RECEPTOR TYROSINE PHOSPHATASE

REFERENCE TO RELATED APPLICATIONS

This application claims priority to U.S. provisional application No. 60/021,040, filed Jul. 2, 1996, the specification of which is incorporated by reference herein.

GOVERNMENT FUNDING

Work described herein was supported by the National Institutes of Health Grants HD29417 and DK45580. The United States Government has certain rights in the invention.

BACKGROUND OF THE INVENTION

Protein tyrosine phosphorylation has been extensively characterized as a major mechanism of transducing signals within cells. The balance of tyrosine phosphorylation is maintained and modulated by two opposing sets of enzymes, the protein tyrosine kinases (PTKs) and the protein tyrosine phosphatases (PTPs). During embryonic development, several protein tyrosine kinases are known to have powerful and specific roles (Cantley et al., (1991) *Cell* 64:281–302; Fantl et al., (1993) *Annu. Rev. Biochem.* 62:453–481; Imamoto et al., (1994) *Curr. Opin. Gen. Dev.* 4:40–46; van der Geer et al., (1994) *Annu. Rev. Cell Biol.* 10:251–337). Though the PTPs are less well characterized, there is genetic evidence to indicate important functions in specific tissues during development. The Drosophila gene corkscrew, for example, encoding an intracellular PTP, is required for the development of the head and tail of the embryo (Perkins et al., (1992) *Cell* 70:225–236). Mice homozygous for the motheaten (me) allele which encodes a mutated version of the intracellular PTP, hematopoietic cell phosphatase (HCP, also known as SH-PTP1 and PTP1C), have a variety of defects in the immune system (Shultz et al., (1993) *Cell* 73:1445–1454; Tsui et al., (1993) *Nat. Gen.* 4:124–129). Important roles for other PTPs are also indicated by biochemical studies. For instance, an intracellular PTP, FAP-1 (also known as PTP-BAS) has been found to be involved in the signal transduction pathway of apoptosis (Sato et al., (1995) *Science* 268:411–415).

In addition to the phosphatase catalytic domain, many PTPs contain a transmembrane and extracellular domain (Cohen and Cohen, (1989) *J. Biol. Chem.* 264:21345–21438; Hunter, (1989) *Cell* 58:1013–1016; Walton and Dixon, (1993) *Annu. Rev. Biochem.* 62:101–120; Brady-Kalnay and Tonks, (1995) *Curr. Opin. Cell Biol.* 7:650–657). Like the transmembrane PTKs, the transmembrane PTPs could be receptors with the potential to regulate the phosphorylation state of downstream targets in response to binding of extracellular ligands. However, there has heretofore been little evidence on ligands, or on the potential for ligand-induced signaling. Two transmembrane PTPs, PTPm and PTPk, have been demonstrated to exhibit homophilic binding which can cause cell-cell adhesion (Brady-Kalnay et al., (1993) *Curr. Opin. Cell Biol.* 7:650–657; Gebbink et al., (1993) *J. Biol. Chem.* 268:16101–16104; Sap et al., (1994) *Mol. Cell. Biol.* 14:1–9). Another transmembrane PTP, RPTPb, was found to correspond to phosphacan, a proteoglycan that can interact with the adhesion molecules N-CAM and Ng-CAM and the extracellular matrix protein tenascin (Milev et al., (1991) *J. Cell Biol.* 127:1703–1715; Barnea et al., (1994) *J. Biol. Chem.* 269:14349–14352; Grumet et al., (1994) *J. Biol. Chem.* 269:12142–12146), and was also identified as a ligand of the neuronal cell surface molecule contactin (Peles et al., (1995) *Cell* 82:251–260).

In vertebrates and invertebrates, several receptor-type PTPs have been identified with restricted expression patterns in the developing nervous system. In Drosophila, DPTP99A, DPTP10D, and DLAR are transmembrane PTPs with neuron-specific expression, and immunolocalization of these molecules on axons has led to proposals that they may be involved in axon outgrowth and guidance (Tian et al., (1991) *Cell* 67:687–700; Yang et al., (1991) *Cell* 67:661–673). In vertebrates, RPTPb shows expression restricted to the developing nervous system (Carnoll et al., (1993) *Brain Res. Dev. Brain Res.* 75:293–298; Levy et al., (1993) *J. Biol. Chem.* 268:10573–10581). LAR, RPTPs ,and CRYPa were also found expressed in embryonic neuronal tissues (Yan et al., (1993) *J. Biol. Chem.* 268:24880–24886; Stoker (1994) *Mech. Dev.* 46:201–217; Wang et al., (1995) *J. Neurosci. Res.* 41:297–310). In addition, PTPa was found to be induced during neuronal differentiation of P 19 cells (den Hertog et al., (1993) *EMBO J.* 12:3789–3798). Similarly, the expression of two other PTPs, PC12-PTP1 and LAR, was induced in differentiating PC12 cells (Sharama and Lombroso, (1995) *J. Biol. Chem.* 270:49–53; Zhang and Longo, (1995) *J. Cell. Biol.* 128:415–431).

Unlike the nervous system, there is little information on molecular mechanisms for cell-cell signaling in pancreatic development, and no cell-cell signaling molecules specific to the pancreatic lineage have yet been identified. The pancreas is of enormous medical importance, because of its role in widespread diseases, notably juvenile diabetes and pancreatic cancer. Formation of the pancreas during development has been well studied at the morphological and cellular level, but little is known about control of the induction, growth or differentiation of the pancreas at the molecular level (Slack, (1995) *Development* 121:1569–1580). Previous studies have shown some transcription factors expressed in early developing pancreas. In particular, STF-1 (also known as IPF-1, IDX-1, or PDX: Ohlsson et al., (1993) *EMBO J.* 12:4251–4259; Miller et al., (1994) *EMBO J.* 13:1145–1156; and Guz et al., (1995) *Development* 121:11–18), a homeobox gene, is expressed in the pancreatic primordium and adjacent gut endothelium, and has been shown by targeted mutagenesis to be critical for the development of the pancreas (Jonsson et al., (1994) *Development* 114:75–87). However, even though extracellular signals to control pancreatic endocrine development could be clinically useful, the mechanisms of extracellular signaling that control pancreas formation and endocrine cell development are still being elucidated.

SUMMARY OF THE INVENTION

The present invention relates to the discovery of a new class of the receptor protein tyrosine phosphatases (PTP), referred to herein as PTP-NP (for neural and pancreatic) receptors.

In general, the invention features isolated PTP-NP polypeptides, preferably substantially pure preparations of the subject PTP-NP polypeptides. The invention also provides recombinantly produced PTP-NP polypeptides. In preferred embodiments the polypeptide has a biological activity including one or more of: the ability to dephosphorylate a phosphotyrosine residue; hydrolyze a phosphatase substrate such as p-nitrophenylphosphate; bind to a ligand expressed on pancreatic β cells. However, PTP-NP polypeptides which specifically antagonize such activities, such as may be provided by truncation mutants or other dominant negative mutants, are also specifically contemplated.

The PTP-NP proteins of the present invention can be characterized as including one or more of the following domains/motifs: an extracellular domain, having a $cys_4$ domain, which mediate ligand binding, a transmembrane domain, and an intracellular domain including a phosphatase domain. The protein may also include a secretion signal sequence, and (optionally) glycosylated amino acid residues.

In one embodiment, the polypeptide is identical with or homologous to a PTP-NP protein represented in SEQ ID NO: 2. Related members of the PTP-NP family are also contemplated, for instance, a PTP-NP polypeptide preferably has an amino acid sequence at least 65%, 70%, 75% or 80% homologous to the polypeptide represented by. SEQ ID NO: 2, though polypeptides with higher sequence homologies of, for example, 85, 90% and 95% or are also contemplated. In a preferred embodiment, the PTP-NP polypeptide is encoded by a nucleic acid which hybridizes under stringent conditions with a nucleic acid sequence represented in SEQ ID NO: 1. Homologs of the subject PTP-NP proteins also include versions of the protein which are resistant to post-translation modification, as for example, due to mutations which alter modification sites (such as tyrosine, threonine, serine or asparagine residues), or which prevent glycosylation of the protein, or which prevent interaction of the protein with extracellular ligands or with intracellular proteins involved in signal transduction.

The PTP-NP polypeptide can comprise a full length protein, such as represented in SEQ ID NO: 2, or it can comprise a fragment corresponding to one or more particular motifs/domains, or to arbitrary sizes, e.g., at least 5, 10, 25, 50, 100, 150 or 200 amino acids in length. In preferred embodiments, the PTP-NP polypeptide includes a sufficient portion of the extracellular domain to be able to specifically bind to a PTP-NP ligand. Truncated forms of the protein include, but are not limited to, soluble extracellular domain fragments including the $CYS_4$ motif, soluble intracellular domains including the phosphatase domain, and membrane-bound forms of either which include the transmembrane domain. Another preferred fragment includes at least 5, though more preferably at least 10, 20, 30 or more residues N-terminal to proline 282 of SEQ ID NO: 2.

In certain preferred embodiments, the invention features a purified or recombinant PTP-NP polypeptide having a core polypeptide molecular weight of about 111.5 kd including a signal sequence, e.g., in the range of 105 kd to 115 kd. In other embodiments, the peptide core of a mature PTP-NP protein preferably has a molecular weight of about 108.8 kD. It will be understood that certain post-translational modifications, e.g., glycosylation and the like, can increase the apparent molecular weight of the PTP-NP protein relative to the unmodified polypeptide chain.

The subject proteins can also be provided as chimeric molecules, such as in the form of fusion proteins. For instance, the PTP-NP protein can be provided as a recombinant fusion protein which includes a second polypeptide portion, e.g., a second polypeptide having an amino acid sequence unrelated (heterologous) to the PTP-NP polypeptide, e.g. the second polypeptide portion is glutathione-S-transferase, e.g. the second polypeptide portion is an enzymatic activity such as alkaline phosphatase, e.g. the second polypeptide portion is an epitope tag.

In yet another embodiment, the invention features a nucleic acid encoding a PTP-NP polypeptide, which has the ability to modulate, e.g., either mimic or antagonize, at least a portion of the activity of a wild-type PTP-NP polypeptide. An exemplary PTP-NP-encoding nucleic acid sequence is represented by SEQ ID NO: 1.

In another embodiment, the nucleic acid of the present invention includes a coding sequence which hybridizes under stringent conditions with the coding sequence designated in SEQ ID NO: 1. The coding sequence of the nucleic acid can comprise a sequence which is identical to a coding sequence represented in of SEQ ID NO: 1, or it can merely be homologous to that sequences. In preferred embodiments, the nucleic acid encodes a polypeptide which specifically modulates, by acting as either an agonist or antagonist, one or more of the bioactivities of a wild-type PTP-NP polypeptides.

Furthermore, in certain preferred embodiments, the subject PTP-NP nucleic acid will include a transcriptional regulatory sequence, e.g. at least one of a transcriptional promoter or transcriptional enhancer sequence, which regulatory sequence is operably linked to the PTP-NP gene sequence. Such regulatory sequences can be used in to render the PTP-NP gene sequence suitable for use as an expression vector. This invention also contemplates the cells transfected with said expression vector whether prokaryotic or eukaryotic and a method for producing PTP-NP proteins by employing said expression vectors.

In yet another embodiment, the nucleic acid hybridizes under stringent conditions to a nucleic acid probe corresponding to at least 12 consecutive nucleotides of either sense or antisense sequence of SEQ ID NO: 1; though preferably to at least 25 consecutive nucleotides; and more preferably to at least 40, 50 or 75 consecutive nucleotides of either sense or antisense sequence of SEQ ID NO: 1.

Yet another aspect of the present invention concerns an immunogen comprising a PTP-NP polypeptide in an immunogenic preparation, the immunogen being capable of eliciting an immune response specific for a PTP-NP polypeptide; e.g. a humoral response, e.g. an antibody response; e.g. a cellular response. In preferred embodiments, the immunogen comprising an antigenic determinant, e.g. a unique determinant, from the protein represented by SEQ ID NO: 2.

A still further aspect of the present invention features antibodies and antibody preparations specifically reactive with an epitope of the PTP-NP immunogen.

The invention also features transgenic non-human animals, e.g. mice, rats, rabbits, chickens, frogs or pigs, hating a transgene, e.g., animals which include (and preferably express) a heterologous form of a PTP-NP gene described herein, or which misexpress an endogenous PTP-NP gene, e.g., an animal in which expression of one or more of the subject PTP-NP proteins is disrupted. Such a transgenic animal can serve as an animal model for studying cellular and tissue disorders comprising mutated or misexpressed PTP-NP alleles or for use in drug screening.

The invention also provides a probe/primer comprising a substantially purified oligonucleotide, wherein the oligonucleotide comprises a region of nucleotide sequence which hybridizes under stringent conditions to at least 12 consecutive nucleotides of sense or antisense sequence of SEQ ID NO: 1, or naturally occurring mutants thereof. In preferred embodiments, the probe/primer further includes a label group attached thereto and able to be detected. The label group can be selected, e.g., from a group consisting of radioisotopes, fluorescent compounds, enzymes, and enzyme co-factors. Probes of the invention can be used as a part of a diagnostic test kit for identifying dysfunctions associated with mis-expression of a PTP-NP protein, such as for detecting in a sample of cells isolated from a patient, a level of a nucleic acid encoding a PTP-NP protein; e.g. measuring a PTP-NP mRNA level in a cell, or determining whether a genomic PTP-NP gene has been mutated or deleted. These so-called "probes/primers" of the invention can also be used as a part of "antisense" therapy which refers to administration or in situ generation of oligonucleotide probes or their derivatives which specifically hybridize (e.g. bind) under cellular conditions, with the cellular mRNA and/or genomic DNA encoding one or more of the subject PTP-NP proteins so as to inhibit expression of that protein, e.g. by inhibiting transcription and/or translation. Preferably, the oligonucleotide is at least 12 nucleotides in length, though primers of 25, 40, 50, or 75 nucleotides in length are also contemplated.

In yet another aspect, the invention provides an assay for screening test compounds for inhibitors, or alternatively, potentiators, of an interaction between a PTP-NP protein and, for example, a virus, an extracellular ligand of the PTP-NP protein, or an intracellular protein which binds to the PTP-NP protein, e.g., a substrate of the PTP-NP phosphatase activity. An exemplary method includes the steps of (i) combining a PTP-NP polypeptide or bioactive fragments thereof, a PTP-NP target molecule (such as a PTP-NP ligand or a PTP-NP substrate), and a test compound, e.g., under conditions wherein, but for the test compound, the PTP-NP protein and target molecule are able to interact; and (ii) detecting the formation of a complex which includes the PTP-NP protein and the target polypeptide either by directly quantitating the complex, by measuring inductive effects of the PTP-NP protein, or, in the instance of a substrate, measuring the conversion to product. A statistically significant change, such as a decrease, in the interaction of the PTP-NP and target molecule in the presence of a test compound (relative to what is detected in the absence of the test compound) is indicative of a modulation, e.g., inhibition or potentiation, of the interaction between the PTP-NP protein and the target molecule.

Yet another aspect of the present invention concerns a method for modulating one or more of growth, differentiation, or survival of a cell by modulating PTP-NP bioactivity, e.g., by potentiating or disrupting certain protein-protein interactions. In general, whether carried out in vivo, in vitro, or in situ, the method comprises treating the cell with an effective amount of a PTP-NP therapeutic so as to alter, relative to the cell in the absence of treatment, at least one of (i) rate of growth, (ii) differentiation, or (iii) survival of the cell. Accordingly, the method can be carried out with PTP-NP therapeutics such as peptide and peptidomimetics or other molecules identified in the above-referenced drug screens which agonize or antagonize the effects of signaling from a PTP-NP protein or ligand binding of a PTP-NP protein. Other PTP-NP therapeutics include antisense constructs for inhibiting expression of PTP-NP proteins, and dominant negative mutants of PTP-NP proteins which competitively inhibit ligand interactions upstream and signal transduction downstream of the wild-type PTP-NP protein.

Another aspect of the present invention provides a method of determining if a subject, e.g. an animal patient, is at risk for a disorder characterized by unwanted cell proliferation or aberrant control of differentiation or apoptosis. The method includes detecting, in a tissue of the subject, the presence or absence of a genetic lesion characterized by at least one of (i) a mutation of a gene encoding a PTP-NP protein, e.g. represented in SEQ ID NO: 1 or a homolog thereof; or (ii) the mis-expression of a PTP-NP gene. In preferred embodiments, detecting the genetic lesion includes ascertaining the existence of at least one of: a deletion of one or more nucleotides from a PTP-NP gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; a non-wild type level of the protein; and/or an aberrant level of soluble PTP-NP protein.

For example, detecting the genetic lesion can include (i) providing a probe/primer including an oligonucleotide containing a region of nucleotide sequence which hybridizes to a sense or antisense sequence of a PTP-NP gene or naturally occurring mutants thereof, or 5' or 3' flanking sequences naturally associated with the PTP-NP gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the PTP-NP gene and, optionally, of the flanking nucleic acid sequences. For instance, the probe/primer can be employed in a polymerase chain reaction (PCR) or in a ligation chain reaction (LCR). In alternate embodiments, the level of a PTP-NP protein is detected in an immunoassay using an antibody which is specifically immunoreactive with the PTP-NP protein.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

Other features and advantages of the invention will be apparent from the following detailed description, and from the claims.

BRIEF DESCRIPTION OF THE DRAWINGS

Figure 1A:
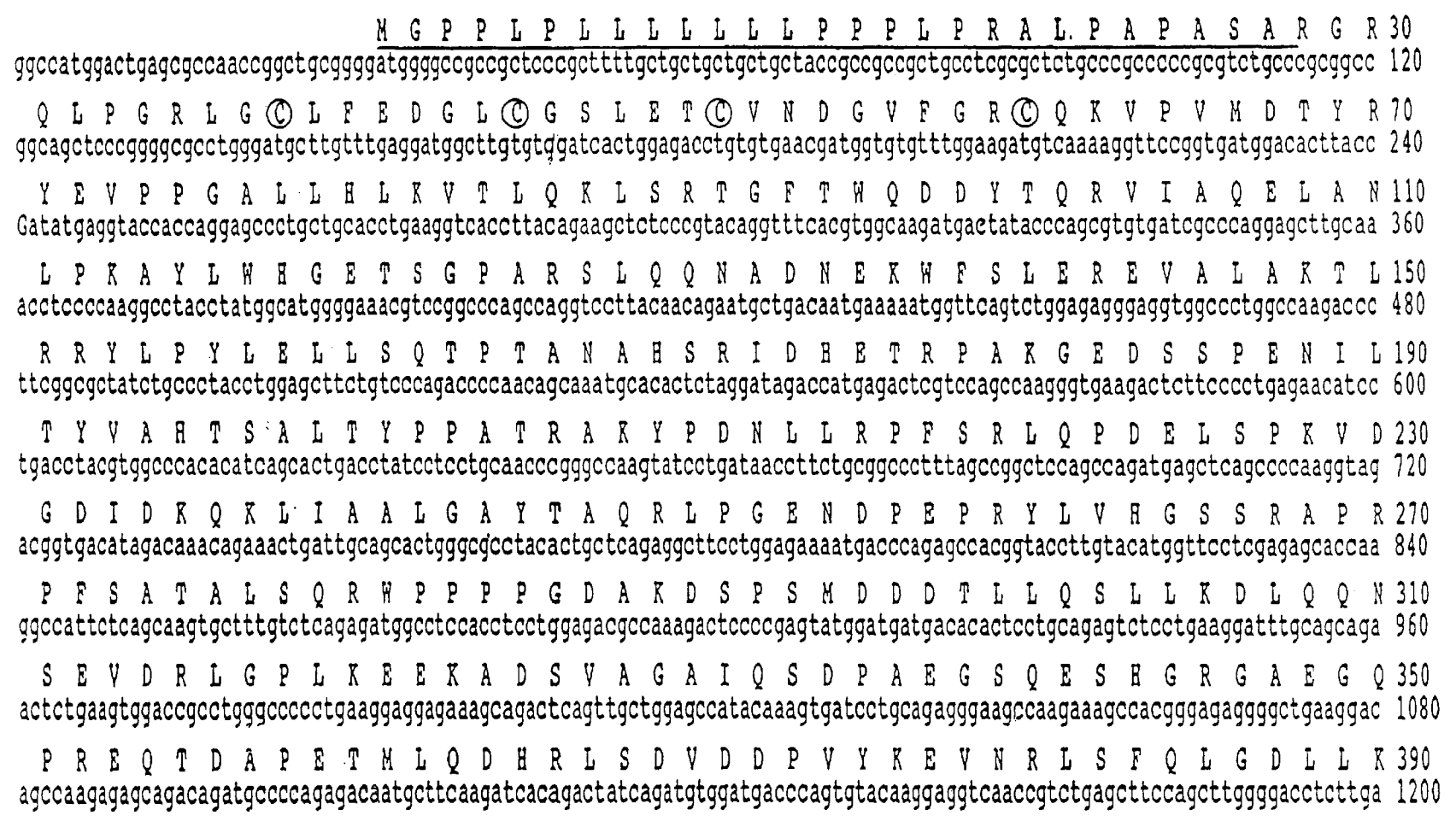
Figure 1B:
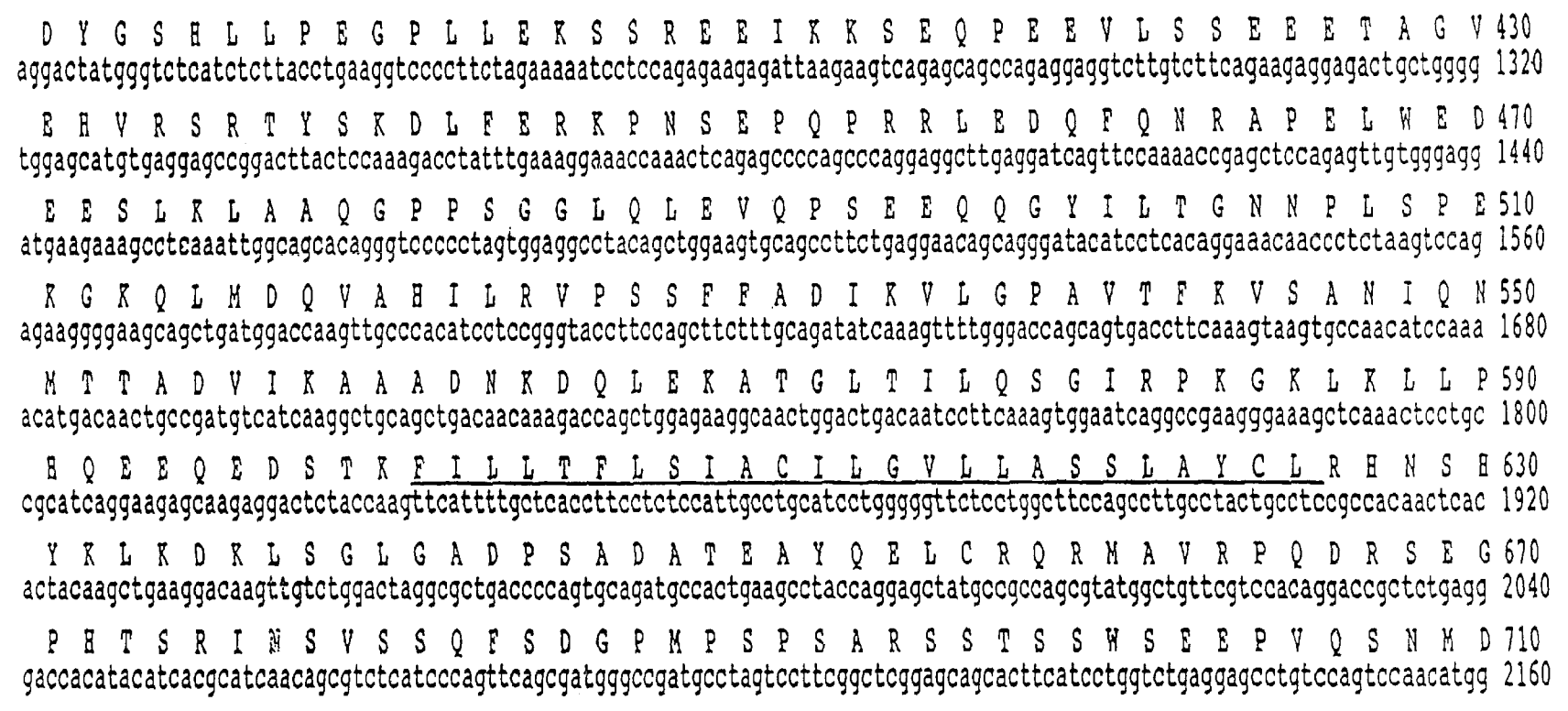
Figure 1C:
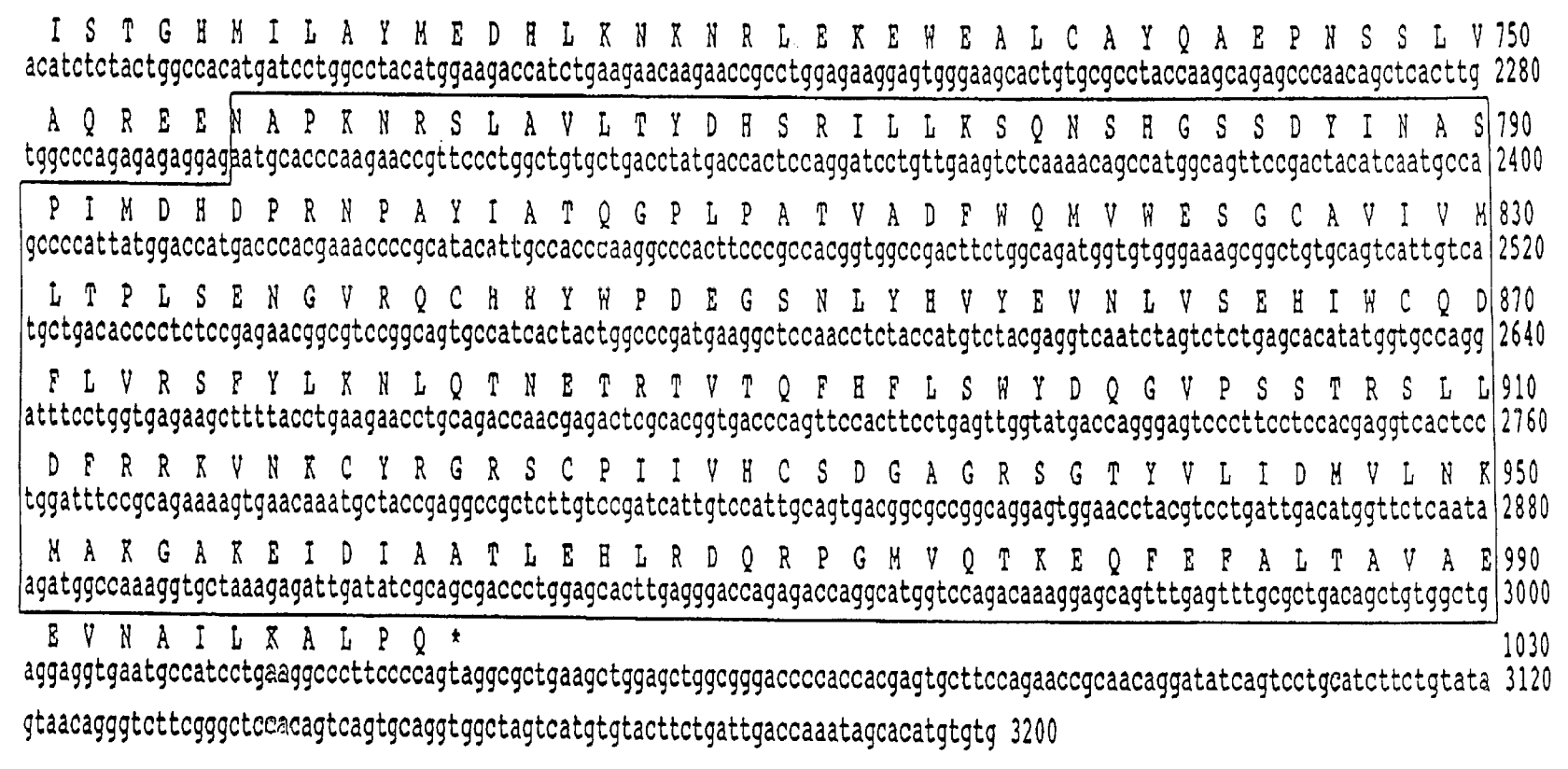

FIGS. 1A-C illustrates the nucleotide sequence of PTP-NP (SEQ ID NO: 1). The deduced amino acid sequence of PTP-NP is shown in single letter code above the nucleotide sequence (SEQ ID NO: 2). The open box indicates the approximate location of the protein tyrosine phosphatase domain. The putative signal peptide and the transmembrane domain are underlined. The cysteine residues in the extracellular domain are circled.

FIG. 2A (SEQ ID NO: 3, 4 and 5) is an alignment of the phosphatase domain SEQ ID NO: 2 and FIG. 2B (SEQ ID NO: 6, 7 and 8)is an alignment of the N-terminal cysteine-conserved region SEQ ID NO: 2 of PTP-NP and other members in this phosphatase subfamily (mIA-2 and *C. elegans* B0244.2 gene product). Black boxes indicate identical amino acid residues in two or more sequences at that position. Gray boxes indicate residues that are conservative changes with respect to the residues in the black boxes. (*) and (+) signs indicate conserved cysteine and leucine residues mentioned in the text, respectively. Sequences were aligned with the PILEUP program and displayed using the PRETTYBOX program in the University of Wisconsin Genetics Computer Group package.

FIGS. 3A and 3B are Northern blot analysis of PTP-NP mRNA in adult tissues. 20 mg of total RNA obtained from various adult tissues were used for the northern analysis. Probes are illustrated in FIG. 1. The blot was first hybridized with the cDNA probe 1 (FIG. 3A), then was stripped, and rehybridized with the cDNA probe 2 (FIG. 3B).

FIG. 3C is an ethidium bromide staining of 28S and 18S ribosomal RNA shown as a control for sample loading.

FIG. 5 (panels A–J) show expression of PTP-NP in early embryos. (A) Whole-mount in situ hybridization of an E9.5 embryo with probe 1, showing PTP-NP expressed in pancreatic primordium. (B) an E9.5 embryo hybridized with probe 2, showing the prominent expression of type 2 PTP-NP in neural tube (detected specifically by probe 2) in addition to the expression of PTP-NP in pancreatic primordium. Sagittal sections (C, G) and transverse sections (D, E) of E10.5 embryos were hybridized with probe 2, showing strong signals in the whole neural tube except in telencephalon. (G) The section was counterstained with neutral red after hybridization, to confirm the absence of staining in the telencephalon. The staining for PTP-NP RNA decreases gradually toward telencephalon. (F) Transverse section of E10.5 embryo hybridized with probe 1, showing moderate signals only in the floor plate and the marginal region of neural tube. (H, I) Transverse sections of E12.5 embryo hybridized with either probe 1 (I) or probe 2 (H), showing same signals in developing nervous system and pancreatic primordium. (J) shows expression of PTP-NP in peripheral neurons. Abbreviations: P, pancreatic primordium; Te, telencephalon; Di, diencephalon; Rh, Rhombencephalon; Nt, neural tube; Fp, floor plate; Drg, dorsal root ganglion; Sg, sympathetic ganglion.

FIG. 6 (panels A–G) show expression of PTP-NP in early pancreatic development. (A) Whole-mount in situ hybridization of an E8.5 embryo treated with antisense probe 1. After hybridization, the stained E8.5 embryos were sectioned either by manual dissection (B) or by cryostat frozen sectioning (C) at the midgut region. Arrowheads show the expression of PTP-NP in the dorsal midgut region. (D–G) E9.5 embryos were sectioned through the region containing the pancreatic primordium, transversely in D and E, or sagittally in F and G. Sections were then hybridized with the antisense probe 1, and double stained with either anti-glucagon (E) or anti-insulin (G) antibodies. E and G are fluorescent micrographs showing the same fields as in D and F, respectively. Arrows illustrate cells expressing both PTP-NP and endocrine markers (glucagon or insulin). Scale bars, 20 mm.

FIG. 7 (panels A–J) show expression of PTP-NP in late pancreatic development. (A–H) Transverse sections of E15.5 embryonic pancreas were hybridized with the antisense probe 1 (A, C, E, G), and double stained with anti-insulin (B), anti-glucagon (D), anti-somatostatin (F), or anti-amylase (H) antibodies, showing PTP-NP is expressed in cells of endocrine lineages, but not in exocrine cells. An adult pancreas section was also hybridized with the same probe (I) and double stained with anti-insulin antibodies (J) to show the expression of PTP-NP in pancreatic islets; some weak staining seen outside the islets is also present in controls with sense strand probe (not shown) and is therefore likely to be nonspecific background. B, D, F, H, and J are fluorescent micrographs showing the same field as in A, C, E, G, and I, respectively. Arrows illustrate cells expressing both PTP-NP and endocrine markers. Scale bars, 20 mm FIG. 8A shows the construction of NP-AP as a soluble receptor affinity reagent. The structure of PTP-NP is illustrated on the left, and the diagram to the right illustrates the structure of the NP-AP soluble receptor affinity reagent which consists of the receptor extracellular domain fused to an alkaline phosphatase tag.

FIG. 8B shows expression of the NP-AP fusion protein and of unfused AP in the supernatants of transfected COS cells. Cells were metabolically labeled with [$^{35}$S] methionine, and then the supernatants were immunoprecipitated with a monoclonal antibody against human placental AP, separated on a 8% polyacrylamide gel, and autoradiographed.

FIG. 9 (panels A–H) shows detection of a candidate PTP-NP ligand with NP-AP fusion protein in pancreatic islets. (A) A frozen section of adult pancreas was treated with supernatant containing NP-AP and then was washed, fixed, and stained for bound AP activity. Arrowheads show specific staining over the islets. (B) When a pancreas section was treated with supernatant containing AP alone, no specific staining was observed. (C–H) Pancreas sections stained with NP-AP (C, E, G) were further double stained with anti-insulin (D), anti-glucagon (F), or anti-somatostatin (H) antibodies, showing the regions which bind NP-AP co-localize with the cells expressing insulin but not with the cells expressing glucagon or somatostatin. C, E, G are fluorescent micrograph showing the same fields as in B, D, F. Scale bars, 20 mm.

DETAILED DESCRIPTION OF THE INVENTION

Figure 1D:
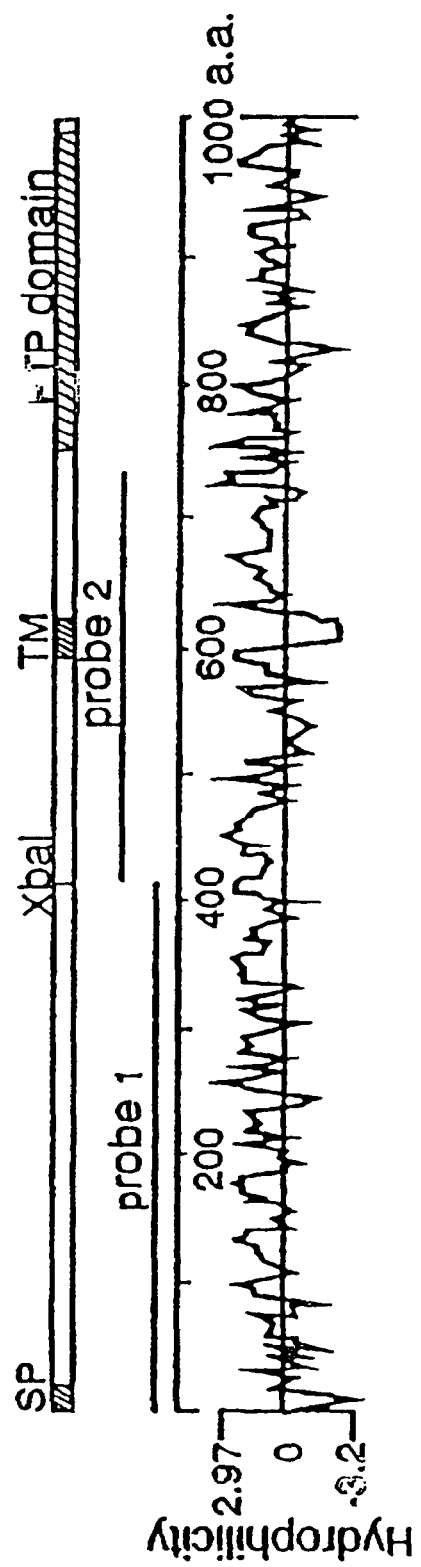
FIG. 1D is a Kyte-Doolittle hydrophilicity plot of predicted PTP-NP polypeptide. A diagram of the predicted structure of PTP-NP is shown above the plot, indicating the secretion signal peptide (SP), the transmembrane domain (TM), and the XbaI restriction site at nucleotide 1238 which separates probe 1 and probe 2 used for Northern and in situ hybridization.

The regulation of protein tyrosine phosphorylation is an important mechanism for developmental control. We describe here a new class of protein tyrosine phosphatases (PTP), called "PTP-NP" (for neural and pancreatic) receptors. The sequence of an exemplary PTP-NP gene SEQ ID NO: 1 indicates it encodes a receptor type PTP SEQ ID NO: 2 with a single tyrosine phosphatase domain. Comparison of PTP-NP with the other known PTPs reveals a cysteine-conserved motif in the extracellular domain and, together with their homology in the phosphatase domain, this defines a new subclass of receptor type PTPs. One other member of this class of PTPs, IA-2, was identified from an insulinoma cell line and, like PTP-NP, was found to be expressed in adult brain and pancreas (Lan et al., 1994; Lu et al., 1994). PTP-NP shows close homology with the murine mIA-2 molecule in the whole phosphatase domain but only distant homology in the extracellular domain, which suggests these two PTPs likely bind different ligands but may share certain downstream target molecules. These two genes are also related to the C. elegans B0244.2 gene, identified from a genome project, implying the possibility of conservation of the functions of this subfamily during evolution and suggesting the C. elegans gene may represent the prototype of PTP-NP and IA-2.

As described in further detail in the appended examples, we initially identified PTP-NP in a screen for potential cell-cell signaling molecules involved in early development of the nervous system. Consistent with our initial identification of PTP-NP in RNA from embryonic neural tube, PTP-NP mRNA was found to be expressed highly in neural tube from early stages of neurulation, and was also found to be expressed in adult brain. To analyze the potential role of PTP-NP in neural development further, we used the P19 mouse embryonal carcinoma cell line, a well characterized in vitro model system for neuronal differentiation. During P19 neuronal differentiation, two different types of PTP-NP transcripts were detected and were observed to be under different temporal regulation. Type 1 PTP-NP, containing the extracellular domain described in SEQ ID NO: 2, is expressed at relatively late stages, when the induced P19 cells begin to resemble neurons morphologically, and express markers of late neuronal differentiation. In contrast, the RNA expression of type 2 PTP-NP, which lacks the extracellular domain of type 1, shows a rapid induction within 24 hours of retenoic acid treatment. This expression of the type 2 RNA is transient, and is down regulated dramatically as the type 1 RNA is subsequently expressed at lower levels. The early expression of type 2 PTP-NP in P19 induction appears even before that of the proneural gene MASH-1, implicating its involvement at very early stages of neuronal cell fate determination.

These observations from P19 cells are consistent with the expression patterns of type 1 and type 2 PTP-NP in early embryos. At early stages of neural tube development type 2 PTP-NP is expressed strongly in the neural tube. Expression of type 1 PTP-NP begins to appear later, by E10.5 in the marginal zone of the neural tube and the floor plate, where neuronal differentiation is relatively advanced, and by E12.5 it becomes a major form of PTP-NP expressed in the neural tube. Taken together with the P19 experiments, these results indicate that type 2 PTP-NP is induced strongly and transiently in early neurogenesis, and type 1 PTP-NP is expressed more weakly at later stages of neuronal differentiation.

Despite the importance of pancreatic endocrine cells in physiology and disease, little is known at the molecular level about the developmental control of the pancreas, and no cell-cell signaling molecules have yet been identified as specific regulators of pancreatic development. We were therefore intrigued to find that, in addition to its neural expression, PTP-NP appeared specifically in one other tissue, including the pancreas. Moreover, at early organogenesis, as the pancreas begins to form, prominent expression of the full-length PTP-NP type 1 RNA is confined specifically to the pancreas.

At the site of pancreatic development, the expression of PTP-NP was first observed as early as E8.5, in the endodermal layer of the dorsal region of the gut while it was still open to the yolk sac. The site within the endoderm that gives rise to the pancreatic rudiment has previously been identified from morphological descriptions of early pancreatic development and from in vitro explant culture experiments (Wessells and Cohen, 1967). In these studies, it was found that pancreatic tissue could be cultured from a specific region of the gut from 10- and 11-somite embryos, was formed less efficiently when the tissue was obtained from 7–9 somite embryos, and was not produced from earlier embryos. The site of PTP-NP expression identified in our experiments appears to be localized to the region within the endoderm that becomes committed to form the pancreas, and moreover the time of appearance of PTP-NP RNA appears to be similar to the time of initial pancreatic commitment.

Later, by E9.5 and after, as the pancreatic rudiment becomes morphologically distinguishable, cells containing PTP-NP appeared to be located only within the pancreatic rudiment, and not in adjacent areas of the gut. The temporal and spatial expression of PTP-NP in developing pancreas is somewhat similar to that of STF-1, a nuclear factor that is the earliest known marker for pancreatic development (described supra). However, unlike STF-1, PTP-NP is not expressed in the adjacent duodenum, making it a more specific marker at the site of the early developing pancreas. PTP-NP type 1 is thus noteworthy as a particularly early and specific marker of pancreatic development.

Within the developing pancreas, PTP-NP expression is not seen in all cells. To determine which lineages might express PTP-NP, we performed double-labeling experiments with antibodies against hormonal markers, and against amylase, a marker for exocrine cells. By E15.5 distinct types of pancreatic endocrine cell have appeared each expressing a single hormonal marker (Slack, (1995) Development 121:1569–1580). At this stage we found that, of cells stained with any of the four hormonal markers insulin, glucagon, somatostatin or pancreatic polypeptide, all were positive for PTP-NP expression. On the other hand, amylase-positive cells did not express PTP-NP. Similarly, in adult pancreas, PTP-NP is found in the islets. These results indicate PTP-NP expression is specific for all endocrine lineages, and is not found in exocrine cells.

At earlier stages of pancreatic development the endocrine markers insulin and glucagon were previously reported to be co-expressed in the same cells in the pancreatic rudiment and, although not formally proven, it is believed that these hormone-expressing cells are likely to be precursors of the endocrine cells (Teitelman et al., (1993) Development 118:1031–1039; Slack, supra). At E9.5, the earliest stage when these two hormonal markers 30 have been detected by antibodies, we found that mRNA for PTP-NP is expressed in all the insulin- or glucagon-producing cells. An additional population of cells was found to express PTP-NP RNA but did not stain obviously for the hormonal markers. Those additional cells could represent an additional population of endocrine progenitor cells. In particular, in view of the very early developmental onset of PTP-NP expression, it is plausible that this population could represent stem cells or other undifferentiated progenitors that have not yet begun to produce hormonal markers.

The identification over the last few years of a large number of orphan receptor tyrosine kinases and phosphatases implies the existence of hitherto unidentified ligands that could be important regulators of developmental processes. To test for the possible existence of a ligand for PTP-NP we used a technique we have described previously to identify the ligands of other orphan receptors, making a soluble fusion probe consisting of the extracellular domain of the receptor joined to alkaline phosphatase. This NP-AP fusion protein binds strongly to pancreatic islets, identifying a candidate ligand, and suggesting a ligand-receptor signaling pathway that could be involved in control of pancreatic endocrine cells. Since both receptor and ligand are apparently associated with pancreatic endocrine cells, they may mediate local control, acting within the pancreas. This possibility is particularly intriguing, considering that there does not appear to be an efficient systemic control mechanism that can, for example, promote regeneration of endocrine cells in diabetic states. Instead, pancreatic endocrine cell number and regeneration is believed to be primarily under the local control of factors acting within the pancreas (Slack, supra). Further characterization of the candidate ligand(s) and the PTP-NP receptor will help to understand the early development of the pancreas, according to the present invention provides a means for developing therapeutics agents that modulate the behavior of pancreatic endocrine cells in the context of normal development or disease states.

Accordingly, certain aspects of the present invention relate to nucleic acids encoding PTP-NP polypeptides, the PTP-NP polypeptides themselves (including various fragments), antibodies immunoreactive with PTP-NP proteins, and preparations of such compositions. Moreover, the present invention provides diagnostic and therapeutic assays and reagents for detecting and treating disorders involving, for example, aberrant expression (or loss thereof) of PTP-NP, ligands of PTP-NP or intracellular signal transducers thereof.

In addition, drug discovery assays are provided for identifying agents which can modulate the biological function of PTP-NP proteins, such as by altering the binding of PTP-NP molecules to extracellular/matrix factors or the ability of the phosphatase activity of the receptor to modify intracellular substrates involved in signaling from the receptor. Such agents can be useful therapeutically to alter the growth, maintenance and/or differentiation of a cell, particularly a pancreatic or neuronal cell. Other aspects of the invention are described below or will be apparent to those skilled in the art in light of the present disclosure.

For convenience, certain terms employed in the specification, examples, and appended claims are collected here.

The term "PTP-NP" or "NP" polypeptide refers to a family of polypeptides characterized at least in part by being identical or sharing a degree of sequence homology with all or a portion of the receptor phosphatase represented in SEQ ID NO: 2. The PTP-NP polypeptides can be cloned or purified from any of a number of eukaryotic organisms, especially vertebrates, and particularly mammals. Moreover, other PTP-NP polypeptides can be generated according to the present invention, which polypeptides do not ordinarily exist in nature, but rather are generated by non-natural mutagenic techniques.

As described in the appended examples, a number of features of the PTP-NP protein have been observed upon inspection. In particular, we have noted that four cysteine residues are apparently conserved with approximately the same characteristic spacing relative to certain other receptor phosphatase. This conserved "motif" containing these four cysteines, referred to herein as a "$Cys_4$ motif", may represent a fragment which retains or is critical to certain biological activities of the full length (mature) protein, such as, for example, the ability to bind a ligand. In exemplary PTP-NP polypeptides, the $Cys_4$ motif is represented by general formula CXXXXXXCXXXXXCXXXXXXXXC, e.g., corresponding to residues 38–60 of SEQ ID NO: 9. Those skilled in the art, in light of the present invention, will be able to easily ascertain the equivalent $Cys_4$ motifs in other PTP-NP polypeptides.

Furthermore, we have observed that a "transmembrane domain" within the receptor, separating an "extracellular domain" and an "intracellular domain". See FIG. 1A. The transmembrane domain corresponds to residues 601–625 of SEQ ID NO: 2, while the extracellular domain corresponds to residues 1–600 and the intracellular domain corresponds to residues 626–1001, with analogous domains for other PTP-NP polypeptides readily ascertainable by comparison with these sequences. The intracellular domain includes a protein tyrosine phosphatase domain, e.g., corresponding approximately to residues 756–990 of SEQ ID NO: 2.

Finally, co- and post-translational modifications of PTP-NP polypeptides have been observed. A "mature" PTP-NP polypeptide refers to an PTP-NP polypeptide which lacks a signal sequence (e.g., a peptidyl portion which causes extracellular secretion of at least a portion of the protein). An exemplary mature PTP-NP polypeptide is represented by residues Arg-28 to Gln-1001.

A "glycosylated" PTP-NP polypeptide is an PTP-NP polypeptide having a covalent linkage with a glycosyl group (e.g. a derivatized with a carbohydrate). For instance, the PTP-NP protein can be glycosylated on an existing residue, or can be mutated to preclude carbohydrate attachment, or can be mutated to provide new glycosylation sites, such as for N-linked or O-linked glycosylation.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding of a PTP-NP polypeptide, including both exon and (optionally) intron sequences. A "recombinant gene" refers to nucleic acid encoding a PTP-NP polypeptide and comprising PTP-NP-encoding exon sequences, though it may optionally include intron sequences which are derived from, for example, a chromosomal PTP-NP gene or from an unrelated chromosomal gene. Exemplary recombinant genes encoding the subject PTP-NP polypeptide are represented in the appended Sequence Listing.

The term "intron" refers to a DNA sequence present in a given PTP-NP gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a PTP-NP polypeptide or, where anti-sense expression occurs from the transferred gene, the expression of a naturally-occurring form of the PTP-NP protein is disrupted.

As used herein, the term "specifically hybridizes" refers to the ability of a nucleic acid probe/primer of the invention to hybridize to at least 15 consecutive nucleotides of a PTP-NP gene, such as a PTP-NP sequence designated in SEQ ID NO: 1, or a sequence complementary thereto, or naturally occurring mutants thereof, such that it has less than 15%, preferably less than 10%, and more preferably less than 5% background hybridization to a cellular nucleic acid (e.g., mRNA or genomic DNA) encoding a protein other than a PTP-NP protein, as defined herein. In preferred embodiments, the oligonucleotide probe specifically detects only a PTP-NP gene, e.g., it does not substantially hybridize to transcripts for other phosphatase homologs, such as B0244.2, IA, DPTP99A, DPTP10D or DLAR.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant PTP-NP gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of PTP-NP genes.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of neuronal or hematopoietic origin. The term also covers so-called "leaky" promoters, which regulate expression of a selected DNA primarily in one tissue, but can cause at least low level expression in other tissues as well.

As used herein, a "transgenic animal" is any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In an exemplary transgenic animal, the transgene causes cells to express a recombinant form of a PTP-NP protein, e.g. either agonistic or antagonistic forms. However, transgenic animals in which the recombinant PTP-NP gene is silent are also contemplated, as for example, the FLP or CRE recombinase dependent constructs described below. Moreover, "transgenic animal"also includes those recombinant animals in which gene disruption of one or more PTP-NP genes is caused by human intervention, including both recombination and antisense techniques.

The "non-human animals" of the invention include vertebrates such as rodents, non-human primates, livestock, avian species, amphibians, reptiles, etc. The term "chimeric animal" is used herein to refer to animals in which the recombinant gene is found, or in which the recombinant is expressed in some but not all cells of the animal. The term "tissue-specific chimeric animal" indicates that a recombinant PTP-NP genes is present and/or expressed or disrupted in some tissues but not others.

As used herein, the term "transgene" means a nucleic acid sequence (encoding, e.g., a PTP-NP polypeptide, or pending an antisense transcript thereto), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a PTP-NP polypeptide" may thus refer to one or more genes within a particular individual. Moreover, certain differences in nucleotide sequences may exist between individuals of the same species, which are called alleles. Such allelic differences may or may not result in differences in amino acid sequence of the encoded polypeptide yet still encode a protein with the same biological activity.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40 percent identity, though preferably less than 25 percent identity, with a PTP-NP sequence of the present invention.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding a PTP-NP polypeptide with a second amino acid sequence defining a domain (e.g. polypeptide portion) foreign to and not substantially homologous with any domain of a PTP-NP protein. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-NP-Y, wherein NP represents a portion of the fusion protein which is derived from a PTP-NP protein, and X and Y are, independently, absent or represent amino acid sequences which are not related to a PTP-NP sequences in an organism.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding a PTP-NP polypeptide preferably includes no more than 10 kilobases (kb) of nucleic acid sequence which naturally immediately flanks the PTP-NP gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As described below, one aspect of the invention pertains to isolated nucleic acids comprising nucleotide sequences encoding PTP-NP polypeptides, and/or equivalents of such nucleic acids. The term nucleic acid as used herein is intended to include fragments as equivalents. The term equivalent is understood to include nucleotide sequences encoding functionally equivalent PTP-NP polypeptides or functionally equivalent peptides having an activity of a PTP-NP protein such as described herein. Equivalent nucleotide sequences will include sequences that differ by one or more nucleotide substitutions, additions or deletions, such as allelic variants; and will, therefore, include sequences that differ from the nucleotide sequence of the PTP-NP cDNA sequence shown in SEQ ID NO: 1 due to the degeneracy of the genetic code. Equivalents will also include nucleotide sequences that hybridize under stringent conditions (i.e., equivalent to about 20–27° C. below the melting temperature ($T_m$) of the DNA duplex formed in about 1 M salt) to the nucleotide sequences represented in SEQ ID NO: 1. In one embodiment, equivalents will further include nucleic acid sequences derived from and evolutionarily related to, a nucleotide sequences shown in SEQ ID NO: 1.

Moreover, it will be generally appreciated that, under certain circumstances, it may be advantageous to provide homologs of a PTP-NP polypeptide which function in a limited capacity as one of either a PTP-NP agonist (mimetic) or a PTP-NP antagonist, in order to promote or inhibit only a subset of the biological activities of the naturally-occurring form of the protein. Thus, specific biological effects can be elicited by treatment with a homolog of limited function. For example, truncated forms of the receptor, e.g., soluble fragments of the extracellular domain, can be provided to competitively inhibit ligand binding to the receptor. Likewise, mutants having altered enzyme activity profiles, e.g., altered $k_{cat}$ or $k_m$ or constitutively active mutants, can be provided.

Homologs of the subject PTP-NP protein can be generated by mutagenesis, such as by discrete point mutation(s), or by truncation. For instance, mutation can give rise to homologs which retain substantially the same, or merely a subset, of the biological activity of the PTP-NP polypeptide from which it was derived. Alternatively, antagonistic forms of the protein can be generated which are able to inhibit the function of the naturally occurring form of the protein, such as by competitively binding to a PTP-NP substrate or PTP-NP associated protein, as for example competing with wild-type PTP-NP in the binding of an extracellular ligand, or binding to an intracellular protein such as a substrate of the PTP activity. Thus, the PTP-NP protein and homologs thereof provided by the subject invention may be either positive or negative regulators of cell growth, death and/or differentiation.

In general, polypeptides referred to herein as having an activity of a PTP-NP protein (e.g., are "bioactive") are defined as polypeptides which include an amino acid sequence corresponding (e.g., identical or homologous) to all or a portion of the amino acid sequences of the PTP-NP protein shown in SEQ ID NO: 2, and which mimic or antagonize all or a portion of the biological/biochemical activities of a naturally occurring PTP-NP protein. Examples of such biological activity include: the ability to dephosphorylate a phosphotyrosine residue; hydrolyze a phosphatase substrate such as p-nitrophenylphosphate; bind to a ligand expressed on pancreatic β cells. The bioactivity of certain embodiments of the PTP-NP protein can be characterized in terms of an ability to promote differentiation and/or maintenance of pancreatic and neural cells and tissue.

Other biological activities of the subject PTP-NP proteins are described herein or will be reasonably apparent to those skilled in the art. According to the present invention, a polypeptide has biological activity if it is a specific agonist or antagonist of a naturally-occurring form of a PTP-NP protein.

Preferred nucleic acids encode a PTP-NP polypeptide comprising an amino acid sequence at least 60%, 70% or 80% homologous, more preferably at least 85% homologous and most preferably at least 95% homologous with an amino acid sequence of a naturally occurring PTP-NP protein, e.g., such as represented in SEQ ID NO: 2. Nucleic acids which encode polypeptides at least about 98–99% homology with an amino acid sequence represented in SEQ ID NO: 2 are of course also within the scope of the invention, as are nucleic acids identical in sequence with the enumerated PTP-NP sequence of the sequence listing. In one embodiment, the nucleic acid is a cDNA encoding a polypeptide having at least one activity of the subject PTP-NP polypeptide.

In certain preferred embodiments, the invention features a purified or recombinant PTP-NP polypeptide having peptide chain with a molecular weight in the range of 105 kd to 115 kd, even more preferably in the range of 105 kd to 110 kd (for a full-length mature protein). It will be understood that certain post-translational modifications, e.g., glycosylation, phosphorylation and the like, can increase the apparent molecular weight of the PTP-NP protein relative to the unmodified polypeptide chain, and cleavage of certain sequences, such as pro-sequences, can likewise decrease the apparent molecular weight. Other preferred PTP-NP polypeptides include a mature, extracellular fragment (soluble) of the receptor, e.g., corresponding to residues 28–600 of SEQ ID NO: 2, e.g., having a molecular weight of about 63.7 kd. In a preferred embodiments, the nucleic acid encodes a PTP-NP polypeptide which includes the $Cys_4$ motif. Yet another preferred PTP-NP polypeptide includes an intracellular domain, e.g., corresponding to residues 626–1001 of SEQ ID NO: 2, e.g., having a molecular weight of about 42.4 kd. Still another preferred PTP-NP polypeptide includes a phosphatase domain, e.g., corresponding to residues 756–990 of SEQ ID No 2, e.g., having a molecular weight of about 26.7 kd. By a "molecular weight of about" it is meant with in about ±5 kd.

Another aspect of the invention provides a nucleic acid which hybridizes under high or low stringency conditions to the nucleic acid represented by SEQ ID NO: 1. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Nucleic acids, having a sequence that differs from the nucleotide sequences shown in SEQ ID NO: 1 due to degeneracy in the genetic code are also within the scope of the invention. Such nucleic acids encode functionally equivalent peptides (i.e., a peptide having a biological activity of a PTP-NP polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a PTP-NP polypeptide. However, it is expected that DNA sequence polymorphisms that do lead to changes in the amino acid sequences of the subject PTP-NP polypeptides will exist among, for example, humans. One skilled in the art will appreciate that these variations in one or more nucleotides (up to about 3–5% of the nucleotides) of the nucleic acids encoding polypeptides having an activity of a PTP-NP polypeptide may exist among individuals of a given species due to natural allelic variation.

As used herein, a PTP-NP gene fragment refers to a nucleic acid having fewer nucleotides than the nucleotide sequence encoding the entire mature form of a PTP-NP protein yet which (preferably) encodes a polypeptide which retains some biological activity of the full length protein. Fragment sizes contemplated by the present invention include, for example, 5, 10, 25, 50, 75, 100, or 200 amino acids in length. In a preferred embodiment of a truncated receptor, the polypeptide will include all or a sufficient portion of the extracellular domain to bind to a PTP-NP ligand, and preferably includes the $Cys_4$ motif. In another phosphatase domain of the cytosolic portion of the protein. In either embodiment, the PTP-NP polypeptide can also include the transmembrane domain, particularly where membrane localized (instead of soluble) fragments of the PTP-NP protein are desired.

As indicated by the examples set out below, PTP-NP protein-encoding nucleic acids can be obtained from mRNA present in cells of metazoan organisms. It should also be possible to obtain nucleic acids encoding PTP-NP polypeptides of the present invention from genomic DNA from both adults and embryos. For example, a gene encoding a PTP-NP protein can be cloned from either a cDNA or a genomic library in accordance with protocols described herein, as well as those generally known to persons skilled in the art. A cDNA encoding a PTP-NP protein can be obtained by isolating total mRNA from a cell, such as a mammalian cell, e.g. a human cell, as desired. Double stranded cDNAs can be prepared from the total mRNA, and subsequently inserted into a suitable plasmid or bacteriophage vector using any one of a number of known techniques. The gene encoding a PTP-NP protein can also be cloned using established polymerase chain reaction techniques in accordance with the nucleotide sequence information provided by the invention. The nucleic acid of the invention can be DNA or RNA. A preferred nucleic acid is a cDNA including a nucleotide sequence represented by one of SEQ ID NO: 1.

Another aspect of the invention relates to the use of the isolated nucleic acid in "antisense" therapy. As used herein, "antisense" therapy refers to administration or in situ generation of oligonucleotide probes or their derivatives which specifically hybridize (e.g. binds) under cellular conditions, with the cellular mRNA and/or genomic DNA encoding a subject PTP-NP protein so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a PTP-NP protein. Alternatively, the antisense construct is an oligonucleotide probe which is generated ex vivo and which, when introduced into the cell causes inhibition of expression by hybridizing with the mRNA and/or genomic sequences of a PTP-NP gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775), or peptide nucleic acids (PNAs). Additionally, general approaches to constructing oligomers useful in antisense therapy have been reviewed, for example, by Van der Krol et al. (1988) Biotechniques 6:958–976; and Stein et al. (1988) Cancer Res 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of routes of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind. Such diagnostic tests are described in further detail below.

Likewise, the antisense constructs of the present invention, by antagonizing the normal biological activity of a PTP-NP protein, e.g., by reducing the level of its expression, can be used in the manipulation of tissue, e.g. tissue maintenance, differentiation or growth, both in vivo and ex vivo.

Furthermore, the anti-sense techniques (e.g. microinjection of antisense molecules, or transfection with plasmids whose transcripts are anti-sense with regard to a PTP-NP mRNA or gene sequence) can be used to investigate the role of PTP-NP in developmental events, as well as the normal cellular function of PTP-NP in adult tissue. Such techniques can be utilized in cell culture, but can also be used in the creation of transgenic animals (described infra).

This invention also provides expression vectors containing a nucleic acid encoding a PTP-NP polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of the subject PTP-NP proteins. Accordingly, the term transcriptional regulatory sequence includes promoters, enhancers and other expression control elements. Such regulatory sequences are described in Goeddel; Gene Expression Technology: Methods in Enzymology 185, Academic Press, San Diego, Calif. (1990). For instance, any of a wide variety of expression control sequences, sequences that control the expression of a DNA sequence when operatively linked to it, may be used in these vectors to express DNA sequences encoding PTP-NP polypeptides of this invention. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed.

Moreover, the vector's copy number, the ability to control that copy number and the expression of any other proteins encoded by the vector, such as antibiotic markers, should also be considered. In one embodiment, the expression vector includes a recombinant gene encoding a polypeptide having an agonistic activity of a subject PTP-NP polypeptide, or alternatively, encoding a polypeptide which is an antagonistic form of the PTP-NP protein, such as a soluble truncated form including the extracellular domain, or a truncated form including the intracellular domain. Such expression vectors can be used to transfect cells and thereby produce polypeptides, including fusion proteins, encoded by nucleic acids as described herein.

Moreover, the gene constructs of the present invention can also be used as a part of a gene therapy protocol to deliver nucleic acids, e.g., encoding either an agonistic or antagonistic form of a subject PTP-NP proteins or an antisense molecule described above. Thus, another aspect of the invention features expression vectors for in vivo or in vitro transfection and expression of a PTP-NP polypeptide or antisense molecule in particular cell types so as to reconstitute the function of, or alternatively, abrogate all or a portion of the biological function of PTP-NP-induced transcription in a tissue in which the naturally-occurring form of the protein is misexpressed (or has been disrupted); or to deliver a form of the protein which alters maintenance or differentiation of tissue, or which inhibits neoplastic or hyperplastic proliferation.

Expression constructs of the subject PTP-NP polypeptides, as well as antisense constructs, may be administered in any biologically effective carrier, e.g. any formulation or composition capable of effectively delivering the recombinant gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of PTP-NP expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA encoding the particular PTP-NP polypeptide desired. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid. Retrovirus vectors, adenovirus vectors and adeno-associated virus vectors are exemplary recombinant gene delivery system for the transfer of exogenous genes in vivo, particularly into humans. These vectors provide efficient delivery of genes into cells, and the transferred nucleic acids are stably integrated into the chromosomal DNA of the host.

In addition to viral transfer methods, such as those illustrated above, non-viral methods can also be employed to cause expression of a subject PTP-NP polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject PTP-NP polypeptide gene by the targeted cell. Exemplary gene delivery systems of this type include liposomal derived systems, polylysine conjugates, and artificial viral envelopes.

In clinical settings, the gene delivery systems for the therapeutic PTP-NP gene can be introduced into a patient-animal by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057). A PTP-NP gene can be delivered in a gene therapy construct by electroporation using techniques described, for example, by Dev et al. ((1994) Cancer Treat Rev 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

Another aspect of the present invention concerns recombinant forms of the PTP-NP proteins. Recombinant polypeptides preferred by the present invention, in addition to native PTP-NP proteins, are at least 60% or 70% homologous, more preferably at least 80% homologous and most preferably at least 85% homologous with an amino acid sequence represented by SEQ ID NO: 2. Polypeptides which possess an activity of a PTP-NP protein (i.e. either agonistic or antagonistic), and which are at least 90%, more preferably at least 95%, and most preferably at least about 98–99% homologous with SEQ ID NO: 2 are also within the scope of the invention. Such polypeptides, as described above, include various truncated forms of the protein.

The term "recombinant PTP-NP polypeptide" refers to a polypeptide which is produced by recombinant DNA techniques, wherein generally, DNA encoding a PTP-NP polypeptide is inserted into a suitable expression vector which is in turn used to transform a host cell to produce the heterologous protein. Moreover, the phrase "derived from", with respect to a recombinant PTP-NP gene, is meant to include within the meaning of "recombinant protein" those proteins having an amino acid sequence of a native PTP-NP protein, or an amino acid sequence similar thereto which is generated by mutations including substitutions and deletions (including truncation) of a naturally occurring form of the protein.

The present invention further pertains to recombinant forms of the subject PTP-NP polypeptides which are encoded by genes derived from a mammal (e.g. a human), reptile or amphibian and which have amino acid sequences evolutionarily related to the PTP-NP protein represented in SEQ ID NO: 2. Such recombinant PTP-NP polypeptides preferably are capable of functioning in one of either role of an agonist or antagonist of at least one biological activity of a wild-type ("authentic") PTP-NP protein of the appended sequence listing. The term "evolutionarily related to", with respect to amino acid sequences of PTP-NP proteins, refers to both polypeptides having amino acid sequences which have arisen naturally, and also to mutational variants of PTP-NP polypeptides which are derived, for example, by combinatorial mutagenesis.

The present invention also provides methods of producing the subject PTP-NP polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant PTP-NP polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant PTP-NP polypeptide is a fusion protein containing a domain which facilitates its purification, such as GST fusion protein or poly(His) fusion protein.

This invention also pertains to a host cell transfected to express recombinant forms of the subject PTP-NP polypeptides. The host cell may be any eukaryotic or prokaryotic cell. Thus, a nucleotide sequence derived from the cloning of PTP-NP proteins, encoding all or a selected portion of a full-length protein, can be used to produce a recombinant form of a PTP-NP polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. cdc25, PTP phosphatases, and a wide range of receptors, and the like. Similar procedures, or modifications thereof, can be employed to prepare recombinant PTP-NP polypeptides by microbial means or tissue-culture technology in accord with the subject invention.

The recombinant PTP-NP genes can be produced by ligating nucleic acid encoding an PTP-NP protein, or a portion thereof, into a vector suitable for expression in either prokaryotic cells, eukaryotic cells, or both. Expression vectors for production of recombinant forms of the subject PTP-NP polypeptides include plasmids and other vectors. For instance, suitable vectors for the expression of a PTP-NP polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in Experimental Manipulation of Gene Expression, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, a PTP-NP polypeptide is produced recombinantly utilizing an expression vector generated by sub-cloning the coding sequence of a PTP-NP gene represented in SEQ ID NO: 1.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

In some instances, it may be desirable to express the recombinant PTP-NP polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a PTP-NP protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) J. Bacteriol. 169:751–757) and *Salmonella typhimurium* and its in vitro activity has been demonstrated on recombinant proteins (Miller et al. (1987) PNAS 84:2718–1722). Therefore, removal of an N-terminal methionine, if desired, can be achieved either in vivo by expressing PTP-NP-derived polypeptides in a host which produces MAP (e.g., *E. coli* or CM89 or *S. cerevisiae*), or in vitro by use of purified MAP (e.g., procedure of Miller et al., supra).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of a PTP-NP protein. For example, the VP6 capsid protein of rotavirus can be used as an immunologic carrier protein for portions of the PTP-NP polypeptide, either in the monomeric form or in the form of a viral particle. The nucleic acid sequences corresponding to the portion of a subject PTP-NP protein to which antibodies are to be raised can be incorporated into a fusion gene construct which includes coding sequences for a late vaccinia virus structural protein to produce a set of recombinant viruses expressing fusion proteins comprising PTP-NP epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a PTP-NP protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) J. Virol. 66:2).

The Multiple Antigen Peptide system for peptide-based immunization can also be utilized to generate an immunogen, wherein a desired portion of a PTP-NP polypeptide is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of PTP-NP proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the PTP-NP polypeptides of the present invention, particularly truncated forms of the PTP-NP protein. For example, PTP-NP polypeptides can be generated as glutathione-S-transferase (GST-fusion) proteins. Such GST-fusion proteins can enable easy purification of the PTP-NP polypeptide, as for example by the use of glutathione-derivatized matrices (see, for example, Current Protocols in Molecular Biology, eds. Ausubel et al. (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) J. Chromatography 411:177; and Janknecht et al. PNAS 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al. John Wiley & Sons: 1992).

The PTP-NP polypeptides may also be chemically modified to create PTP-NP derivatives by forming covalent or aggregate conjugates with other chemical moieties, such as glycosyl groups, lipids, phosphate, acetyl groups and the like. Covalent derivatives of PTP-NP proteins can be prepared by linking the chemical moieties to functional groups on amino acid sidechains of the protein or at the N-terminus or at the C-terminus of the polypeptide.

As appropriate, formulations of multimeric PTP-NP receptors are also provided. The multimers of the soluble forms of the subject PTP-NP receptors may be produced according to the methods known in the art. In one embodiment, the PTP-NP multimers are cross-linked chemically by using known methods which will result in the formation of either dimers or higher multimers of the soluble forms of the PTP-NP receptor. Another way of producing the multimers of the soluble forms of the PTP-NP receptor is by recombinant techniques, e.g., by inclusion of hinge regions. This linker can facilitate enhanced flexibility of the chimeric protein allowing the various PTP-NP monomeric subunits to freely and (optionally) simultaneously interact with a PTP-NP ligand by reducing steric hindrance between the two fragments, as well as allowing appropriate folding of each portion to occur. The linker can be of natural origin, such as a sequence determined to exist in random coil between two domains of a protein. Alternatively, the linker can be of synthetic origin. For instance, the sequence $(Gly_4Ser)_3$ can be used as a synthetic unstructured linker. Linkers of this type are described in Huston et al. (1988) PNAS 85:4879; and U.S. Pat. Nos. 5,091,513 and 5,258,498. Naturally occurring unstructured linkers of human origin are preferred as they reduce the risk of immunogenicity.

Each multimer comprises two or more monomers, each comprising the soluble form of a PTP-NP receptor or a salt or functional derivative thereof. The upper limit for the number of monomers in a multimer is not important and liposomes having many such monomers thereon may be used. Such multimers preferably have 2–5 monomers and more preferably 2 or 3.

The present invention also makes available isolated PTP-NP polypeptides which are isolated from, or otherwise substantially free of other cellular proteins, especially other signal transduction factors membrane-localized proteins which may normally be associated with the PTP-NP polypeptide. The term "substantially free of other cellular proteins" (also referred to herein as "contaminating proteins") or "substantially pure or purified preparations" are defined as encompassing preparations of PTP-NP polypeptides having less than 20% (by dry weight) contaminating protein, and preferably having less than 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified PTP-NP preparations will lack any contaminating proteins from the same animal from that PTP-NP is normally produced, as can be accomplished by recombinant expression of, for example, a mammalian PTP-NP protein in a yeast or bacterial cell.

As described above for recombinant polypeptides, isolated PTP-NP polypeptides can include all or a portion of an amino acid sequences corresponding to a PTP-NP polypeptide represented in SEQ ID NO: 2 or homologous sequences thereto.

Isolated peptidyl portions of PTP-NP proteins can also be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a PTP-NP polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") PTP-NP protein. For example, Roman et al. (1994) *Eur J Biochem* 222:65–73 describe the use of competitive-binding assays using short, overlapping synthetic peptides from larger proteins to identify binding domains.

The recombinant PTP-NP polypeptides of the present invention also include homologs of the authentic PTP-NP proteins, such as versions of those protein which are resistant to proteolytic cleavage, as for example, due to mutations which alter ubiquitination, enzymatic release of the extracellular domain, or other enzymatic targeting associated with the protein.

Modification of the structure of the subject PTP-NP polypeptides can be for such purposes as enhancing therapeutic or prophylactic efficacy, stability (e.g., ex vivo shelf life and resistance to proteolytic degradation in vivo), or post-translational modifications (e.g., to alter glycosylation or phosphorylation patterns of protein). Such modified peptides, when designed to retain at least one activity of the naturally-occurring form of the protein, or to produce specific antagonists thereof, are considered functional equivalents of the PTP-NP polypeptides (though they may be agonistic or antagonistic of the bioactivities of the authentic protein). Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families:

(1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing= cysteine and methionine. (see, for example, Biochemistry, 2nd ed., Ed. by L. Stryer, W H Freeman and Co.: 1981). Whether a change in the amino acid sequence of a peptide results in a functional PTP-NP homolog (e.g. functional in the sense that the resulting polypeptide mimics or antagonizes the authentic form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial point mutants of the subject PTP-NP proteins as well as truncation mutants, and is especially useful for identifying potential variant sequences (e.g. homologs) that are functional in modulating signal transduction and/or ligand binding. The purpose of screening such combinatorial libraries is to generate, for example, novel PTP-NP homologs which can act as either agonists or antagonist, or alternatively, possess novel activities all together. To illustrate, PTP-NP homologs can be engineered by the present method to provide selective, constitutive activation of NP activity, or alternatively, to be dominant negative inhibitors of PTP-NP-dependent signal transduction. For instance, mutagenesis can provide PTP-NP homologs which are able to bind extracellular ligands yet be unable to bind or signal through intracellular regulatory proteins.

In one aspect of this method, the amino acid sequences for a population of PTP-NP homologs or other related proteins are aligned, preferably to promote the highest homology possible. Such a population of variants can include, for example, PTP-NP homologs from one or more species. Amino acids which appear at each position of the aligned sequences are selected to create a degenerate set of combinatorial sequences. In a preferred embodiment, the variegated library of PTP-NP variants is generated by combinatorial mutagenesis at the nucleic acid level, and is encoded by a variegated gene library. For instance, a mixture of synthetic oligonucleotides can be enzymatically ligated into gene sequences such that the degenerate set of potential PTP-NP sequences are expressible as individual polypeptides, or alternatively, as a set of larger fusion proteins (e.g. for phage display) containing the set of PTP-NP sequences therein.

There are many ways by which such libraries of potential PTP-NP homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential PTP-NP sequences. The synthesis of degenerate oligonucleotides is well known in the art (see for example, Narang, SA (1983) Tetrahedron 39:3; Itakura et al. (1981) Recombinant DNA, Proc 3rd Cleveland Sympos. Macromolecules, ed. A G Walton, Amsterdam: Elsevier pp273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) PNAS 89:2429–2433; Devlin et al. (1990) Science 249: 404–406; Cwirla et al. (1990) PNAS 87: 6378–6382; as well as U.S. Pat. Nos. 5,223,409, 5,198,346, and 5,096,815).

Likewise, a library of coding sequence fragments can be provided for a PTP-NP clone in order to generate a variegated population of PTP-NP fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a PTP-NP coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of PTP-NP homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

In an exemplary embodiment, a library of variants derived from a truncated extracellular domain which are mutated, e.g., by alanine scanning mutagenesis, is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd., and fl are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461).

For example, the recombinant phage antibody system (RPAS, Pharmacia Catalog number 27-9400-01) can be easily modified for use in expressing and screening PTP-NP combinatorial libraries by panning on pancreatic β cells to enrich, in the flow through, for PTP-NP homologs with enhanced ability to bind the ligand.

The invention also provides for reduction of the PTP-NP protein to generate mimetics, e.g. peptide or non-peptide agents, which are able to disrupt a biological activity of a PTP-NP polypeptide of the present invention, e.g. as inhibitors of protein-protein interactions, such as with ligand proteins. Thus, such mutagenic techniques as described above are also useful to map the determinants of the PTP-NP proteins which participate in protein-protein interactions involved in, for example, interaction of the subject PTP-NP polypeptide with ligand or alternatively with intracellular elements.

To illustrate, the critical residues of a subject PTP-NP polypeptide which are involved in molecular recognition of a ligand can be determined and used to generate PTP-NP-derived peptidomimetics which competitively inhibit binding of the authentic PTP-NP protein with that moiety. By employing, for example, scanning mutagenesis to map the amino acid residues of a protein which is involved in binding other proteins, peptidomimetic compounds can be generated which mimic those residues which facilitate the interaction. Such mimetics may then be used to interfere with the normal function of a PTP-NP protein (or its ligand).

For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) *J Med Chem* 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) J Chem Soc Perkin Trans 1:1231), and β-aminoalcohols (Gordon et al. (1985) *Biochem Biophys Res Common* 126:419; and Dann et al. (1986) *Biochem Biophys Res Commun* 134:71).

Another aspect of the invention pertains to an antibody specifically reactive with a PTP-NP protein. For example, by using immunogens derived from a PTP-NP protein, e.g. based on the cDNA sequences, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a PTP-NP polypeptide or an antigenic fragment which is capable of eliciting an antibody response). Techniques for conferring immunogenicity on a protein or peptide include conjugation to carriers or other techniques well known in the art. An immunogenic portion of a PTP-NP protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a PTP-NP protein of a organism, such as a mammal, e.g. antigenic determinants of a protein represented by SEQ ID NO: 2 or closely related homologs (e.g. at least 70% homologous, preferably at least 80% homologous, and more preferably at least 90% homologous). In yet a further preferred embodiment of the present invention, in order to provide, for example, antibodies which are immuno-selective for discrete PTP-NP homologs the anti-PTP-NP polypeptide antibodies do not substantially cross react (i.e. does not react specifically) with a protein which is, for example, less than 85%, 90% or 95% homologous with the selected PTP-NP. By "not substantially cross react", it is meant that the antibody has a binding affinity for a non-homologous protein which is at least one order of magnitude, more preferably at least 2 orders of magnitude, and even more preferably at least 3 orders of magnitude less than the binding affinity of the antibody for the intended target PTP-NP.

Following immunization of an animal with an antigenic preparation of a PTP-NP polypeptide, anti-PTP-NP antisera can be obtained and, if desired, polyclonal anti-PTP-NP antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) Nature, 256: 495–497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77–96). Hybridoma cells can be screened immunochemically for production of antibodies specifically reactive with a PTP-NP polypeptide of the present invention and monoclonal antibodies isolated from a culture comprising such hybridoma cells.

The term antibody as used herein is intended to include fragments thereof which are also specifically reactive with a PTP-NP polypeptide. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific and chimeric molecules having affinity for a PTP-NP protein conferred by at least one CDR region of the antibody.

Both monoclonal and polyclonal antibodies (Ab) directed against authentic PTP-NP polypeptides, or PTP-NP variants, and antibody fragments such as Fab, F(ab)$_2$, Fv and scFv can be used to block the action of a PTP-NP protein and allow the study of the role of these proteins in, for example, differentiation of tissue. Experiments of this nature can aid in deciphering the role of PTP-NP proteins that may be involved in control of proliferation versus differentiation, e.g., in patterning and tissue formation.

Antibodies which specifically bind PTP-NP epitopes can also be used in immunohistochemical staining of tissue samples in order to evaluate the abundance and pattern of expression of each of the subject PTP-NP polypeptides. Anti-PTP-NP antibodies can be used diagnostically in immuno-precipitation and immuno-blotting to detect and evaluate PTP-NP protein levels in tissue as part of a clinical testing procedure. For instance, such measurements can be useful in predictive valuations of the onset or progression of proliferative or differentiative disorders. Likewise, the ability to monitor PTP-NP protein levels in an individual can allow determination of the efficacy of a given treatment regimen for an individual afflicted with such a disorder. The level of PTP-NP polypeptides may be measured from cells in bodily fluid, such as in samples of cerebral spinal fluid or amniotic fluid, or can be measured in tissue, such as produced by biopsy. Diagnostic assays using anti-PTP-NP antibodies can include, for example, immunoassays designed to aid in early diagnosis of a disorder, particularly ones which are manifest at birth. Diagnostic assays using anti-PTP-NP polypeptide antibodies can also include immunoassays designed to aid in early diagnosis and phenotyping neoplastic or hyperplastic disorders.

Another application of anti-PTP-NP antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a PTP-NP protein, e.g. orthologs of the PTP-NP protein from other species, can then be detected with antibodies, as, for example, reacting nitrocellulose filters lifted from infected plates with anti-PTP-NP antibodies. Positive phage detected by this assay can then be isolated from the infected plate. Thus, the presence of PTP-NP homologs can be detected and cloned from other animals, as can alternate isoforms (including splicing variants) from humans.

Moreover, the nucleotide sequences determined from the cloning of PTP-NP genes from organisms will further allow for the generation of probes and primers designed for use in identifying and/or cloning PTP-NP homologs in other cell types, e.g. from other tissues, as well as PTP-NP homologs from other organisms. For instance, the present invention also provides a probe/primer comprising a substantially purified oligonucleotide, which oligonucleotide comprises a region of nucleotide sequence that hybridizes under stringent conditions to at least 15 consecutive nucleotides of sense or anti-sense sequence selected from the group consisting of SEQ ID NO: 1 or naturally occurring mutants thereof. For instance, primers based on the nucleic acid represented in SEQ ID NO: 1 can be used in PCR reactions to clone PTP-NP homologs. Likewise, probes based on the subject PTP-NP sequences can be used to detect transcripts or genomic sequences encoding the same or homologous proteins. In preferred embodiments, the probe further comprises a label group attached thereto and able to be detected, e.g. the label group is selected from amongst radioisotopes, fluorescent compounds, enzymes, and enzyme co-factors.

Such probes can also be used as a part of a diagnostic test kit for identifying cells or tissue which misexpress a PTP-NP protein, such as by measuring a level of a PTP-NP-encoding nucleic acid in a sample of cells from a patient-animal; e.g. detecting PTP-NP mRNA levels or determining whether a genomic PTP-NP gene has been mutated or deleted.

To illustrate, nucleotide probes can be generated from the subject PTP-NP genes which facilitate histological screening of intact tissue and tissue samples for the presence (or absence) of PTP-NP-encoding transcripts. Similar to the diagnostic uses of anti-PTP-NP antibodies, the use of probes directed to PTP-NP messages, or to genomic PTP-NP sequences, can be used for both predictive and therapeutic evaluation of allelic mutations which might be manifest in, for example, degenerative disorders marked by loss of particular cell-types, apoptosis, neoplastic and/or hyperplastic disorders (e.g. unwanted cell growth) or abnormal differentiation of tissue. Used in conjunction with immunoassays as described above, the oligonucleotide probes can help facilitate the determination of the molecular basis for a developmental disorder which may involve some abnormality associated with expression (or lack thereof) of a PTP-NP protein. For instance, variation in polypeptide synthesis can be differentiated from a mutation in a coding sequence.

Accordingly, the present method provides a method for determining if a subject is at risk for a disorder characterized by aberrant apoptosis, cell proliferation and/or differentiation. In preferred embodiments, method can be generally characterized as comprising detecting, in a sample of cells from the subject, the presence or absence of a genetic lesion characterized by at least one of (i) an alteration affecting the integrity of a gene encoding a PTP-NP-protein, or (ii) the mis-expression of the PTP-NP gene. To illustrate, such genetic lesions can be detected by ascertaining the existence of at least one of (i) a deletion of one or more nucleotides from a PTP-NP gene, (ii) an addition of one or more nucleotides to a PTP-NP gene, (iii) a substitution of one or more nucleotides of a PTP-NP gene, (iv) a gross chromosomal rearrangement of a PTP-NP gene, (v) a gross alteration in the level of a messenger RNA transcript of a PTP-NP gene, (vii) aberrant modification of a PTP-NP gene, such as of the methylation pattern of the genomic DNA, (vii) the presence of a non-wild type splicing pattern of a messenger RNA transcript of a PTP-NP gene, (viii) a non-wild type level of a PTP-NP-protein, and (ix) inappropriate post-translational modification of a PTP-NP-protein. As set out below, the present invention provides a large number of assay techniques for detecting lesions in a PTP-NP gene, and importantly, provides the ability to discern between different molecular causes underlying PTP-NP-dependent aberrant cell growth, proliferation and/or differentiation.

In an exemplary embodiment, there is provided a nucleic acid composition comprising a (purified) oligonucleotide probe including a region of nucleotide sequence which is capable of hybridizing to a sense or antisense sequence of a PTP-NP gene, such as represented by SEQ ID NO: 1, or naturally occurring mutants thereof, or 5' or 3' flanking sequences or intronic sequences naturally associated with the subject PTP-NP genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1944) PNAS 91:360–364), the later of which can be particularly useful for detecting point mutations in the PTP-NP gene. In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a PTP-NP gene under conditions such that hybridization and amplification of the PTP-NP gene (if present)

occurs, and (iv) detecting the presence or absence of an amplification product, or detecting the size of the amplification product and comparing the length to a control sample.

In still another embodiment, the level of a PTP-NP-protein can be detected by immunoassay. For instance, the cells of a biopsy sample can be lysed, and the level of a PTP-NP-protein present in the cell can be quantitated by standard immunoassay techniques. In yet another exemplary embodiment, aberrant methylation patterns of a PTP-NP gene can be detected by digesting genomic DNA from a patient sample with one or more restriction endonucleases that are sensitive to methylation and for which recognition sites exist in the PTP-NP gene (including in the flanking and intronic sequences). See, for example, Buiting et al. (1994) Human Mol Genet 3:893–895. Digested DNA is separated by gel electrophoresis, and hybridized with probes derived from, for example, genomic or cDNA sequences. The methylation status of the PTP-NP gene can be determined by comparison of the restriction pattern generated from the sample DNA with that for a standard of known methylation.

In still other embodiments, the extracellular domain of the PTP-NP receptor can be used to quantitatively detect the level of PTP-NP ligands. To illustrate, a soluble form of the N-terminus of the receptor can be generated by truncation of the protein prior to the transmembrane domain. Samples of bodily fluid(s), e.g., plasma, serum, lymph, marrow, cerebral/spinal fluid, urine and the like can be contacted with the receptor under conditions wherein ligand/receptor binding can occur, and the level of ligand/receptor complexes formed can be detected by any of a variety of techniques known in the art. For example, competitive binding assays using standardized samples of a known PTP-NP ligand can be used to quantitate the amount of analyte bound from the fluid sample.

In yet other embodiments, such PTP-NP receptors can be used to detect the presence of a PTP-NP ligand on a cell surface. For instance, the PTP-NP protein can be contacted with cells from a biopsy, and the ability of the PTP-NP protein to decorate certain cells of the sample is ascertained. The binding of the PTP-NP protein to cell populations of the sample can be detected, for example, by the use of antibodies against the PTP-NP protein, or by detection of a label associated with the PTP-NP protein. In the case of the latter, the PTP-NP protein can be labeled, for example, by chemical modification or as a fusion protein. Exemplary labels include radioisotopes, fluorescent compounds, enzyme co-factors, which can be added by chemical modification of the protein, and epitope tags such as myc, pFLAG and the like, or enzymatic activities such as GST or alkaline phosphatase which can be added either by chemical modification or by generation of a fusion protein.

Furthermore, the present invention also contemplates the detection of soluble forms of the PTP-NP receptor in bodily fluid samples. As described in the art, e.g., see Diez-Ruiz et al. (1995) Eur J Haematol 54:1–8 and Owen-Schaub et al. (1995) Cancer Lett 94:1–8, in certain instances soluble forms of receptors are believed to play a role as modulators of the biological function of their cognate ligands in an agonist/antagonist pattern. In various pathologic states, the production and release of soluble PTP-NP receptors may mediate host response and determine the course and outcome of disease by interacting with PTP-NP ligands and competing with cell surface receptors. The determination of soluble PTP-NP receptors in body fluids is a new tool to gain information about various disease states, and may be of prognostic value to a clinician. For example, the level of soluble PTP-NP protein in a body fluid may give useful information for monitoring, inter alia, neurodegenerative disorders and/or pancreodegenerative diseases.

The level of soluble receptor present in a given sample can be quantitated, in light of the present disclosure, using known procedures and techniques. For example, antibodies immunoselective for the extracellular domain of the PTP-NP protein can be used to detect and quantify its presence in a sample, e.g., by well-known immunoassay techniques. Alternatively, a labeled ligand of the receptor can be used to detect the presence of the receptor in the fluid sample.

In yet another aspect of the invention, the subject PTP-NP polypeptides can be used to generate a "two hybrid" assay or an "interaction trap" assay (see, for example, U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), for isolating coding sequences for other cellular proteins which bind PTP-NPs ("PTP-NP-binding proteins" or "PTP-NP-bp"). Such PTP-NP-binding proteins would likely be involved in the regulation of PTP-NP, e.g., as TRAFs or other signal transducers.

Briefly, the interaction trap relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for a PTP-NP polypeptide, such as the cytoplasmic domain. Preferably, if the phosphatase domain is included, one or more of the active site residues will be mutated to provide a catalytically inactive mutant which nevertheless retains the ability to bind to its intracellular substrate(s). The second hybrid protein encodes a transcriptional activation domain fused in frame to a sample gene from a cDNA library. If the bait and sample hybrid proteins are able to interact, e.g., form a PTP-NP-dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the PTP-NP and sample proteins.

A number of techniques exist in the art for now identifying the ligand of the PTP-NP receptor. For instance, expression cloning can be carried out on a cDNA or genomic library by isolating cells which are decorated with a labeled form of the receptor. In a preferred embodiment, the technique uses the PTP-NP receptor in an in situ assay for detecting PTP-NP ligands in tissue samples and whole organisms. In general, the RAP-in situ assay described below (for Receptor Affinity Probe) of Flanagan and Leder (see PCT publications WO 92/06220; and also Cheng et al. (1994) Cell 79:157–168) involves the use of an expression cloning system whereby a PTP-NP ligand is scored on the basis of binding to a PTP-NP/alkaline phosphatase fusion protein. In general, the method comprises (i) providing a hybrid molecule (the affinity probe) including the PTP-NP receptor, or at least the extracellular domain thereof, covalently bonded to an enzymatically active tag, preferably for which chromogenic substrates exist, (ii) contacting the tissue or organism with the affinity probe to form complexes between the probe and a cognate ligand in the sample, removing unbound probe, and (iii) detecting the affinity complex using a chromogenic substrate for the enzymatic activity associated with the affinity probe.

This method, unlike other prior art methods which are carried out only on dispersed cell cultures, provides a means for probing non-dispersed and wholemount tissue and animal samples. The method can be used, in addition to facilitating the cloning of PTP-NP ligands, also for detecting patterns of expression for particular ligands of the PTP-NP receptor, for measuring the affinity of receptor/ligand interactions in tissue samples, as well as for generating drug screening assays in tissue samples. Moreover, the affinity probe can also be used in diagnostic screening to determine whether a PTP-NP ligand is misexpressed.

Furthermore, by making available purified and recombinant PTP-NP polypeptides, the present invention facilitates the development of assays which can be used to screen for drugs which are either agonists or antagonists of the normal cellular function of the subject PTP-NP receptor, or of its role in the pathogenesis of cellular maintenance, differentiation and/or proliferation and disorders related thereto. In a general sense, the assay evaluates the ability of a compound to modulate binding between a PTP-NP polypeptide and a molecule, be it derived from a cellular protein (substrate or other intracellular signalling molecule) or an extracellular protein (ligand), that interacts with the PTP-NP polypeptide. Exemplary compounds which can be screened against such PTP-NP-mediated interactions include peptides, nucleic acids, carbohydrates, small organic molecules, and natural product extract libraries, such as isolated from animals, plants, fungus and/or microbes.

It is contemplated that any of the novel interactions described herein could be exploited in a drug screening assay. For example, in one embodiment, the interaction between a PTP-NP protein and a ligand on the surface of a β cell can be detected in the presence and the absence of a test compound. Likewise, the ability of test compound to inhibit the phosphatase activity of the PTP-NP polypeptide.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements. Accordingly, in an exemplary screening assay of the present invention, a reaction mixture is generated to include a PTP-NP polypeptide, compound(s) of interest, and a "target molecule", e.g., a protein, which interacts with the PTP-NP polypeptide. Exemplary target molecules include ligands, as well as peptide and non-peptide substrates. Detection and quantification of interaction of the PTP-NP polypeptide with the target molecule provides a means for determining a compound's efficacy at inhibiting (or potentiating) interaction between the PTP-NP and the target molecule. The efficacy of the compound can be assessed by generating dose response curves from data obtained using various concentrations of the test compound. Moreover, a control assay can also be performed to provide a baseline for comparison. In the control assay, interaction of the PTP-NP polypeptide and target molecule is quantitated in the absence of the test compound.

Interaction between the PTP-NP polypeptide and the target molecule may be detected by a variety of techniques. Modulation of the formation of complexes can be quantitated using, for example, detectably labeled proteins such as radiolabeled, fluorescently labeled, or enzymatically labeled PTP-NP polypeptides, by immunoassay, by chromatographic detection, or by detecting the intrinsic activity of the acetylase.

Typically, it will be desirable to immobilize either PTP-NP or the target molecule to facilitate separation of complexes from uncomplexed forms of one or both of the proteins, as well as to accommodate automation of the assay. Binding of PTP-NP to the target molecule, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/PTP-NP (GST/PTP-NP) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of target molecule found in the bead fraction quantitated from the gel using standard electrophoretic techniques such as described in the appended examples.

Other techniques for immobilizing proteins and other molecules on matrices are also available for use in the subject assay. For instance, either PTP-NP or target molecule can be immobilized utilizing conjugation of biotin and streptavidin. For instance, biotinylated PTP-NP molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with PTP-NP, but which do not interfere with the interaction between the PTP-NP and target molecule, can be derivatized to the wells of the plate, and PTP-NP trapped in the wells by antibody conjugation. As above, preparations of an target molecule and a test compound are incubated in the PTP-NP-presenting wells of the plate, and the amount of complex trapped in the well can be quantitated. Exemplary methods for detecting such complexes, in addition to those described above for the GST-immobilized complexes, include immunodetection of complexes using antibodies reactive with the target molecule, or which are reactive with PTP-NP protein and compete with the target molecule; as well as enzyme-linked assays which rely on detecting an enzymatic activity associated with the target molecule, either intrinsic or extrinsic activity. In the instance of the latter, the enzyme can be chemically conjugated or provided as a fusion protein with the target molecule. To illustrate, the target molecule can be chemically cross-linked or genetically fused (if it is a polypeptide) with horseradish peroxidase, and the amount of polypeptide trapped in the complex can be assessed with a chromogenic substrate of the enzyme, e.g. 3,3'-diaminobenzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating proteins trapped in the complex, antibodies against the protein, such as anti-PTP-NP antibodies, can be used. Alternatively, the protein to be detected in the complex can be "epitope tagged" in the form of a fusion protein which includes, in addition to the PTP-NP sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, N.J.).

In another embodiment of a drug screening, a two hybrid assay (described supra) can be generated with a PTP-NP and target molecule. Drug dependent inhibition or potentiation of the interaction can be scored.

In still other embodiments, the target molecule can be a substrate for the phosphatase activity of the PTP-NP protein. The extent to which the substrate is converted to product in the presence of the test compound is compared with the extent of substrate conversion in the absence of the compound. This method is a simple and rapid screening test which, in one embodiment, uses a synthetic substrate such as p-nitrophenylphosphate (pNPP), 3-O-methyl-1-fluorescein monophosphate (MFP) or Fluorescein diphosphate (FDP) to score for phosphatase activity. The method can be carried out as a rapid colorimetric microtitration plate assay to test the subject compounds. Other substrates will be evident to the skilled artisan, including phosphorylated peptides.

In yet another embodiment, the drug screening assay is derived to include a whole cell recombinantly expressing a PTP-NP polypeptide. The ability of a test agent to alter the activity of the PTP-NP protein can be detected by analysis of the recombinant cell. For example, agonists and antagonists of the PTP-NP biological activity can by detected by scoring for alterations in growth or differentiation (phenotype) of the cell. General techniques for detecting each are well known, and will vary with respect to the source of the particular reagent cell utilized in any given assay.

In an exemplary embodiment, a cell which expresses the PTP-NP receptor, e.g, whether endogenous or heterologous, can be contacted with a ligand of the PTP-NP receptor which is capable of inducing signal transduction from the receptor, and the resulting signaling detected either at various points in the pathway, or on the basis of a phenotypic change to the reagent cell. In one embodiment, the reagent cell is contacted with antibody which causes cross-linking of the receptor, and the signal cascade induced by that cross-linking is subsequently detected. A test compound which modulates that pathway, e.g., potentiates or inhibits, can be detected by comparison with control experiments which either lack the receptor or lack the test compound. For example, visual inspection of the morphology of the reagent cell can be used to determine whether the biological activity of the targeted PTP-NP protein has been affected by the added agent. In yet another embodiment, the assay can be generated to evolve a detection signal from the expression or modification of a cellular protein effected by the activity of PTP-NP-mediated signaling. Such measurement can be accomplished by detecting a biological activity modulated by the downstream effects of the receptor activity.

For example, the alteration of expression of a reporter gene construct provided in the reagent cell provides a means of detecting the effect on PTP-NP activity. For example, reporter gene constructs derived using the transcriptional regulatory sequences, e.g. the promoters, from genes regulated by the signalling of the PTP-NP receptor can be used to drive the expression of a detectable marker. Many reporter genes are known to those of skill in the art and others may be identified or synthesized by methods known to those of skill in the art. A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101), human placental secreted alkaline phosphatase (Cullen and Malim (1992) Methods in Enzymol. 216:362–368).

In still other embodiments, the signal generated by engagement of the PTP-NP receptor can be detected by scoring for the production of second messengers. For example, in various embodiments the assay may assess the ability of test agent to cause changes in phophorylation patterns, adenylate cyclase activity (cAMP production), GTP hydrolysis, calcium mobilization, and/or phospholipid hydrolysis upon receptor stimulation.

Another aspect of the present invention relates to a method of inducing and/or maintaining a differentiated state, enhancing survival, and/or inhibiting (or alternatively potentiating) proliferation of a cell, by contacting the cells with an agent which modulates PTP-NP-dependent signal transduction pathways. The subject method could be used to generate and/or maintain an array of different tissue both in vitro and in vivo. A "PTP-NP therapeutic," whether inhibitory or potentiating with respect to modulating signaling by the PTP-NP receptor, can be, as appropriate, any of the preparations described above, including isolated polypeptides, gene therapy constructs, antisense molecules, peptidomimetics or agents identified in the drug assays provided herein. In certain embodiments, soluble forms of the PTP-NP protein including the extracellular ligand-binding domain of the receptor can be provided as a means for antagonizing the binding of a PTP-NP ligand to a cell-surface PTP-NP receptor. For instance, such forms of the receptor can be used to antagonize the bioactivity of a ligand of the receptor.

The PTP-NP compounds of the present invention are likely to play an important role in the modulation of cellular proliferation and maintenance of pancreatic and neuronal tissue during disease states. It will also be apparent that, by transient use of modulators of PTP-NP activities, in vivo reformation of tissue can be accomplished, e.g. in the development and maintenance of organs. By controlling the proliferative and differentiative potential for different cells, the subject PTP-NP therapeutics can be used to reform injured tissue, or to improve grafting and morphology of transplanted tissue. For instance, PTP-NP antagonists and agonists can be employed in a differential manner to regulate different stages of organ repair after physical, chemical or pathological insult. The present method is also applicable to cell culture techniques.

In one embodiment, the PTP-NP therapeutic of the present invention can be used to induce differentiation of uncommitted pancreatic or neuronal progenitor cells and thereby give rise to a committed progenitor cell, or to cause further restriction of the developmental fate of a committed progenitor cell towards becoming a particular terminally-differentiated cell.

Another aspect of the invention features transgenic non-human animals which express a heterologous PTP-NP gene of the present invention, and/or which have had one or more genomic PTP-NP genes disrupted in at least a tissue or cell-types of the animal. Accordingly, the invention features an animal model for developmental diseases, which animal has one or more PTP-NP allele which is mis-expressed. For example, an animal can be generated which has one or more PTP-NP alleles deleted or otherwise rendered inactive. Such a model can then be used to study disorders arising from mis-expressed PTP-NP genes, as well as for evaluating potential therapies for similar disorders.

The transgenic animals of the present invention all include within a plurality of their cells a transgene of the present invention, which transgene alters the phenotype of the "host cell" with respect to regulation by the PTP-NP receptor, e.g., of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In one embodiment, the transgene construct is a knockout construct. Such transgene constructs usually are insertion-type or replacement-type constructs (Hasty et al. (1991) *Mol Cell Biol* 11:4509). The transgene constructs for disruption of a PTP-NP gene are designed to facilitate homologous recombination with a portion of the genomic PTP-NP gene so as to prevent the functional expression of the endogenous PTP-NP gene. In preferred embodiments, the nucleotide sequence used as the knockout construct can be comprised of (1) DNA from some portion of the endogenous PTP-NP gene (exon sequence, intron sequence, promoter sequences, etc.) which direct recombination and (2) a marker sequence which is used to detect the presence of the knockout construct in the cell. The knockout construct is inserted into a cell, and integrates with the genomic DNA of the cell in such a position so as to prevent or interrupt transcription of the native PTP-NP gene. Such insertion can occur by homologous recombination, i.e., regions of the knockout construct that are homologous to the endogenous PTP-NP gene sequence hybridize to the genomic DNA and recombine with the genomic sequences so that the construct is incorporated into the corresponding position of the genomic DNA. The knockout construct can comprise (1) a full or partial sequence of one or more exons and/or introns of the PTP-NP gene to be disrupted, (2) sequences which flank the 5' and 3' ends of the coding sequence of the PTP-NP gene, or (3) a combination thereof.

A preferred knockout construct will delete, by targeted homologous recombination, essential structural elements of an endogenous PTP-NP gene. For example, the targeting construct can recombine with the genomic PTP-NP gene can delete a portion of the coding sequence, and/or essential transcriptional regulatory sequences of the gene.

Alternatively, the knockout construct can be used to interrupt essential structural and/or regulatory elements of an endogenous PTP-NP gene by targeted insertion of a polynucleotide sequence. For instance, a knockout construct can recombine with a PTP-NP gene and insert a nonhomologous sequence, such as a neo expression cassette, into a structural element (e.g., an exon) and/or regulatory element (e.g., enhancer, promoter, intron splice site, polyadenylation site, etc.) to yield a targeted PTP-NP allele having an insertional disruption. The inserted nucleic acid can range in size from 1 nucleotide (e.g., to produce a frameshift) to several kilobases or more, and is limited only by the efficiency of the targeting technique.

Depending of the location and characteristics of the disruption, the transgene construct can be used to generate a transgenic animal in which substantially all expression of the targeted PTP-NP gene is inhibited in at least a portion of the animal's cells. If only regulatory elements are targeted, some low-level expression of the targeted gene may occur (i.e., the targeted allele is "leaky").

The nucleotide sequence(s) comprising the knockout construct(s) can be obtained using methods well known in the art. Such methods include, for example, screening genomic libraries with PTP-NP cDNA probes in order to identify the corresponding genomic PTP-NP gene and regulatory sequences. Alternatively, where the cDNA sequence is to be used as part of the knockout construct, the cDNA may be obtained by screening a cDNA library as set out above.

In another embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, ME). Preferred strains are those with $H-2^b$, $H-2^d$ or $H-2^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. The use of zygotes as a target for gene transfer has a major advantage in that in most cases the injected DNA will be incorporated into the host gene before the first cleavage (Brinster et al. (1985) PNAS 82:4438–4442). As a consequence, all cells of the transgenic animal will carry the incorporated transgene. This will in general also be reflected in the efficient transmission of the transgene to offspring of the founder since 50% of the germ cells will harbor the transgene.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from excised tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

In one embodiment, gene targeting, which is a method of using homologous recombination to modify an animal's genome, can be used to introduce changes into cultured embryonic stem cells. By targeting the PTP-NP gene in ES cells, these changes can be introduced into the germlines of animals to generate chimeras. The gene targeting procedure is accomplished by introducing into tissue culture cells a DNA targeting construct that includes a segment homologous to a PTP-NP locus, and which also includes an intended sequence modification to the PTP-NP genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a PTP-NP gene function through the use of a targeting transgene construct designed to undergo homologous recombination with PTP-NP genomic sequences. Targeting construct can be arranged so that, upon recombination with an element of a PTP-NP gene, a positive selection marker is inserted into (or replaces) coding sequences of the targeted PTP-NP gene. The inserted sequence functionally disrupts the PTP-NP gene, while also providing a positive selection trait.

Generally, the embryonic stem cells (ES cells) used to produce the knockout animals will be of the same species as the knockout animal to be generated. Thus for example, mouse embryonic stem cells will usually be used for generation of a PTP-NP-knockout mice.

Embryonic stem cells are generated and maintained using methods well known to the skilled artisan such as those described by Doetschman et al. (1985) *J. Embryol. Exp. Morphol.* 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); Bradley et al. (1986) *Current Topics in Devel. Biol.* 20:357–371); and by Hogan et al. (Manipulating the Mouse Embryo: A Laboratory Manual, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment. A preferred method of insertion is electroporation.

Each knockout construct to be inserted into the cell must first be in the linear form. Therefore, if the knockout construct has been inserted into a vector, linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

If the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knockout construct.

Screening can be accomplished using a variety of methods. Where the marker gene is an antibiotic resistance gene, the ES cells may be cultured in the presence of an otherwise lethal concentration of antibiotic. Those ES cells that survive have presumably integrated the knockout construct. If the marker gene is other than an antibiotic resistance gene, a Southern blot of the ES cell genomic DNA can be probed with a sequence of DNA designed to hybridize only to the marker sequence Alternatively, PCR can be used. Finally, if the marker gene is a gene that encodes an enzyme whose activity can be detected (e.g., β-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

The knockout construct may integrate into several locations in the ES cell genome, and may integrate into a different location in each ES cell's genome due to the occurrence of random insertion events. The desired location of insertion is in a complementary position to the DNA sequence to be knocked out, e.g., the PTP-NP coding sequence, transcriptional regulatory sequence, etc. Typically, less than about 1–5 percent of the ES cells that take up the knockout construct will actually integrate the knockout construct in the desired location. To identify those ES cells with proper integration of the knockout construct, total DNA can be extracted from the ES cells using standard methods. The DNA can then be probed on a Southern blot with a probe or probes designed to hybridize in a specific pattern to genomic DNA digested with particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, the transformed ES cells can be microinjected into blastocytes.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent.

Offspring that are born to the foster mother may be screened initially for PTP-NP disruptants, DNA from tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from animals that are the product of this cross, as well as animals that are known heterozygotes and wild type animals.

Other means of identifying and characterizing the knockout offspring are available. For example, Northern blots can be used to probe the mRNA for the presence or absence of transcripts of either the PTP-NP gene, the marker gene, or both. In addition, Western blots can be used to assess the (loss of) level of expression of the PTP-NP gene knocked out in various tissues of the offspring by probing the Western blot with an antibody against the PTP-NP protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies or PTP-NP ligands to look for the presence or absence of the knockout construct gene product.

Animals containing more than one knockout construct and/or more than one transgene expression construct are prepared in any of several ways. The preferred manner of preparation is to generate a series of animals, each containing a desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s). Thus, a transgenic avian species can be generated by breeding a first transgenic bird in which the wild-type PTP-NP gene is disrupted with a second transgenic bird which has been engineered to express a mutant PTP-NP which retains most other biological functions of the receptor except for ALSV binding.

The transformed animals, their progeny, and cell lines of the present invention provide several important uses that will be readily apparent to one of ordinary skill in the art.

To illustrate, the transgenic animals and cell lines are particularly useful in screening compounds that have potential as prophylactic or therapeutic treatments of diseases such as may involve aberrant expression, or loss, of a PTP-NP gene, or aberrant or unwanted activation of receptor signaling. Screening for a useful drug would involve administering the candidate drug over a range of doses to the transgenic animal, and assaying at various time points for the effect(s) of the drug on the disease or disorder being evaluated. Alternatively, or additionally, the drug could be administered prior to or simultaneously with exposure to induction of the disease, if applicable.

In one embodiment, candidate compounds are screened by being administered to the transgenic animal, over a range of doses, and evaluating the animal's physiological response to the compound(s) over time. Administration may be oral, or by suitable injection, depending on the chemical nature of the compound being evaluated. In some cases, it may be appropriate to administer the compound in conjunction with co-factors that would enhance the efficacy of the compound.

In screening cell lines derived from the subject transgenic animals for compounds useful in treating various disorders, the test compound is added to the cell culture medium at the appropriate time, and the cellular response to the compound is evaluated over time using the appropriate biochemical and/or histological assays. In some cases, it may be appropriate to apply the compound of interest to the culture medium in conjunction with co-factors that would enhance the efficacy of the compound.

EXEMPLIFICATION

The invention, now being generally described, will be more readily understood by reference to the following examples, which are included merely for purposes of illustration of certain aspects and embodiments of the present invention and are not intended to limit the invention.

The cDNA sequence of a clone PTP-NP indicates a receptor-type transmembrane molecule. At early organogenesis, in situ hybridization with a probe for the PTP-NP extracellular region detects expression confined to the region of the developing pancreas, an organ of medical importance, but poorly understood with regard to molecular mechanisms of developmental control. This localized expression appears early, even before morphological differentiation of the pancreas, and is found in presumptive precursors of the endocrine cells by the earliest times they can be distinguished. In neural development, an alternate RNA with a different or missing extracellular region is expressed transiently at early stages of neurogenesis, and the full-length PTP-NP RNA appears later. To search for a ligand of PTP-NP, a fusion protein probe was made with the extracellular domain fused to an alkaline phosphatase tag. This probe bound strongly to pancreatic islets, providing evidence for a ligand-receptor interaction that could be involved in endocrine cell regulation. The results show PTP-NP is an especially early marker for pancreatic development, and suggest it may be a receptor that could control the development of pancreatic endocrine cells.

I. Materials and Methods
(a) PCR Amplification of PTP Fragments and Identification of PTP-NP cDNA Clones Total RNA from dissected neural tube was isolated by the single-step RNA isolation method (Kingston et al., 1994). After reverse transcription to produce single strand cDNAs, PCR amplification was performed with degenerate primers corresponding to conserved sequences in the phosphatase domain of known PTPs. The sense primer was TT(C/T)TGG (A/C)(A/G)NATG(A/G)TNTGG (SEQ ID NO: 10), corresponding to the sequence FWRM(I/V)W (SEQ ID NO: 11), and the anti-sense primer was A(C/T)NCCNGCN(C/G)(A/T)(A/G)CA(A/G)TG (SEQ ID NO: 12), corresponding to the sequence HCSAG(I/V) (SEQ ID NO: 13). PCR was carried out for 40 cycles: 940C, 1 min; 400C, 5 min; 720C, 30 sec. PCR products in the expected size range of approximately 320–400 bp were then purified by agarose gel electrophoresis and subcloned into the Bluescript II KS(+) vector for sequence analysis. Among the clones analyzed, a novel phosphatase domain sequence of 359 bp was identified and used as a probe to screen a mouse brain cDNA library. Overlapping clones contained a sequence of 3200 bp which covered the whole coding sequence of 1001 amino acids illustrated in FIG. 1A.

(b) P19 in Vitro Induction of Neuronal Differentiation

P19 cells were maintained in alpha modification of MEM supplemented with 2.5% fetal calf serum and 7.5% calf serum. For induction of neuronal differentiation, cells were trypsinized and seeded at 105/ml in bacteriological grade petri dishes with medium containing 1 mM retinoic acid (RA) (Jones-Villeneuve et al., 1982; MacBurney et al., 1982). The medium was replaced every two days, and 6 days after the induction, aggregated cells were plated onto tissue culture grade plates containing medium without RA.

(c) RNA in Situ Hybridizations and Northern Blotting

Two separate antisense PTP-NP probes were used for Nothern blot and in situ hybridization (FIG. 1B). Probe 1 was a fragment of approximately 1.23 kb extending from the 5' end of the cloned sequence to a unique XbaI site at nucleotide 1238; probe 2 was a 955 bp fragment from the XbaI site to nucleotide 2192 in the cytoplasmic domain. Northern blot hybridizations were performed by standard procedures, with two final high stringency washes at 0.2× SSPE, 1% SDS, 65_C. Embryos were isolated from outbred Swiss Webster mice and were considered to be 0.5 days of gestation at noon of the day that plugs were detected. In situ hybridization of whole-mounts or sections was performed as described elsewhere using digoxigenin-labeled antisense riboprobes (Wilkinson, 1992; Wilkinson and Nieto, 1993; Cheng and Flanagan, 1994).

(c) RAP in situ Analysis

To construct an NP-AP expression plasmid, encoding the extracellular domain of PTP-NP fused to an alkaline phosphatase tag, the cDNA sequence from nucleotide 33 to 1832 was amplified by polymerase chain reaction. The PCR product was cut with HindIII and BamHI, and inserted into the same sites of the vector APtag-2 (Cheng et al., 1995). The resulting plasmid, PTP-AP, was transiently transfected with Lipofectamine (GIBCO BRL) into COS cells grown in DMEM with 10% bovine calf serum. Medium was changed 24 and 48 hr after transfection , and the supernatant was harvested after a further 4–6 days. The supernatant was centrifuged, 0.45 mm filtered, and stored at 40C with 20 mM HEPES (pH 7.0) and 0.05% sodium azide.

RAP (receptor affinity probe) in situ analysis was carried out as described (Cheng et al., 1995) with the NP-AP fusion protein as probe. Briefly, frozen sections of pancreas were rinsed with HBHA buffer (Hank's balanced salt solution with 0.5 mg/ml BSA, 0.1% NaN3, 20 mM HEPES [pH 7.0]) and then were overlaid with NP-AP fusion protein supernatant for 75 min at room temperature, washed six times for 5 min each in HBAH, treated with acetone/formaldehyde fixative for 2 min, washed three times with HBS, and heated for 30 min at 65° C. to inactivate endogenous phosphatase activities but not the characteristically heat stable AP activity of the fusion protein. Sections were then stained for 2 hours with NBT and BCIP.

(d) Immunohistochemistry and Double-staining

Guinea pig antibodies against insulin and rabbit antibodies against somatostatin were purchased from Dako corporation. Rabbit antibodies against glucagon were purchased from Chemicon International Inc. For double staining, the samples were first processed for in situ hybridization or RAP in situ analysis as indicated above, except that during the in situ hybridization, the time for the proteinase K treatment was reduced from 6.5 min to 2 min to preserve antigens on the slides. After development for the in situ hybridization or RAP in situ analysis, the sections were then fixed in 4% paraformaldehyde for 20 min, washed 3 times for 10 min each in PBS, pre-blocked in PBS containing 10% goat serum for 30 min, and then incubated with diluted primary antibodies in 2% goat serum for 30 min at room temperature. The slides were then washed 3 times for 5 min in PBS, incubated with 1:200 diluted biotinylated secondary antibody (Vector Labs) in PBS with 2% goat serum for 30 min, followed by 3 washes for 5 min each in PBS. After incubation with 10 mg/ml streptavidin conjugated to the fluorochrome Cy3 (Jackson Immunoresearch Laboratories) in PBS for 30 min, the slides were given three more 5 min washes in PBS, and mounted for viewing (mounting media from Accurate Chemical & Scientific).

II. Results (a) Cloning and Sequence Analysis of PTP-NP.

To search for new PTPs with developmentally regulated expression, we used PCR to amplify PTP cDNAs from dissected neural tubes of day 9.5 embryos. Amplification was carried out with degenerate oligonucleotides corresponding to two conserved regions of the PTP domain: FW(R/Q)M(I/V)W (SEQ ID NO: 14) and HCSAGV SEQ ID NO: 15). A PCR product encoding a novel phosphatase domain was identified, and this 359 bp sequence was used to screen a cDNA library from new-born mouse brain. 20 cDNA clones were isolated, and overlapping clones cover a sequence of 3200 base pairs of cDNA sequence (FIG. 1A). The nucleotide sequence contains an open reading frame that could encode a polypeptide of 1001 amino acids, which was named PTP-NP. This open reading frame starts with a methionine codon in a nucleotide sequence context consistent with a translation initiation site (Kozak, 1987), followed by a typical hydrophobic signal sequence for peptide secretion (von Heijne, 1984) (FIGS. 1A, B). Functionality of these sequences to generate a secreted protein is confirmed by production of a soluble fusion protein with the PTP-NP extracellular domain fused to an alkaline phosphatase tag, as described further below. A stretch of hydrophobic amino acids is located between amino acid residues 601 and 625, and is a predicted transmembrane domain (FIGS. 1A, B). Thus, PTP-NP has the typical structural features of a receptor-like transmembrane molecule with a single cytoplasmic PTP domain.

(b) A New Subgroup in the PTP Sequence Family

When the Genbank database was searched with the PTP-NP sequence, the phosphatase domain of PTP-NP was found to be similar to previously reported PTPs, and shows a particularly close relationship with two other members of the family. One is IA-2, identified from insulinoma cells (Lan et al., 1994; Lu et al., 1994). The other close homolog is B0244.2, identified as a cDNA sequence in a genome project for the nematode *C. elegans*. An alignment of PTP-NP and mIA-2 gives an amino acid identity of 81% in the phosphatase domain, and each of these two genes shows amino acid similarity of 69% in the phosphatase domain when compared to the *C. elegans* gene. In marked contrast to the close intracellular homology, the three sequences show little obvious similarity in their extracellular regions. However, in a region near the N-terminal ends of the extracellular domains the three genes show a short region of sequence conservation (FIG. 2B). Particularly noteworthy in this region are four cysteine residues with exactly conserved spacing, consistent with a conserved disulphide bonded structure. These are the only four cysteines in the PTP-NP extracellular region. Also, four leucine residues are conserved with a spacing of three to four residues, and could form a leucine zipper-like amphipathic region mediating protein-protein interactions. The close similarity of the PTP domains, and the conserved motif in the extracellular domain, defines a new subfamily of PTP sequences.

(c) Northern Blot Analysis of PTP-NP RNA in Adult Tissues

Expression of PTP-NP in adult tissues was analyzed by Northern blot hybridization. Two different parts of the gene were used as probes: probe 1 is derived from the N-terminal end of the extracellular region, while probe 2 contains the C-terminal part of the extracellular domain and a partial cytoplasmic region (FIG. 1B). Both probes detect a major transcript migrating at approximately 5.3 kb expressed in brain and pancreas (FIGS. 3A, B). An additional faint band at approximately 4.5 kb was also detected, at a size consistent with the type 2 transcript described further below, but only in brain and only when probe 2 was used (FIG. 3B). No expression of PTP-NP was detected in any other tissues tested.

(d) Northern Analysis of PTP-NP Expression During Neural Differentiation of P19 Cells, and in Embryos Since PTP-NP had been amplified from the neural tube of day 9.5 embryos, and additionally was found to be expressed strongly in adult brain, we were interested to explore the possibility of a role in neurogenesis. The P19 mouse embryonal carcinoma cell line provides an in vitro model system to analyze regulation of neuronal differentiation. These multipotent cells can be maintained in tissue culture in an undifferentiated state, and when aggregated, can be induced by retinoic acid to differentiate and express characteristics of neurons (Jones-Villeneuve et al., 1982; MacBurney et al., 1982; Bain et al., 1994).

Figure 4A:
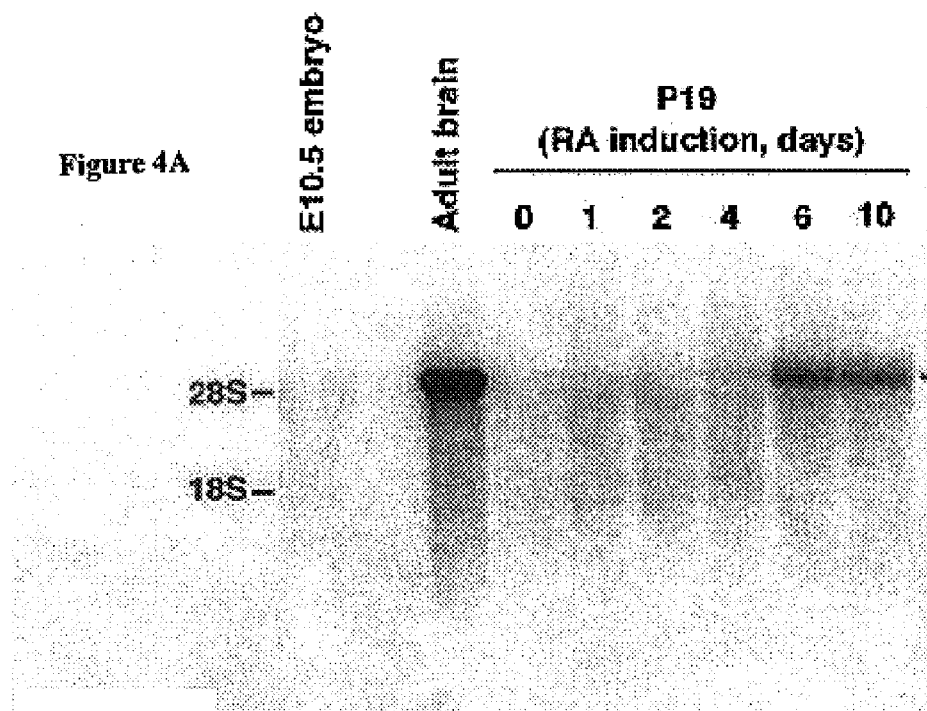
FIGS. 4A and 4B are Northern blot analysis of PTP-NP mRNA during P19 neuronal differentiation. 20 mg total RNA from day 10.5 embryos, 4 mg total RNA from adult brain, and 15 mg total RNA from P19 cells at different stages after RA induction were used for the Northern analysis. The blot was first hybridized with the cDNA probe 1 (FIG. 4A), then was stripped, and rehybridized with the cDNA probe 2 (FIG. 4B).
Figure 4B:
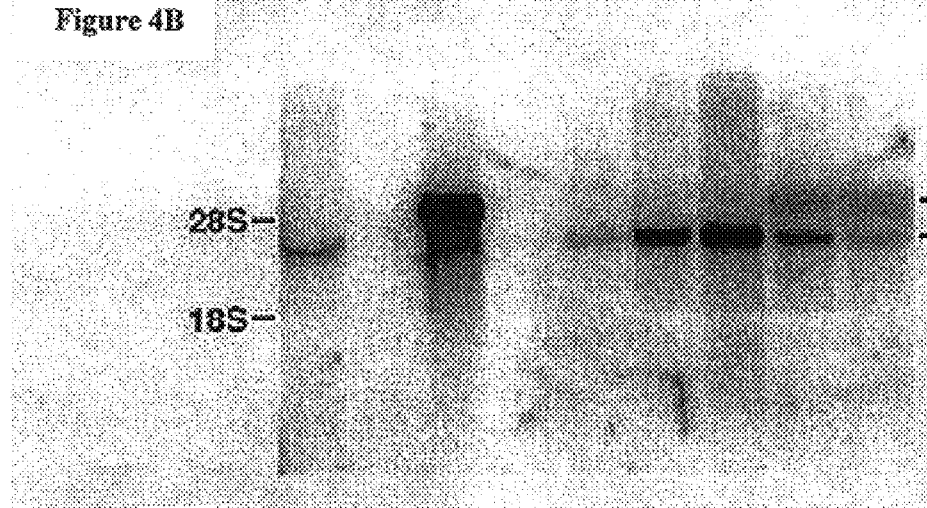
Figure 4C:
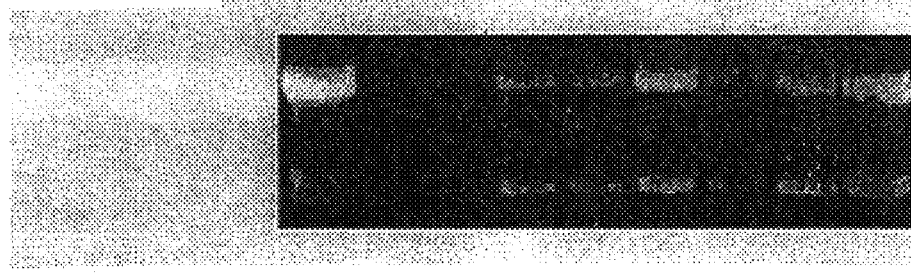
FIG. 4C is an ethidium bromide staining of 28S and 18S ribosomal RNA shown as a control for sample loading.

Northern blot analysis was used to observe the temporal expression pattern of PTP-NP in P19 differentiation. Again, probes 1 and 2 were used separately. No obvious hybridization signal was detected in undifferentiated P19 cells before retinoic acid induction (FIGS. 4A, B). At early time points after induction, by 24 hours, probe 2 detected a single prominent band migrating at approximately 4.5 kb (FIG. 4B). The intensity of this band reached a peak by day 4 after induction, then began to decline at day 6, at which time a lower level of hybridization was seen, with an additional band migrating at 5.3 kb. The size of the 5.3 kb RNA corresponds to the major transcript detected in adult brain (FIGS. 3 and 4). When probe 1 was used, there was no obvious hybridization with the 4.5 kb band, and only the 5.3 kb band appeared prominently (FIG. 4A). When day 10.5 embryos were tested by Northern blot, consistent with the early appearance of the 4.5 kb band in P19 differentiation, a 4.5 kb RNA was the major band detected at this stage, and it hybridized only with probe 2. The transcript that hybridizes with both probes 1 and 2 is defined here as type 1, while the transcript that hybridizes only to probe 2 is defined as type 2. The two transcripts appear to be produced from a single gene, since high-stringency conditions were used for the RNA hybridizations, and a single gene is detected by Southern blot analysis with multiple restriction enzymes (data not shown). Since the type 2 transcript does not hybridize effectively with probe 1, it is presumably missing most or all of the extracellular domain sequence shown in FIG. 1A. At this point we do not know whether it is truncated and lacks an extracellular domain, or whether it might encode a different extracellular domain.

(e) Expression of PTP-NP in Embryonic Nervous System

To test expression in embryos, whole mount in situ hybridization was initially performed at day 9.5 of gestation. Strikingly different patterns were observed with probes 1 and 2. When probe 1 was used in the hybridization, obvious staining was seen only in the pancreatic primordium (Type 1 RNA; FIG. 5A). When probe 2 was used, similar pancreatic hybridization was seen, and there was an additional strong expression in the neural tube (Type 2 RNA; FIG. 5B).

The expression pattern was examined further by hybridization on sections from day 10.5 to 15.5 embryos. At E10.5, probe 2 detected prominent expression in the neural tube, as well as in the pancreatic primordium (FIGS. 5C, D, E, G). Expression was seen in all parts of the neural tube, except in the telencephalon, where staining was weak or absent (FIGS. 5C, D, G). By E10.5, probe 1 detects weak expression in the floorplate and the marginal regions of the neural tube (FIG. 5F). The appearance of staining with probe 1 in the marginal neural tube and the floor plate at this stage approximately correlates with the time and position of neuronal differentiation, and is consistent with the appearance of the type 1 RNA in P19 cells as they progress to more differentiated stages (FIGS. 4A, B).

By E12.5, no major differences in expression patterns were observed with the use of the two probes: the intensity of hybridization detected by probe 2 in the neural tube decreases, while moderate expression detected by probe 1 in the neural tube expands to cover a broader domain (FIGS. 5H, I). By E12.5, PTP-NP was also found to be expressed in cells of the peripheral nervous system, including the sympathetic ganglia and dorsal root ganglia (FIG. 5J), Later, at E13.5 to E15.5, the moderate expression in the neural tube is sustained (data not shown).

Taken together, the results from in situ hybridization and Northern blot analysis indicate that in the developing nervous system, expression of type 1 PTP-NP RNA (detected by probes 1 and 2) begins after the initial stages of neural tube development, and may be correlated with the differentiation of neurons. In contrast, type 2 PTP-NP mRNA (detected by probe 2 only) is expressed strongly but transiently at early stages of neural development, as the neural tube is initially formed.

(f) Expression of PTP-NP in Developing Pancreas

In the pancreatic region, in contrast to the neural tube, probes 1 and 2 detected similar patterns and hybridization intensities at all stages tested, implying that the type 1 RNA is a major form throughout pancreatic development (FIGS. 5A, B, H, I, and data not shown). This conclusion is consistent with the observation that the type 1 RNA at 5.3 kb is the only form detected in adult pancreas (FIG. 3). Expression in the region of the developing pancreas is first seen by E8.5, in the dorsal part of the midgut endoderm, which is believed to give rise to the pancreatic primordium (FIGS. 6A, B, C). The expression of PTP-NP at this early stage precedes the formation of the pancreatic rudiment, and also precedes the expression of known markers that distinguish the exocrine or endocrine lineages (Slack, 1995). At E9.5, PTP-NP is expressed in the pancreatic rudiment, which is now morphologically distinct (FIGS. 5A, B). The expression of PTP-NP in the pancreatic primordium was sustained at later stages of development (E10.5–E15.5; FIGS. 5H, I, and FIG. 7).

Within the newly formed pancreatic rudiment at E9.5, not all the cells express PTP-NP (FIG. 6D and data not shown). To determine whether the PTP-NP expressing cells might include precursors of the pancreatic endocrine cells, we performed double staining, combining in situ hybridization for PTP-NP with immunolocalization for markers of endocrine cell types which first appear at E9.5. As shown in FIGS. 6D, E, F, G, all cells expressing either insulin or glucagon also expressed PTP-NP. This result strongly implies that PTP-NP is expressed in the population of early endocrine progenitor cells. Some additional cells expressed PTP-NP but not insulin or glucagon (FIGS. 6D, E, F, G, and data not shown); these could be cells of a different lineage, or cells that have not yet begun to express the hormonal markers. At later stages of development, PTP-NP is still expressed in all cells of endocrine lineage. At E15.5, as shown in FIGS. 7A–7F, cells expressing insulin, glucagon, or somatostatin were all positive for PTP-NP expression. PTP-NP was also found in cells staining weakly for pancreatic polypeptide at this stage (data not shown). On the other hand, exocrine cells which express amylase were not found to express PTP-NP (FIGS. 7G, H). In adult pancreas too, PTP-NP is expressed in endocrine cells within morphologically distinct pancreatic islets (FIGS. 7I, J).

(g) Detection of a Candidate Ligand for PTP-NP

Since the structure of PTP-NP suggests it could be a receptor, we were interested to test for the possible existence of a ligand. We have previously described the use of fusion proteins, consisting of receptor extracellular domains joined to an AP tag, as probes that can be used to detect ligands (Flanagan and Leder, 1990; Cheng and Flanagan, 1994; Chiang and Flanagan, 1995). The AP tag provides the fusion probe with an intrinsic marker activity that is sensitive and easy to use, and avoids the need for purification of the probes or the use of secondary reagents or radioactive labeling. This approach appears to be widely applicable, and has been used to identify or characterize a variety of ligands (for example: Flanagan and Leder, 1990; Cheng and Flanagan, 1994; Cheng et al., 1995; Chiang and Flanagan, 1995).

To search for a ligand of PTP-NP, we constructed a fusion protein consisting of the extracellular domain of PTP-NP linked to an AP tag (FIG. 8A). This fusion protein, referred to as NP-AP, is a secreted protein and is produced as a single major polypeptide with the expected apparent molecular mass of approximately 140 kDa (FIG. 8B). To test for a ligand directly in tissue, we performed AP (affinity probe) in situ analysis as described previously by applying NP-AP as an affinity reagent directly to frozen sections of adult pancreas, and then testing for bound AP activity with standard histochemical stains.

NP-AP showed strong staining in the pancreas, and the staining was localized to the pancreatic islets, where the endocrine cells are located (FIG. 9A). When AP by itself was used as a negative control, the pancreatic islets showed only background binding comparable to the level seen in the acinar tissue around the islets (FIG. 9B). To characterize the NP-AP stained cells further, we used doubled-labeling with antibodies against endocrine cell markers. The results showed NP-AP bound specifically over the insulin-expressing β cells, and did not bind detectably to α or δ cells (FIGS. 9C–9H). We have not detected homophilic binding of PTP-NP in vitro, in experiments where the extracellular domain was marked with two separate tags (AP and immunoglobulin tags), or where the NP-AP probe was tested for binding to cells transfected with PTP-NP (data not shown). Our results therefore seem most consistent with the existence of a heterophilic ligand for PTP-NP found in pancreatic islets.

III. References Cited in Examples

Bain, G., et al. (1994) From embryonal carcinoma cells to neurons: The P19 pathway. *BioEssays* 16:343–348.

Barnea, G., et al. (1994) Receptor tyrosine phosphatase b is expressed in the form of proteoglycan and binds to the extracellular matrix protein tenascin. *J. Biol. Chem.* 269:14349–14352.

Brady-Kalnay, SM, et al. (1993) Homophilic binding of PTPm, a receptor-type protein tyrosine phosphatase, can mediate cell-cell aggregation. *J. Cell Biol.* 122:961–972.

Brady-Kalnay, SM, and Tonks NK (1995) Protein tyrosine phosphatases as adhesion receptors. *Curr. Opin. Cell Biol.* 7:650–657.

Cantley, LC, et al. (1991) Oncogenes and signal transduction. Cell 64:281–302.

Carnoll, PD, et al. (1993) The expression of a novel receptor-type tyrosine phosphatase suggests a role in morphogenesis and plasticity of the nervous system. *Dev. Brain Res.* 75:293–298.

Cheng, H.-J., and Flanagan, J G (1994) Identification and cloning of PTP-NP, a developmentally expressed ligand for the Mek4 and Sek receptor tyrosine kinases. *Cell* 79:157–168.

Cheng, H.-J., et al. (1995). Complementary gradients in expression and binding of PTP-NP and Mek4 in development of the topographic retinotectal projection map. *Cell* 82:371–381.

Chiang, M.-K., and Flanagan, J. G. (1995). Interaction between the Flk-1 receptor, vascular endothelial growth factor, and cell surface proteoglycan identified with a soluble receptor reagent. *Growth Factors* 12:1–10.

Cohen, P., and Cohen, P. T. W. (1989). Protein phosphatase come of age. *J. Biol. Chem.* 264:21345–21438.

den Hertog, J., et al. (1993). Receptor protein tyrosine phosphatase a activates pp60csrc and is involved in neuronal differentiation. *EMBO J.* 12:3789–3798.

Fantl, W. J., et al. (1993). Signaling by receptor tyrosine kinases. *Annu. Rev. Biochem.* 62:453–481.

Flanagan, J. G., and Leder, P. (1990). The kit ligand: a cell surface molecule altered in Steel mutant fibroblasts. *Cell* 63:185–194.

Gebbink, M., et al. (1993). Cell-cell adhesion mediated by a receptor-like protein tyrosine phosphatase. *J. Biol. Chem.* 268:16101–16104.

Grumet, M., et al. (1994). Interactions with tenascin and differential effects on cell adhesion of neurocan and phosphacan, two major chondroitin sulfate proteoglycans of nervous tissue. *J Biol. Chem.* 269:12142–12146.

Guz, Y., et al. (1995). Expression of murine STF-1, a putative insulin gene transcription factor, in b cells of pancreas, duodenal epithelium and pancreatic exocrine and endocrine progenitors during ontogeny. *Development* 121:11–18.

Hunter, T. (1989). Protein-tyrosine phosphatases: the other side of the coin. *Cell* 58:1013–1016.

Imamoto, A., et al. (1994). Genetics of signal transduction: tales from the mouse. *Curr. Opin. Gen. Dev.* 4:40–46.

Johnson, J. E., et al. (1992). Induction and repression of mammalian achaete-scute homologue (MASH) gene expression during neuronal differentiation of P19 embryonal carcinoma cells. *Development* 114:75–87.

Jones-Villeneuve, E. M. V., et al. (1982). Retinoic acid induces embryonal carcinoma cells to differentiate into neurons and glial cells. *J. Cell Biol.* 94:253–262.

Jonsson, J., et al. (1994). Insulin-promoter-factor 1 is required for pancreas development in mice. *Nature* 371:606–609.

Kingston, R. E., et al. (1994). Guanidinium methods for total RNA preparation. In: *Current Protocols in Molecular Biology* (eds. F. M. Ausubel, R. Brent, R. E. Kingston, D. D. Moore, J. G. Seidman, J. A. Smith and K. Struhl), pp. 4.2.1–4.2.8. New York: John Wiley & Sons, Inc.

Kozak, M. (1987). An analysis of 5'-noncoding sequences from 699 vertebrate messenger RNAs. *Nucleic Acids Res.* 15:8125–8148.

Lan, M. S., et al. (1994). Molecular cloning and identification of a receptor-type protein tyrosine phosphatase, IA-2, from human insulinoma. *DNA and Cell Biol.* 13:505–514.

Levy, J. B., et al. (1993). The cloning of a receptor-type protein tyrosine phosphatase expressed in the central nervous system. *J. Biol. Chem.* 268:10573–10581.

Lu, J., et al. (1994). Isolation, sequence and expression of a noval mouse brain cDNA, mIA-2, and its relatedness to members of the protein tyrosine phosphatase family. *Biochem. Biophys. Res. Commun.* 204:930–934.

MacBurney, M. W., et al. (1982). Control of muscle and neuronal differentiation in a cultured embryonal carcinoma cell line. *Nature* 299:165–167.

Milev, P., et al. (1991). Interactions of the chondroitin sulfate proteoglycan phosphacan, the extracellular domain of a receptor-type protein tyrosine phosphatase, with neuron, glial and neural cell adhesion molecules. *J. Cell Biol.* 127:1703–1715.

Miller, C. P., et al. (1994). IDX-1: a new homeodomain transcription factor expressed in rat pancreatic islet and duodenum that transactivates the somatostatin gene. *EMBO J.* 13:1145–1156.

Ohlsson, H., et al. (1993). IPF-1, a homeodomain-containing transactivator of the insulin gene. *EMBO J.* 2:4251–4259.

Peles, E., et al. (1995). The carbonic anhydrase domain of receptor tyrosine phosphatase b is a functional ligand for the axonal cell recognition molecule contactin. *Cell* 82:251–260.

Perkins, L. A., et al. (1992). Corkscrew encodes a putative protein tyrosine phosphatase that functions to transduce the terminal signal from the receptor tyrosine kinase torso. *Cell* 70:225–236.

Sap, J., et al. (1994). Receptor tyrosine phosphatase R-PTP-k mediates homophilic binding. *Mol. Cell. Biol.* 14:1–9.

Sato, T., et al. (1995). FAP-1: a protein tyrosine phosphatase that associates with Fas. *Science* 268:411–415.

Sharama, E., and Lombroso, P. J. (1995). A neuronal protein tyrosine phosphatase induced by nerve growth factor. *J. Biol. Chem.* 270:49–53.

Shultz, L. D., et al. (1993). Mutations at the murine moth-eaten locus are within the hematopoietic cell protein-tyrosine phosphatase (Hcph) gene. *Cell* 73:1445–1454.

Slack, J. M. W. (1995). Developmental biology of the pancreas. *Development* 121:1569–1580.

Stoker, A. W. (1994). Isoforms of a novel cell adhesion molecule-like protein tyrosine phosphatase are implicated in neural development. *Mech. Dev.* 46:201–217.

Teitelman, G., et al. (1993). Precursor cells of mouse endocrine pancreas coexpress insulin, glucagon and the neuronal proteins tyrosine hydroxylase and neuropeptide Y, but not pancreatic polypeptide. *Development* 118:1031–1039.

Tian, S. S., et al. (1991). Three receptor-linked protein-tyrosine phosphatases are selectively expressed on central nervous system axons in the Drosophila embryo. *Cell* 67:687–700.

Tsui, H. W., et al. (1993). Moth-eaten and viable moth-eaten mice have mutation in the haematopoietic cell phosphatase gene. *Nat. Gen.* 4:124–129.

van der Geer, P., et al. and Lindberg, R. A. (1994). Receptor protein-tyrosine kinases and their signal transduction pathways. *Annu. Rev. Cell Biol.* 10:251–337.

von Heijne, G. (1984). How signal sequences maintain cleavage specificity. *J. Mol. Biol.* 173:243–251.

Walton, K. M., and Dixon, J. E. (1993). Protein tyrosine phosphatase. *Annu. Rev. Biochem.* 62:101–120.

Wang, H., et al. (1995). Expression of receptor protein tyrosine phosphatase-s (RPTP-s) in the nervous system of the developing and adult rat. *J. Neurosci. Res.* 41:297–310.

Wessells, N. K., and Cohen, J. H. (1967). Early pancreas organogenesis: morphogenesis, tissue interactions, and mass effects. *Dev. Biol.* 15:237–270.

Wilkinson, D. G. (1992). In situ hybridization: A practical approach, New York: Oxford University Press.

Wilkinson, D. G., and Nieto, M. A. (1993). Detection of messenger RNA by in situ hybridization to tissue sections and whole mounts. *Meth. Enzymol.* 225:361–373.

Yan, H., et al. (1993). A novel receptor tyrosine phosphatase-s that is highly expressed in the nervous system. *J Biol. Chem.* 268:24880–24886.

Yang, X., et al. (1991). Two Drosophila receptor-like tyrosine phosphatase genes are expressed in a subset of developing axons and pioneer neurons in the embryonic CNS. *Cell* 67:661–673.

Zhang, J. S., and Longo, F. M. (1995). LAR tyrosine phosphatase receptor: alternative splicing is preferential to the nervous system, coordinated with cell growth and generates novel isoforms containing extensive CAG repeats. *J. Cell. Biol.* 128:415–431.

All of the above-cited references and publications are hereby incorporated by reference.

Equivalents

Those skilled in the art will recognize, or be able to ascertain using no more than routine experimentation, numerous equivalents to the specific polypeptides, nucleic acids, methods, assays and reagents described herein. Such equivalents are considered to be within the scope of this invention.

What is claimed is:

1. An isolated nucleic acid comprising a coding sequence encoding a polypeptide comprising a PTP-NP amino acid sequence that is at least 99 percent identical to SEQ ID NO: 2.

2. The isolated nucleic acid of claim 1, wherein the polypeptide comprises a Cys4 motif represented by the general formula CXXXXXXCXXXXXCXXXXXXXXC (SEQ ID NO: 9).

3. The nucleic acid of claim 2, wherein the Cys4 motif corresponds to the amino acid sequence Cys38–Cys60 of SEQ ID NO: 2.

4. The nucleic acid of claim 2, wherein the PTP-NP amino acid sequence comprises amino acids 28–600 of SEQ ID NO: 2.

5. The isolated nucleic acid of claim 1, wherein the PTP-NP amino acid sequence is identical to SEQ ID NO: 2.

6. An isolated nucleic acid comprising a coding sequence encoding a polypeptide comprising a PTP-NP amino acid sequence that is identical to amino acids 28–600 of SEQ ID NO: 2, wherein said polypeptide specifically binds to insulin-expressing β cells.

7. The isolated nucleic acid of claim 6, wherein the polypeptide further comprises a tyrosine phosphatase domain comprising amino acids 756–990 of SEQ ID NO: 2.

8. The isolated nucleic acid of claim 6, wherein the polypeptide further comprises a transmembrane domain comprising amino acids 601–625 of SEQ ID NO: 2.

9. The isolated nucleic acid of claim 8, wherein the polypeptide her comprises a tyrosine phosphatase domain comprising amino acids 756–990 of SEQ ID NO: 2.

10. An expression vector comprising the nucleic acid of claim 1, and a transcriptional regulatory sequence operably linked to the coding sequence.

11. A host cell comprising the expression vector of claim 10, wherein said cell expresses the polypeptide comprising a PTP-NP amino acid sequence.

12. A method of producing a recombinant polypeptide comprising a PTP-NP amino acid sequence comprising culturing the cell of claim 11 in a cell culture medium to cause expression of a polypeptide comprising a PTP-NP amino acid sequence encoded by the expression vector, and isolating the polypeptide from the cell culture.

13. An expression vector comprising the nucleic acid of claim 6, and a transcriptional regulatory sequence operably linked to the coding sequence.

14. A host cell comprising the expression vector of claim 13, wherein said cell expresses the polypeptide comprising a PTP-NP amino acid sequence.

15. A method of producing a recombinant polypeptide comprising a PTP-NP amino acid sequence comprising culturing the cell of claim 14 in a cell culture medium to cause expression of a polypeptide comprising a PTP-NP amino acid sequence encoded by the expression vector, and isolating the polypeptide from the cell culture.

* * * * *

SEQUENCE LISTING

```
<160> NUMBER OF SEQ ID NOS: 15

<210> SEQ ID NO 1
<211> LENGTH: 3200
<212> TYPE: DNA
<213> ORGANISM: Mus sp.
<220> FEATURE:
<221> NAME/KEY: CDS
<222> LOCATION: (33)..(3035)

<400> SEQUENCE: 1
ggccatggac tgagcgccaa ccggctgcgg gg atg ggg ccg ccg ctc ccg ctt      53
                                   Met Gly Pro Pro Leu Pro Leu
                                     1               5 ttg ctg ctg ctg ctg cta ccg ccg ccg ctg cct cgc gct ctg ccc gcc    101
Leu Leu Leu Leu Leu Leu Pro Pro Pro Leu Pro Arg Ala Leu Pro Ala
        10                  15                  20 ccc gcg tct gcc cgc ggc cgg cag ctc ccg ggg cgc ctg gga tgc ttg    149
Pro Ala Ser Ala Arg Gly Arg Gln Leu Pro Gly Arg Leu Gly Cys Leu
    25                  30                  35 ttt gag gat ggc ttg tgt gga tca ctg gag acc tgt gtg aac gat ggt    197
Phe Glu Asp Gly Leu Cys Gly Ser Leu Glu Thr Cys Val Asn Asp Gly
40                  45                  50                  55 gtg ttt gga aga tgt caa aag gtt ccg gtg atg gac act tac cga tat    245
Val Phe Gly Arg Cys Gln Lys Val Pro Val Met Asp Thr Tyr Arg Tyr
                60                  65                  70 gag gta cca cca gga gcc ctg ctg cac ctg aag gtc acc tta cag aag    293
Glu Val Pro Pro Gly Ala Leu Leu His Leu Lys Val Thr Leu Gln Lys
            75                  80                  85 ctc tcc cgt aca ggt ttc acg tgg caa gat gac tat acc cag cgt gtg    341
Leu Ser Arg Thr Gly Phe Thr Trp Gln Asp Asp Tyr Thr Gln Arg Val
        90                  95                 100 atc gcc cag gag ctt gca aac ctc ccc aag gcc tac cta tgg cat ggg    389
Ile Ala Gln Glu Leu Ala Asn Leu Pro Lys Ala Tyr Leu Trp His Gly
    105                 110                 115 gaa acg tcc ggc cca gcc agg tcc tta caa cag aat gct gac aat gaa    437
Glu Thr Ser Gly Pro Ala Arg Ser Leu Gln Gln Asn Ala Asp Asn Glu
120                 125                 130                 135 aaa tgg ttc agt ctg gag agg gag gtg gcc ctg gcc aag acc ctt cgg    485
Lys Trp Phe Ser Leu Glu Arg Glu Val Ala Leu Ala Lys Thr Leu Arg
                140                 145                 150 cgc tat ctg ccc tac ctg gag ctt ctg tcc cag acc cca aca gca aat    533
Arg Tyr Leu Pro Tyr Leu Glu Leu Leu Ser Gln Thr Pro Thr Ala Asn
```

```
                    155                 160                 165
gca cac tct agg ata gac cat gag act cgt cca gcc aag ggt gaa gac      581
Ala His Ser Arg Ile Asp His Glu Thr Arg Pro Ala Lys Gly Glu Asp
        170                 175                 180 tct tcc cct gag aac atc ctg acc tac gtg gcc cac aca tca gca ctg      629
Ser Ser Pro Glu Asn Ile Leu Thr Tyr Val Ala His Thr Ser Ala Leu
185                 190                 195 acc tat cct cct gca acc cgg gcc aag tat cct gat aac ctt ctg cgg      677
Thr Tyr Pro Pro Ala Thr Arg Ala Lys Tyr Pro Asp Asn Leu Leu Arg
200                 205                 210                 215 ccc ttt agc cgg ctc cag cca gat gag ctc agc ccc aag gta gac ggt      725
Pro Phe Ser Arg Leu Gln Pro Asp Glu Leu Ser Pro Lys Val Asp Gly
                220                 225                 230 gac ata gac aaa cag aaa ctg att gca gca ctg ggc gcc tac act gct      773
Asp Ile Asp Lys Gln Lys Leu Ile Ala Ala Leu Gly Ala Tyr Thr Ala
            235                 240                 245 cag agg ctt cct gga gaa aat gac cca gag cca cgg tac ctt gta cat      821
Gln Arg Leu Pro Gly Glu Asn Asp Pro Glu Pro Arg Tyr Leu Val His
        250                 255                 260 ggt tcc tcg aga gca cca agg cca ttc tca gca act gct ttg tct cag      869
Gly Ser Ser Arg Ala Pro Arg Pro Phe Ser Ala Thr Ala Leu Ser Gln
    265                 270                 275 aga tgg cct cca cct cct gga gac gcc aaa gac tcc ccg agt atg gat      917
Arg Trp Pro Pro Pro Pro Gly Asp Ala Lys Asp Ser Pro Ser Met Asp
280                 285                 290                 295 gat gac aca ctc ctg cag agt ctc ctg aag gat ttg cag cag aac tct      965
Asp Asp Thr Leu Leu Gln Ser Leu Leu Lys Asp Leu Gln Gln Asn Ser
                300                 305                 310 gaa gtg gac cgc ctg ggc ccc ctg aag gag gag aaa gca gac tca gtt     1013
Glu Val Asp Arg Leu Gly Pro Leu Lys Glu Glu Lys Ala Asp Ser Val
            315                 320                 325 gct gga gcc ata caa agt gat cct gca gag gga agc caa gaa agc cac     1061
Ala Gly Ala Ile Gln Ser Asp Pro Ala Glu Gly Ser Gln Glu Ser His
        330                 335                 340 ggg aga ggg gct gaa gga cag cca aga gag cag aca gat gcc cca gag     1109
Gly Arg Gly Ala Glu Gly Gln Pro Arg Glu Gln Thr Asp Ala Pro Glu
    345                 350                 355 aca atg ctt caa gat cac aga cta tca gat gtg gat gac cca gtg tac     1157
Thr Met Leu Gln Asp His Arg Leu Ser Asp Val Asp Asp Pro Val Tyr
360                 365                 370                 375 aag gag gtc aac cgt ctg agc ttc cag ctt ggg gac ctc ttg aag gac     1205
Lys Glu Val Asn Arg Leu Ser Phe Gln Leu Gly Asp Leu Leu Lys Asp
                380                 385                 390 tat ggg tct cat ctc tta cct gaa ggt ccc ctt cta gaa aaa tcc tcc     1253
Tyr Gly Ser His Leu Leu Pro Glu Gly Pro Leu Leu Glu Lys Ser Ser
            395                 400                 405 aga gaa gag att aag aag tca gag cag cca gag gag gtc ttg tct tca     1301
Arg Glu Glu Ile Lys Lys Ser Glu Gln Pro Glu Glu Val Leu Ser Ser
        410                 415                 420 gaa gag gag act gct ggg gtg gag cat gtg agg agc cgg act tac tcc     1349
Glu Glu Glu Thr Ala Gly Val Glu His Val Arg Ser Arg Thr Tyr Ser
    425                 430                 435 aaa gac cta ttt gaa agg aaa cca aac tca gag ccc cag ccc agg agg     1397
Lys Asp Leu Phe Glu Arg Lys Pro Asn Ser Glu Pro Gln Pro Arg Arg
440                 445                 450                 455 ctt gag gat cag ttc caa aac cga gct cca gag ttg tgg gag gat gaa     1445
Leu Glu Asp Gln Phe Gln Asn Arg Ala Pro Glu Leu Trp Glu Asp Glu
                460                 465                 470 gaa agc ctc aaa ttg gca gca cag ggt ccc cct agt gga ggc cta cag     1493
```

```
                Glu Ser Leu Lys Leu Ala Ala Gln Gly Pro Ser Gly Gly Leu Gln
                                475                 480                 485 ctg gaa gtg cag cct tct gag gaa cag cag gga tac atc ctc aca gga         1541
Leu Glu Val Gln Pro Ser Glu Glu Gln Gln Gly Tyr Ile Leu Thr Gly
            490                 495                 500 aac aac cct cta agt cca gag aag ggg aag cag ctg atg gac caa gtt         1589
Asn Asn Pro Leu Ser Pro Glu Lys Gly Lys Gln Leu Met Asp Gln Val
505                 510                 515 gcc cac atc ctc cgg gta cct tcc agc ttc ttt gca gat atc aaa gtt         1637
Ala His Ile Leu Arg Val Pro Ser Ser Phe Phe Ala Asp Ile Lys Val
520                 525                 530                 535 ttg gga cca gca gtg acc ttc aaa gta agt gcc aac atc caa aac atg         1685
Leu Gly Pro Ala Val Thr Phe Lys Val Ser Ala Asn Ile Gln Asn Met
                540                 545                 550 aca act gcc gat gtc atc aag gct gca gct gac aac aaa gac cag ctg         1733
Thr Thr Ala Asp Val Ile Lys Ala Ala Ala Asp Asn Lys Asp Gln Leu
                555                 560                 565 gag aag gca act gga ctg aca atc ctt caa agt gga atc agg ccg aag         1781
Glu Lys Ala Thr Gly Leu Thr Ile Leu Gln Ser Gly Ile Arg Pro Lys
                570                 575                 580 gga aag ctc aaa ctc ctg ccg cat cag gaa gag caa gag gac tct acc         1829
Gly Lys Leu Lys Leu Leu Pro His Gln Glu Glu Gln Glu Asp Ser Thr
585                 590                 595 aag ttc att ttg ctc acc ttc ctc tcc att gcc tgc atc ctg ggg gtt         1877
Lys Phe Ile Leu Leu Thr Phe Leu Ser Ile Ala Cys Ile Leu Gly Val
600                 605                 610                 615 ctc ctg gct tcc agc ctt gcc tac tgc ctc cgc cac aac tca cac tac         1925
Leu Leu Ala Ser Ser Leu Ala Tyr Cys Leu Arg His Asn Ser His Tyr
                620                 625                 630 aag ctg aag gac aag ttg tct gga cta ggc gct gac ccc agt gca gat         1973
Lys Leu Lys Asp Lys Leu Ser Gly Leu Gly Ala Asp Pro Ser Ala Asp
                635                 640                 645 gcc act gaa gcc tac cag gag cta tgc cgc cag cgt atg gct gtt cgt         2021
Ala Thr Glu Ala Tyr Gln Glu Leu Cys Arg Gln Arg Met Ala Val Arg
                650                 655                 660 cca cag gac cgc tct gag gga cca cat aca tca cgc atc aac agc gtc         2069
Pro Gln Asp Arg Ser Glu Gly Pro His Thr Ser Arg Ile Asn Ser Val
665                 670                 675 tca tcc cag ttc agc gat ggg ccg atg cct agt cct tcg gct cgg agc         2117
Ser Ser Gln Phe Ser Asp Gly Pro Met Pro Ser Pro Ser Ala Arg Ser
680                 685                 690                 695 agc act tca tcc tgg tct gag gag cct gtc cag tcc aac atg gac atc         2165
Ser Thr Ser Ser Trp Ser Glu Glu Pro Val Gln Ser Asn Met Asp Ile
                700                 705                 710 tct act ggc cac atg atc ctg gcc tac atg gaa gac cat ctg aag aac         2213
Ser Thr Gly His Met Ile Leu Ala Tyr Met Glu Asp His Leu Lys Asn
                715                 720                 725 aag aac cgc ctg gag aag gag tgg gaa gca ctg tgc gcc tac caa gca         2261
Lys Asn Arg Leu Glu Lys Glu Trp Glu Ala Leu Cys Ala Tyr Gln Ala
                730                 735                 740 gag ccc aac agc tca ctt gtg gcc cag aga gag gag aat gca ccc aag         2309
Glu Pro Asn Ser Ser Leu Val Ala Gln Arg Glu Glu Asn Ala Pro Lys
                745                 750                 755 aac cgt tcc ctg gct gtg ctg acc tat gac cac tcc agg atc ctg ttg         2357
Asn Arg Ser Leu Ala Val Leu Thr Tyr Asp His Ser Arg Ile Leu Leu
760                 765                 770                 775 aag tct caa aac agc cat ggc agt tcc gac tac atc aat gcc agc ccc         2405
Lys Ser Gln Asn Ser His Gly Ser Ser Asp Tyr Ile Asn Ala Ser Pro
                780                 785                 790
```

```
att atg gac cat gac cca cga aac ccc gca tac att gcc acc caa ggc      2453
Ile Met Asp His Asp Pro Arg Asn Pro Ala Tyr Ile Ala Thr Gln Gly
            795                 800                 805 cca ctt ccc gcc acg gtg gcc gac ttc tgg cag atg gtg tgg gaa agc      2501
Pro Leu Pro Ala Thr Val Ala Asp Phe Trp Gln Met Val Trp Glu Ser
    810                 815                 820 ggc tgt gca gtc att gtc atg ctg aca ccc ctc tcc gag aac ggc gtc      2549
Gly Cys Ala Val Ile Val Met Leu Thr Pro Leu Ser Glu Asn Gly Val
825                 830                 835 cgg cag tgc cat cac tac tgg ccc gat gaa ggc tcc aac ctc tac cat      2597
Arg Gln Cys His His Tyr Trp Pro Asp Glu Gly Ser Asn Leu Tyr His
840                 845                 850                 855 gtc tac gag gtc aat cta gtc tct gag cac ata tgg tgc cag gat ttc      2645
Val Tyr Glu Val Asn Leu Val Ser Glu His Ile Trp Cys Gln Asp Phe
            860                 865                 870 ctg gtg aga agc ttt tac ctg aag aac ctg cag acc aac gag act cgc      2693
Leu Val Arg Ser Phe Tyr Leu Lys Asn Leu Gln Thr Asn Glu Thr Arg
    875                 880                 885 acg gtg acc cag ttc cac ttc ctg agt tgg tat gac cag gga gtc cct      2741
Thr Val Thr Gln Phe His Phe Leu Ser Trp Tyr Asp Gln Gly Val Pro
890                 895                 900 tcc tcc acg agg tca ctc ctg gat ttc cgc aga aaa gtg aac aaa tgc      2789
Ser Ser Thr Arg Ser Leu Leu Asp Phe Arg Arg Lys Val Asn Lys Cys
905                 910                 915 tac cga ggc cgc tct tgt ccg atc att gtc cat tgc agt gac ggc gcc      2837
Tyr Arg Gly Arg Ser Cys Pro Ile Ile Val His Cys Ser Asp Gly Ala
920                 925                 930                 935 ggc agg agt gga acc tac gtc ctg att gac atg gtt ctc aat aag atg      2885
Gly Arg Ser Gly Thr Tyr Val Leu Ile Asp Met Val Leu Asn Lys Met
            940                 945                 950 gcc aaa ggt gct aaa gag att gat atc gca gcg acc ctg gag cac ttg      2933
Ala Lys Gly Ala Lys Glu Ile Asp Ile Ala Ala Thr Leu Glu His Leu
    955                 960                 965 agg gac cag aga cca ggc atg gtc cag aca aag gag cag ttt gag ttt      2981
Arg Asp Gln Arg Pro Gly Met Val Gln Thr Lys Glu Gln Phe Glu Phe
970                 975                 980 gcg ctg aca gct gtg gct gag gag gtg aat gcc atc ctg aag gcc ctt      3029
Ala Leu Thr Ala Val Ala Glu Glu Val Asn Ala Ile Leu Lys Ala Leu
985                 990                 995 ccc cag taggcgctga agctggagct ggcgggaccc caccacgagt gcttccagaa        3085
Pro Gln
1000 ccgcaacagg atatcagtcc tgcatcttct gtgtagtaac agggtcttcg ggctccacag    3145 tcagtgcagg tggctagtca tgtgtacttc tgattgacca aatagcacat gtgtg          3200

<210> SEQ ID NO 2
<211> LENGTH: 1001
<212> TYPE: PRT
<213> ORGANISM: Mus sp.

<400> SEQUENCE: 2

Met Gly Pro Pro Leu Pro Leu Leu Leu Leu Leu Pro Pro Pro
  1               5                  10                  15

Leu Pro Arg Ala Leu Pro Ala Pro Ala Ser Ala Arg Gly Arg Gln Leu
                20                  25                  30

Pro Gly Arg Leu Gly Cys Leu Phe Glu Asp Gly Leu Cys Gly Ser Leu
            35                  40                  45

Glu Thr Cys Val Asn Asp Gly Val Phe Gly Arg Cys Gln Lys Val Pro
        50                  55                  60
```

-continued

```
Val Met Asp Thr Tyr Arg Tyr Glu Val Pro Pro Gly Ala Leu Leu His
 65                  70                  75                  80

Leu Lys Val Thr Leu Gln Lys Leu Ser Arg Thr Gly Phe Thr Trp Gln
                 85                  90                  95

Asp Asp Tyr Thr Gln Arg Val Ile Ala Gln Glu Leu Ala Asn Leu Pro
                100                 105                 110

Lys Ala Tyr Leu Trp His Gly Glu Thr Ser Gly Pro Ala Arg Ser Leu
                115                 120                 125

Gln Gln Asn Ala Asp Asn Glu Lys Trp Phe Ser Leu Glu Arg Glu Val
            130                 135                 140

Ala Leu Ala Lys Thr Leu Arg Arg Tyr Leu Pro Tyr Leu Glu Leu Leu
145                 150                 155                 160

Ser Gln Thr Pro Thr Ala Asn Ala His Ser Arg Ile Asp His Glu Thr
                165                 170                 175

Arg Pro Ala Lys Gly Glu Asp Ser Ser Pro Glu Asn Ile Leu Thr Tyr
                180                 185                 190

Val Ala His Thr Ser Ala Leu Thr Tyr Pro Pro Ala Thr Arg Ala Lys
            195                 200                 205

Tyr Pro Asp Asn Leu Leu Arg Pro Phe Ser Arg Leu Gln Pro Asp Glu
            210                 215                 220

Leu Ser Pro Lys Val Asp Gly Asp Ile Asp Lys Gln Lys Leu Ile Ala
225                 230                 235                 240

Ala Leu Gly Ala Tyr Thr Ala Gln Arg Leu Pro Gly Glu Asn Asp Pro
                245                 250                 255

Glu Pro Arg Tyr Leu Val His Gly Ser Ser Arg Ala Pro Arg Pro Phe
                260                 265                 270

Ser Ala Thr Ala Leu Ser Gln Arg Trp Pro Pro Pro Gly Asp Ala
                275                 280                 285

Lys Asp Ser Pro Ser Met Asp Asp Thr Leu Leu Gln Ser Leu Leu
            290                 295                 300

Lys Asp Leu Gln Gln Asn Ser Glu Val Asp Arg Leu Gly Pro Leu Lys
305                 310                 315                 320

Glu Glu Lys Ala Asp Ser Val Ala Gly Ala Ile Gln Ser Asp Pro Ala
                325                 330                 335

Glu Gly Ser Gln Glu Ser His Gly Arg Gly Ala Glu Gly Gln Pro Arg
                340                 345                 350

Glu Gln Thr Asp Ala Pro Glu Thr Met Leu Gln Asp His Arg Leu Ser
                355                 360                 365

Asp Val Asp Asp Pro Val Tyr Lys Glu Val Asn Arg Leu Ser Phe Gln
            370                 375                 380

Leu Gly Asp Leu Leu Lys Asp Tyr Gly Ser His Leu Leu Pro Glu Gly
385                 390                 395                 400

Pro Leu Leu Glu Lys Ser Ser Arg Glu Glu Ile Lys Lys Ser Glu Gln
                405                 410                 415

Pro Glu Glu Val Leu Ser Ser Glu Glu Thr Ala Gly Val Glu His
                420                 425                 430

Val Arg Ser Arg Thr Tyr Ser Lys Asp Leu Phe Glu Arg Lys Pro Asn
            435                 440                 445

Ser Glu Pro Gln Pro Arg Arg Leu Glu Asp Gln Phe Gln Asn Arg Ala
            450                 455                 460

Pro Glu Leu Trp Glu Asp Glu Glu Ser Leu Lys Leu Ala Ala Gln Gly
465                 470                 475                 480
```

-continued

```
Pro Pro Ser Gly Gly Leu Gln Leu Glu Val Gln Pro Ser Glu Gln
            485                 490                 495

Gln Gly Tyr Ile Leu Thr Gly Asn Asn Pro Leu Ser Pro Glu Lys Gly
            500                 505                 510

Lys Gln Leu Met Asp Gln Val Ala His Ile Leu Arg Val Pro Ser Ser
            515                 520                 525

Phe Phe Ala Asp Ile Lys Val Leu Gly Pro Ala Val Thr Phe Lys Val
    530                 535                 540

Ser Ala Asn Ile Gln Asn Met Thr Thr Ala Asp Val Ile Lys Ala Ala
545                 550                 555                 560

Ala Asp Asn Lys Asp Gln Leu Glu Lys Ala Thr Gly Leu Thr Ile Leu
                565                 570                 575

Gln Ser Gly Ile Arg Pro Lys Gly Lys Leu Lys Leu Pro His Gln
            580                 585                 590

Glu Glu Gln Glu Asp Ser Thr Lys Phe Ile Leu Leu Thr Phe Leu Ser
            595                 600                 605

Ile Ala Cys Ile Leu Gly Val Leu Leu Ala Ser Ser Leu Ala Tyr Cys
            610                 615                 620

Leu Arg His Asn Ser His Tyr Lys Leu Lys Asp Lys Leu Ser Gly Leu
625                 630                 635                 640

Gly Ala Asp Pro Ser Ala Asp Ala Thr Glu Ala Tyr Gln Glu Leu Cys
                645                 650                 655

Arg Gln Arg Met Ala Val Arg Pro Gln Asp Arg Ser Glu Gly Pro His
                660                 665                 670

Thr Ser Arg Ile Asn Ser Val Ser Gln Phe Ser Asp Gly Pro Met
            675                 680                 685

Pro Ser Pro Ser Ala Arg Ser Ser Thr Ser Ser Trp Ser Glu Glu Pro
690                 695                 700

Val Gln Ser Asn Met Asp Ile Ser Thr Gly His Met Ile Leu Ala Tyr
705                 710                 715                 720

Met Glu Asp His Leu Lys Asn Lys Asn Arg Leu Glu Lys Glu Trp Glu
                725                 730                 735

Ala Leu Cys Ala Tyr Gln Ala Glu Pro Asn Ser Ser Leu Val Ala Gln
            740                 745                 750

Arg Glu Glu Asn Ala Pro Lys Asn Arg Ser Leu Ala Val Leu Thr Tyr
            755                 760                 765

Asp His Ser Arg Ile Leu Leu Lys Ser Gln Asn Ser His Gly Ser Ser
770                 775                 780

Asp Tyr Ile Asn Ala Ser Pro Ile Met Asp His Asp Pro Arg Asn Pro
785                 790                 795                 800

Ala Tyr Ile Ala Thr Gln Gly Pro Leu Pro Ala Thr Val Ala Asp Phe
                805                 810                 815

Trp Gln Met Val Trp Glu Ser Gly Cys Ala Val Ile Val Met Leu Thr
            820                 825                 830

Pro Leu Ser Glu Asn Gly Val Arg Gln Cys His His Tyr Trp Pro Asp
            835                 840                 845

Glu Gly Ser Asn Leu Tyr His Val Tyr Glu Val Asn Leu Val Ser Glu
850                 855                 860

His Ile Trp Cys Gln Asp Phe Leu Val Arg Ser Phe Tyr Leu Lys Asn
865                 870                 875                 880

Leu Gln Thr Asn Glu Thr Arg Thr Val Thr Gln Phe His Phe Leu Ser
                885                 890                 895

Trp Tyr Asp Gln Gly Val Pro Ser Ser Thr Arg Ser Leu Leu Asp Phe
```

```
                       900             905              910
Arg Arg Lys Val Asn Lys Cys Tyr Arg Gly Arg Ser Cys Pro Ile Ile
        915                 920                 925

Val His Cys Ser Asp Gly Ala Gly Arg Ser Gly Thr Tyr Val Leu Ile
        930                 935                 940

Asp Met Val Leu Asn Lys Met Ala Lys Gly Ala Lys Glu Ile Asp Ile
945                 950                 955                 960

Ala Ala Thr Leu Glu His Leu Arg Asp Gln Arg Pro Gly Met Val Gln
                    965                 970                 975

Thr Lys Glu Gln Phe Glu Phe Ala Leu Thr Ala Val Ala Glu Glu Val
                980                 985                 990

Asn Ala Ile Leu Lys Ala Leu Pro Gln
                995                 1000

<210> SEQ ID NO 3
<211> LENGTH: 246
<212> TYPE: PRT
<213> ORGANISM: Mus sp.

<400> SEQUENCE: 3

Asn Ala Pro Lys Asn Arg Ser Leu Ala Val Leu Thr Tyr Asp His Ser
  1               5                  10                  15

Arg Ile Leu Leu Lys Ser Gln Asn Ser His Gly Ser Ser Asp Tyr Ile
                20                  25                  30

Asn Ala Ser Pro Ile Met Asp His Asp Pro Arg Asn Pro Ala Tyr Ile
            35                  40                  45

Ala Thr Gln Gly Pro Leu Pro Ala Thr Val Ala Asp Phe Trp Gln Met
         50                  55                  60

Val Trp Glu Ser Gly Cys Ala Val Ile Val Met Leu Thr Pro Leu Ser
 65                  70                  75                  80

Glu Asn Gly Val Arg Gln Cys His His Tyr Trp Pro Asp Glu Gly Ser
                 85                  90                  95

Asn Leu Tyr His Val Tyr Glu Val Asn Leu Val Ser Glu His Ile Trp
                100                 105                 110

Cys Gln Asp Phe Leu Val Arg Ser Phe Tyr Leu Lys Asn Leu Gln Thr
            115                 120                 125

Asn Glu Thr Arg Thr Val Thr Gln Phe His Phe Leu Ser Trp Tyr Asp
        130                 135                 140

Gln Gly Val Pro Ser Ser Thr Arg Ser Leu Leu Asp Phe Arg Arg Lys
145                 150                 155                 160

Val Asn Lys Cys Tyr Arg Gly Arg Ser Cys Pro Ile Ile Val His Cys
                165                 170                 175

Ser Asp Gly Ala Gly Arg Ser Gly Thr Tyr Val Leu Ile Asp Met Val
            180                 185                 190

Leu Asn Lys Met Ala Lys Gly Ala Lys Glu Ile Asp Ile Ala Ala Thr
        195                 200                 205

Leu Glu His Leu Arg Asp Gln Arg Pro Gly Met Val Gln Thr Lys Glu
    210                 215                 220

Gln Phe Glu Phe Ala Leu Thr Ala Val Ala Glu Glu Val Asn Ala Ile
225                 230                 235                 240

Leu Lys Ala Leu Pro Gln
                245

<210> SEQ ID NO 4
<211> LENGTH: 246
```

-continued

```
<212> TYPE: PRT
<213> ORGANISM: Mus sp.

<400> SEQUENCE: 4

Asn Ile Lys Lys Asn Arg His Pro Asp Phe Leu Pro Tyr Asp His Ala
  1               5                  10                  15

Arg Ile Lys Leu Lys Val Glu Ser Ser Pro Ser Arg Ser Asp Tyr Ile
                 20                  25                  30

Asn Ala Ser Pro Ile Ile Glu His Asp Pro Arg Met Pro Ala Tyr Ile
             35                  40                  45

Ala Thr Gln Gly Pro Leu Ser His Thr Ile Ala Asp Phe Trp Gln Met
         50                  55                  60

Val Trp Glu Ser Gly Cys Thr Val Ile Val Met Leu Thr Pro Leu Val
 65                  70                  75                  80

Glu Asp Gly Val Lys Gln Cys Asp Arg Tyr Trp Pro Asp Gly Gly Ser
                 85                  90                  95

Ser Leu Tyr His Val Tyr Glu Val Asn Leu Val Ser Glu His Ile Trp
            100                 105                 110

Cys Glu Asp Phe Leu Val Arg Ser Phe Tyr Leu Lys Asn Leu Gln Thr
            115                 120                 125

Gln Glu Thr Arg Thr Leu Thr Gln Phe His Phe Leu Ser Trp Pro Ala
        130                 135                 140

Glu Gly Thr Pro Ala Ser Thr Arg Pro Leu Leu Asp Phe Arg Arg Lys
145                 150                 155                 160

Val Asn Lys Cys Tyr Arg Gly Arg Ser Cys Pro Ile Ile Val His Cys
                165                 170                 175

Ser Asp Gly Ala Gly Arg Thr Gly Thr Tyr Ile Leu Ile Asp Met Val
            180                 185                 190

Leu Asn Arg Met Ala Lys Gly Val Lys Glu Ile Asp Ile Ala Ala Thr
        195                 200                 205

Leu Glu His Val Arg Asp Gln Arg Pro Gly Leu Val Arg Ser Lys Asp
    210                 215                 220

Gln Phe Glu Phe Ala Leu Thr Ala Val Ala Glu Glu Val Asn Ala Ile
225                 230                 235                 240

Leu Lys Ala Leu Pro Gln
                245

<210> SEQ ID NO 5
<211> LENGTH: 242
<212> TYPE: PRT
<213> ORGANISM: Caenorhabditis elegans

<400> SEQUENCE: 5

Phe Ala Ser Gln Asn Arg Thr Ile Leu Pro Glu Asp Asn Ile Val
  1               5                  10                  15

Asp Ile Asp Gly Lys Thr Ala Glu Asn Glu Asp Phe Tyr Leu Asn Ala
                 20                  25                  30

Ser Phe Ile Tyr Asp Asp Pro Arg Gln Ala Val Tyr Ile Ala Ala
             35                  40                  45

Gln Thr Pro Ala Ser Ser Gln Ile Ala Ala Phe Trp Gln Thr Thr Trp
         50                  55                  60

Gln His Gly Val Cys Leu Val Val Asn Leu Ser Thr Pro Glu Glu Cys
 65                  70                  75                  80

Lys Gln Glu Lys Asn Tyr Trp Pro Asp Thr Gly Ser Glu Val His Gly
                 85                  90                  95
```

```
Ala Glu Glu Ile His Leu Val Ser Glu His Ile Trp Ser Asp Asp Tyr
            100                 105                 110

Leu Val Arg Ser Phe Tyr Leu Lys Asn Leu Gln Asn Ser Gln Thr Arg
        115                 120                 125

Thr Ile Thr Gln Phe His Tyr Leu Ser Trp Gln Lys Glu Ser Thr Pro
    130                 135                 140

Thr Ser Ala Lys Ser Ile Leu Glu Phe Arg Arg Lys Val Asn Lys Ser
145                 150                 155                 160

Tyr Arg Gly Arg Ser Ser Ala Val Leu Val His Ser Trp Asp Gly Ser
                165                 170                 175

Gly Arg Thr Gly Val Tyr Cys Ala Val Asp Val Leu Cys Ala Arg Leu
            180                 185                 190

Leu Arg Gly Ile Arg Gln Ile Asp Val Val Ala Thr Val Glu His Leu
        195                 200                 205

Arg Asp Gln Arg Asp Gly His Val Ala Thr Gly Asp Gln Phe Lys Leu
    210                 215                 220

Val Tyr Gly Cys Val Ala Gln Glu Val Asn His Leu Leu Lys Ser Ile
225                 230                 235                 240

Ala Thr

<210> SEQ ID NO 6
<211> LENGTH: 70
<212> TYPE: PRT
<213> ORGANISM: Mus sp.

<400> SEQUENCE: 6

Gly Cys Leu Phe Glu Asp Gly Leu Cys Gly Ser Leu Glu Thr Cys Val
1               5                   10                  15

Asn Asp Gly Val Phe Gly Arg Cys Gln Lys Val Pro Val Met Asp Thr
                20                  25                  30

Tyr Arg Tyr Glu Val Pro Pro Gly Ala Leu Leu His Leu Lys Val Thr
            35                  40                  45

Leu Gln Lys Leu Ser Arg Thr Gly Phe Thr Trp Gln Asp Asp Tyr Thr
        50                  55                  60

Gln Arg Val Ile Ala Gln
65                  70

<210> SEQ ID NO 7
<211> LENGTH: 70
<212> TYPE: PRT
<213> ORGANISM: Mus sp.

<400> SEQUENCE: 7

Gly Cys Leu Phe Asp Arg Arg Leu Cys Ser His Leu Glu Val Cys Ile
1               5                   10                  15

Gln Asp Gly Leu Phe Gly Gln Cys Gln Ala Gly Val Gly Gln Ala Arg
                20                  25                  30

Pro Leu Leu Gln Val Thr Ser Pro Val Leu Gln Arg Leu Gln Gly Val
            35                  40                  45

Leu Arg Gln Leu Met Ser Gln Gly Leu Ser Trp His Asp Asp Leu Thr
        50                  55                  60

Gln His Val Ile Ser Gln
65                  70

<210> SEQ ID NO 8
<211> LENGTH: 73
<212> TYPE: PRT
```

```
<213> ORGANISM: Caenorhabditis elegans

<400> SEQUENCE: 8

Cys Cys Asn Leu Ser Glu Asn Leu Cys Asp Asn Asp Glu Ser Cys Tyr
 1               5                  10                  15

Pro Asp Gly Val Phe Gly Gln Cys Tyr Ser Ser Glu Ser Gly Ser Pro
                20                  25                  30

Glu Pro Thr Val Leu Asp Asn Leu Asp Asp Thr Gln Leu Glu Leu Leu
            35                  40                  45

Lys Leu Glu Leu Thr Arg Leu Ala Ala Lys Asp Lys Asp Trp Gly Asp
     50                  55                  60

Glu Glu Thr Gln Cys Val Leu Ala Tyr
 65                  70

<210> SEQ ID NO 9
<211> LENGTH: 23
<212> TYPE: PRT
<213> ORGANISM: Artificial Sequence
<220> FEATURE:
<223> OTHER INFORMATION: Description of Artificial Sequence: Consensus
      peptide
<221> NAME/KEY: MOD_RES
<222> LOCATION: (2)..(7)
<223> OTHER INFORMATION: Variable amino acid
<221> NAME/KEY: MOD_RES
<222> LOCATION: (9)..(13)
<223> OTHER INFORMATION: Variable amino acid
<221> NAME/KEY: MOD_RES
<222> LOCATION: (15)..(22)
<223> OTHER INFORMATION: Variable amino acid

<400> SEQUENCE: 9

Cys Xaa Xaa Xaa Xaa Xaa Xaa Cys Xaa Xaa Xaa Xaa Xaa Cys Xaa Xaa
 1               5                  10                  15

Xaa Xaa Xaa Xaa Xaa Xaa Cys
                20

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Degenerate
      primer
<221> NAME/KEY: modified_base
<222> LOCATION: (9)
<223> OTHER INFORMATION: a, t, c, g, other or unknown
<221> NAME/KEY: modified_base
<222> LOCATION: (15)
<223> OTHER INFORMATION: a, t, c, g, other or unknown

<400> SEQUENCE: 10
ttytggmrna tgrtntgg                                                18

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (5)
<223> OTHER INFORMATION: Ile or Val

<400> SEQUENCE: 11

Phe Trp Arg Met Xaa Trp
```

-continued

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Degenerate
    primer
<221> NAME/KEY: modified_base
<222> LOCATION: (3)
<223> OTHER INFORMATION: a, t, c, g, other or unknown
<221> NAME/KEY: modified_base
<222> LOCATION: (6)
<223> OTHER INFORMATION: a, t, c, g, other or unknown
<221> NAME/KEY: modified_base
<222> LOCATION: (12)
<223> OTHER INFORMATION: a, t, c, g, other or unknown

<400> SEQUENCE: 12
aynccngcns wrcartg                                                17

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
    peptide
<221> NAME/KEY: MOD_RES
<222> LOCATION: (6)
<223> OTHER INFORMATION: Ile or Val

<400> SEQUENCE: 13

His Cys Ser Ala Gly Xaa
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
    peptide
<221> NAME/KEY: MOD_RES
<222> LOCATION: (3)
<223> OTHER INFORMATION: Arg or Gln
<221> NAME/KEY: MOD_RES
<222> LOCATION: (5)
<223> OTHER INFORMATION: Ile or Val

<400> SEQUENCE: 14

Phe Trp Xaa Met Xaa Trp
 1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 15

His Cys Ser Ala Gly Val
 1               5